United States Patent
Magnani et al.

(10) Patent No.: US 9,109,002 B2
(45) Date of Patent: Aug. 18, 2015

(54) E-SELECTIN ANTAGONIST COMPOUNDS, COMPOSITIONS, AND METHODS OF USE

(71) Applicant: GLYCOMIMETICS, INC., Gaithersburg, MD (US)

(72) Inventors: John L. Magnani, Gaithersburg, MD (US); Arun K. Sarkar, North Potomac, MD (US); Myung-Gi Baek, Boyds, MD (US); Frank E. Anderson, III, Gaithersburg, MD (US); Yanhong Li, North Potomac, MD (US)

(73) Assignee: GlycoMimetics, Inc., Rockville, MD (US)

( * ) Notice: Subject to any disclaimer, the term of this patent is extended or adjusted under 35 U.S.C. 154(b) by 0 days.

(21) Appl. No.: 14/367,561

(22) PCT Filed: Dec. 21, 2012

(86) PCT No.: PCT/US2012/071519
§ 371 (c)(1),
(2) Date: Jun. 20, 2014

(87) PCT Pub. No.: WO2013/096926
PCT Pub. Date: Jun. 27, 2013

(65) Prior Publication Data
US 2015/0110808 A1    Apr. 23, 2015

Related U.S. Application Data

(60) Provisional application No. 61/579,646, filed on Dec. 22, 2011, provisional application No. 61/583,547, filed on Jan. 5, 2012, provisional application No. 61/704,399, filed on Sep. 21, 2012, provisional application No. 61/704,424, filed on Sep. 21, 2012, provisional application No. 61/734,924, filed on Dec. 7, 2012.

(51) Int. Cl.
C07H 15/207    (2006.01)
C07H 11/00     (2006.01)
A61K 31/7034   (2006.01)
A61K 45/06     (2006.01)
C07H 15/26     (2006.01)

(52) U.S. Cl.
CPC .......... *C07H 15/207* (2013.01); *A61K 31/7034* (2013.01); *A61K 45/06* (2013.01); *C07H 15/26* (2013.01)

(58) Field of Classification Search
None
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Abraham, W.M. et al.,"Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al.,"A rapid microplate method for quantifying inhibition of bacterial adhesion to eukaryotic cells," Journal of Microbiological Methods 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.

(Continued)

*Primary Examiner* — Traviss C McIntosh, III
(74) *Attorney, Agent, or Firm* — Finnegan, Henderson, Farabow, Garrett & Dunner, L.L.P.

(57) ABSTRACT

Methods and compositions using E-selectin antagonists are provided for the treatment and prevention of diseases and disorders treatable by inhibiting binding of E-selectin to an E-selectin ligand. Described herein are E-selectin antagonists including, for example, glycomimetic compounds, antibodies, aptamers and peptides that are useful in methods for treatment of cancers, and treatment and prevention of metastasis, inhibiting infiltration of the cancer cells into bone marrow, reducing or inhibiting adhesion of the cancer cells to endothelial cells including cells in bone marrow, and inhibiting thrombus formation.

15 Claims, 7 Drawing Sheets

(56) References Cited

U.S. PATENT DOCUMENTS

| | | | |
|---|---|---|---|
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 12/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Ito |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesewitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0187171 A1 | 8/2005 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0054870 A1 | 3/2007 | Magnani et al. |
| 2007/0054930 A1 | 3/2007 | Shim et al. |
| 2007/0213278 A1 | 9/2007 | Wong et al. |

(56) References Cited

U.S. PATENT DOCUMENTS

| | | |
|---|---|---|
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0054334 A1 | 2/2009 | Mutz et al. |
| 2009/0253646 A1 | 10/2009 | Magnani |
| 2009/0312278 A1 | 12/2009 | Magnani et al. |
| 2010/0215575 A1 | 8/2010 | O'Neill et al. |
| 2010/0240773 A1 | 9/2010 | Korzekwa et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0257380 A1 | 10/2011 | Ernst et al. |
| 2012/0202762 A1 | 8/2012 | Magnani |
| 2012/0258043 A1 | 10/2012 | Ranganathan et al. |
| 2013/0184229 A1 | 7/2013 | Magnani et al. |
| 2013/0261070 A1 | 10/2013 | Magnani et al. |
| 2013/0281646 A1 | 10/2013 | Korzekwa et al. |
| 2014/0178303 A1 | 6/2014 | Magnani et al. |
| 2015/0051164 A1 | 2/2015 | Magnani |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| JP | 2009-507031 | 2/2009 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/46771 | 10/1998 |
| WO | WO 99/42130 | 8/1999 |
| WO | WO 99/43353 | 9/1999 |
| WO | WO 99/43356 | 9/1999 |
| WO | WO 00/02870 | 1/2000 |
| WO | WO 01/89564 | 11/2001 |
| WO | WO 02/22820 | 3/2002 |
| WO | WO 02/062810 | 8/2002 |
| WO | WO 03/055876 | 7/2003 |
| WO | WO 03/088980 | 10/2003 |
| WO | WO 03/097658 | 11/2003 |
| WO | WO 2004/004636 | 1/2004 |
| WO | WO 2004/033663 | 4/2004 |
| WO | WO 2004/058304 | 7/2004 |
| WO | WO 2004/094619 | 11/2004 |
| WO | WO 2005/016349 | 2/2005 |
| WO | WO 2005/046597 | 5/2005 |
| WO | WO 2005/051920 | 6/2005 |
| WO | WO 2005/054264 | 6/2005 |
| WO | WO 2005/058934 | 6/2005 |
| WO | WO 2005/085219 | 9/2005 |
| WO | WO 2005/116088 | 12/2005 |
| WO | WO 2006/017180 | 2/2006 |
| WO | WO 2006/022454 | 3/2006 |
| WO | WO 2006/062946 | 6/2006 |
| WO | WO 2006/074426 | 7/2006 |
| WO | WO 2006/074428 | 7/2006 |
| WO | WO 2006/089106 | 8/2006 |
| WO | WO 2006/127906 | 11/2006 |
| WO | WO 2007/021721 | 2/2007 |
| WO | WO 2007/022089 | 2/2007 |
| WO | WO 2007/022385 | 2/2007 |
| WO | WO 2007/028050 | 3/2007 |
| WO | WO 2007/033329 | 3/2007 |
| WO | WO 2008/008852 | 1/2008 |
| WO | WO 2008/008854 | 1/2008 |
| WO | WO 2008/060378 | 5/2008 |
| WO | WO 2008/100453 | 8/2008 |
| WO | WO 2008/109154 | 9/2008 |
| WO | WO 2009/011889 | 1/2009 |
| WO | WO 2009/073911 | 6/2009 |
| WO | WO 2009/073916 | 6/2009 |
| WO | WO 2009/126556 | 10/2009 |
| WO | WO 2009/152245 | 12/2009 |
| WO | WO 2010/126888 | 11/2010 |
| WO | WO 2012/037034 | 3/2012 |
| WO | WO 2012/061662 | 5/2012 |
| WO | WO2012/061662 * | 5/2012 |
| WO | WO 2013/096926 | 6/2013 |

OTHER PUBLICATIONS

Arshad, S. et al., "Primary prevention of asthma and allergy," J. Allergy Clin. Immunol., 116: 3-14 (2005).

Arshad, S. et al., "Primary prevention of asthma and atopy during childhood by allergen avoidance in infacny: a randomised controlled study," Thorax., 58:489-493 (2003).

Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable to Bind to the Self Glycans of gp120," Journal of Virology 82(13):6359-6368, Jul. 2008.

Baeckstrom et al..,"Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.

Banteli et al., "Synthesis of sialyl lewisx mimics. Modifications of the 6-position of galactose," Bioorganic & Medicinal Chemistry Letters, 11(4): 459-462 (2001).

Banteli, R. et al.,"Potent E-Selectin Antagonists," Helvetica Chimica Acta 83(11): 2893-2907, 2000.

Barnes, P. et al., "How do corticosteroids work in asthma?" Ann. Intern. Med., 139: 359-370 (2003).

Bastin, R.. et al,"Salt Selection and Optimisation Procedures for Pharmaceutical New Chemical Entities" Organic Process Research & Development (2000), vol. 4, pp. 427-435.

Belcher, J.D. et al., "Activated monocytes in sickle cell disease: potential role in the activation of vascular endothelium and vaso-occlusion," Blood 96(7):2451-2459, Oct. 1, 2000.

Belcher, J.D. et al., "Inflammatory response in transgenic mouse models of human sickle cell anemia," Blood 96(11)Pt. 1 :600a, Abstract #2574, Nov. 16, 2000.

Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.

Bhaskar, V. et al. "E-selectin Up-regulation Allows for Targeted Drug Delivery in Prostrate Cancer," Cancer Research, 63: 6387-6394 (Oct. 2003).

(56) References Cited

OTHER PUBLICATIONS

Bird and Kimber,"Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978.
Bochner, B. et al., "Glycan array screening reveals a candidate ligand for Siglec-8," Journal of Biological Chemistry, 280(6): 4307-4312 (2005).
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bowen et al., "Characterization of a Human Homologue of the Murine Peripheral Lymph Node Homing Receptor," Journal of Cell Biology, 109:421-427, 1989.
Brandley et al., "Carbohydrate Ligands of LEC Cell Adhesion Molecules," Cell, 63:861-863, 1990.
Bridger, GJ et al. "Synthesis and Structure—Activity Relationships of Phenylenebis(methylene)-Linked Bis-Tetraazamacrocycles That Inhibit HIV Replication. Effects of Macrocyclic Ring Size and Substituents on the Aromatic Linker," J. Med. Chem., 38: 366-378 (1995).
Broquet et al., "Effect of Desipramine on a Glycoprotein Sialyltransferase Activity in C6 Cultured Glioma Cells," J. Neurochem., 54:388-394, 1990.
Calarese, D. A. et al., "Antibody Domain Exchange is and Immunological Solution to Carbohydrate Cluster Recognition," Science 300:2065-2071, Jun. 2003.
Calarese, D. A. et al., "Dissection of the Carbohydrate Specificity of the Broadly Neutralizing Anti-HIV-1 Antibody 2G12," Proceedings of the National Academy of Sciences 102(38):13372-13377, Sep. 2005.
Cao, X. et al., "Defective Lymphoid Development in Mice Lacking Expression of the Common Cytokine Receptor Y Chain," Immunity, 2:223-238, Mar. 1995.
Ceder, O. et al., "On the Absolute Configuration of3-Cyclohexene-1-carboxylic Acid," Acta Chemica Scandivavica, 24(8):2693-2698, 1970.
Chang, J. et al. "GMI-1070, a novel pan-selectin antagonist, reverses acute vascular occlusions in sickle cell mice," Blood, 116(10): 1779-1786 (Sep. 2010).
Chemical Abstracts (STN), Accession No. 1997:584307, Jul. 8, 1997.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Christianson, S.W. et al.,"Enhanced Human CD4+ T Cell Engraftment in β2-Microglobulin-Deficient NOD-scid Mice," The Journal of Immunology, 158:3578-3586 (1997).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Collier, et al., "Membrane translocation by anthrax toxin," Molecular Aspects of Medicine, 30(6): 413-422 (Dec. 1, 2009).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Corson, Timothy W. et al., "Design and Applications of Bifunctional Small Molecules: Why Two Heads Are Better Than One," ACS Chemical Biology 3(11):677-692, Nov. 2008.

Crawford et al., "AMD070, a CXCR4 Chemokine Receptor Antagonist: Practical Large-Scale Laboratory Synthesis," Org. Process Res. Devel. 12:823-830, 2008.
Cumpstey, I. et al. "C2-Symmetrical Thiodigalactoside Bis-Benzamido Derivatives as High-Affinity Inhibitors of Galectin-3: Efficient Lectin Inhibition through Double Arginine—Arene Interactions," Angew Chem., 117:5240-5242 (2005).
DaoudiI, Jean-Michel et al., "New bicyclam-GalCer analogue conjugates: synthesis and in vitro anti-HIV activity," Bioorg. & Med. Chem. Letters 14:495-498, 2004.
Datta and Takayama,"Isolation and purification of trehalose 6-mono- and 6,6'-di-corynomycolates from Cornyebacterium matruchotii. Structural characterization of .sup.1H NMR," Carbohydrate Research 245: 151-158, 1993.
De Clercq, Erik, "The bicyclam AMD3100 story," Nat. Rev. Drug Disc. 2:581-587, Jul. 2003.
Devine: "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Dittmar, Thomas et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz, B.J. et al., "Safe Use of the CSCR4 Inhibitor ALX40-4C in Humans," Aids Research and Human Retroviruses 17(6):475-486, 2001.
Duijvestijn et al.,"High Endothelial Differentiation in Human Lymphoid and Inflammatory Tissues Defined by Monoclonal Antibody HECA-452," Am. J. Path. 130:147-155, 1988.
Dupre, B. et al.,"Glycomimetic Selectin Inhibitors: (.alpha.-D-Mannopyranosyloxy)methylbiphenyls," Bioorganic & Medicinal Chemistry Letters 6(5): 569-572, 1996.
Edgington,"How Sweet It Is: Selectin-Mediating Drugs," Biotechnology 10: 383-389, 1992.
Edwards, W. Barry et al., "Generally Applicable, Convenient Solid-Phase Synthesis and Receptor Affinities of Octreotide Analogs," J. Med. Chem. 37:3749-3757, 1994.
Egberink, H. et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al.,"A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al.,"Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Egger, J. et al. "Nanomolar E-Selectin Antagonists with Prolonged Half-Lives by a Fragment-Based Approach," JACS, 135(26): 9820-9828 (Jul. 2013).
Embury, S.H. et al.,"The contribution of endothelial cell P-selectin to the microvascular flow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for WO 96/20204, published Jul. 4, 1996.
English Translation of JP 06-0306092, dated Nov. 1, 1994.
Ernst and Oehrlein,"Substrate and donor specificity of glycosyl transferases," Glycoconjugate Journal 16: 161-170, 1999.
Ernst B. et al.,"Design and Synthesis of E-Selectin Antagonists," Chimia 55:268-274, 2001.
Ernst, B. et al., "From carbohydrate leads to glycomimetic drugs," Nature Reviews 8:661-677, Aug. 2009.
European Search Report for EP 11010157 dated Mar. 27, 2012.
Faber et al., "The Many Facets of SDF-1a, CXCR4 Agonists and Antagonists on Hematopoietic Progenitor Cells," J. Biomed. & Biotech. Article ID 26065:1-10, 2007.
Feletou, M. et al., "Endothelial dysfunction: a multifaceted disorder," Am. J. Physiol. Heart Circ. Physiol., 291: H985-H1002 (2006).

(56) References Cited

OTHER PUBLICATIONS

Fenderson et al.,"A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al.,"Coordinate Expression of X and Y Haptens during Murine Embryogenesis," Devel. Biol. 114:12-21, 1986.
Fenderson et al.,"The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Frison, N. et al., "Oligolysine-Based Oligosaccharide Clusters: Selective Recognition and Endocytosis by the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fukushi et al.,"Novel Fucolipids Accumulating in Human Adenocarcinoma," J. Biol. Chem. 259(16):10511-10517 (1984).
Fukushi et al.,"Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al.,"Endogenous Tumor Lectins: Overview and Perspectives," Anticancer Res. 6:573-578, 1986.
Gais, H.-J. et al.,"Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al.,"A cell-surface molecule involved in organ-specific homing of lymphocyctes," Nature 304:30-34, 1983.
Garber, N. et al., "On the specificity of the D-galactose-binding lectin (PA-I) of *Pseudomonas aeruginosa* and its strong binding to hydrophobic derivatives of D-galactose and thiogalactose," Biochimica et Biophysica Acta, 1116:331-333 (1992).
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vi): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree *Erythrina corallodendron*. Comparison with Glycine max (soybean) and *Pseudomonas aeruginosa* lectins," Canadian Journal of Biochemistry, 59(5):315-320 (1981).
Goodman and Gillman's, "Pharmacological Basis of Therapeutics," 10th edition, p. 54 (2001).
Gooi et al.,"Stage-specific embryonic antigen involves alpha 1-3 fucosylated type 2 blood group chains," Nature 292:156-158, 1981.
Hakomori et al.,"Novel Fucolipids Accumulating in Human Adenocarcinoma. I. Glycolipids With Di- or Trifucosylated Type 2 Chain," J. Biol. Chem. 259(7):4672-4680, 1984.
Hakomori et al.,"The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Hakomori S.,"Aberrant Glycosylation in Cancer Cell Membranes as Focused on Glycolipids: Overview and Perspectives," Cancer Res. 45:2405-2414, 1985.
Halloran, M. et al., "Ley/H: An endothelial-selective cytokine-inducible angiogenic mediator," Journal of Immunology, 164(9): 4868-4877 (May 1, 2000).
Handa et al.,"Selectin GMP-140 (CD62; PADGEM) Binds to Sialosyl-Le.sup.A and Sialosyl-Le.sup.x, and Sulfated Glycans Modulate this Binding," Biochemical and Biophysical Research Communication 181(3):1223-1230, 1991.
Hansson and Zopf,"Biosynthesis of the Cancer-associated Sialyl-Le.sup.a Antigen," Journal of Biological Chemistry 260(16):9388-9392, 1985.
Harlan, J.M.,"Introduction-anti-adhesion therapy in sickle cell disease," Blood 95:365-367, 2000.
Hasegawa et al.,"Synthesis of deoxy-L-fucose-containing sialyl Lewis X ganglioside analogues," Carbohydrate Research 257: 67-80, 1994.
Hasegawa et al.,"Synthesis of sialyl Lewis X ganglioside analogues containing modified L-fucose residues," Carbohydrate Research 274: 165-181, 1995.
Hebbel, P.R.,"Blockade of Adhesion of Sickle Cells to Endothelium by Monoclonal Antibodies," The New England Journal of Medicine 342:1910-1912, Jun. 22, 2000.
Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.
Hilal et al.,"Electronic structure of orotic acid I. Geometry, conformational preference and tautomerism:, Journal of Molecular Structure (Theochem)" 685 (2004) 35-42.
Hilgenbrink, A. et al., "Folate receptor-mediated drug targeting: from therapeutics to diagnostics," J. Pharm. Sci., 94(10): 2135-2146 (2005).
Holgate, ST et al., "Epithelium dysfunction in asthma," Current Reviews of Allergy and Clinical Immunology, 120: 1233-1234 (2007).
Holmes et al.,"Enzymatic Basis for the Accumulation of Glycolipids with X and Dimeric X Determinants in Human Lung Cancer Cells (NCI-H69)," J. Biol. Chem. 260(12):7619-7627, 1985.
Hong, P. W.-P. et al., "Identification of the Optimal DC-SIGN Binding Site on Human Immunodeficiency Virus Type 1 gp120," Journal of Virology 18(15):8325-8336, Aug. 2007.
Huse et al.,"Generation of a Large Combinatorial Library of the Immunoglobulin Repertoire in Phage Lambda," Science 246:1275-1281, 1989.
Huwe, C. M. et al.,"Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.
Hynes, R.,"Integrins: A Family of Cell Surface Receptors," Cell 48:549-554, 1987.
Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.
International Search Report for PCT/US2003/19429 dated Dec. 18, 2003.
International Search Report for PCT/US2003/40881 dated Apr. 26, 2004.
International Search Report for PCT/US2004/038782 dated Jun. 3, 2005.
International Search Report for PCT/US2004/038783 dated May 31, 2005.
International Search Report for PCT/US2006/020249 dated Sep. 27, 2006.
International Search Report for PCT/US2006/030993 dated Feb. 22, 2007.
International Search Report for PCT/US2007/012867 dated Nov. 16, 2007.
International Search Report for PCT/US2007/014457 dated Jul. 15, 2008.
International Search Report for PCT/US2007/021541 dated Jul. 18, 2008.
International Search Report for PCT/US2008/001762 dated Jun. 17, 2008.
International Search Report for PCT/US2010/032568 dated Jul. 30, 2010.
International Search Report for PCT/US2011/031428 dated Jun. 30, 2011.
International Search Report for PCT/US2011/059243 dated Feb. 20, 2012.
International Search Report for PCT/US2012/071519 dated Mar. 8, 2013.
International Search Report for PCT/US2013/067711 dated Jun. 2, 2014.

(56) References Cited

OTHER PUBLICATIONS

Inwald, D. P. et al.,"Platelet and leucocyte activation in childhood sickle cell disease: association with nocturnal hypoxaemia," British Journal of Haematologyl 11:474-481, Nov. 2000.
Ishikawa, F. et al., "Chemotherapy-resistant human AML stem cells home to and engraft within the bone-marrow endosteal region," Nature Biotechnology 25(11):1315-1321, Nov. 2007.
Issekutz, T.,"Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al.,"Differentiation-dependent Expression of I and Siaiyl I Antigens in the Developing Lung of Human Embryos and in Lung Cancers," Cancer Research 50: 7603-7611, 1990.
Jeffrey et al.,"Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al.,"Inhibition of Human Immunodeficiency Virus Type I Reverse Transcriptase by Suramin-related Compounds," The Journal of General Virology 68(8): 2183-2192, 1987.
Jentsch, TJ et al. "Ion Channels: Function Unravelled by Dysfunction," Nature Cell Biology, 6(11): 1039-1047 (Nov. 2004).
Kaila, N. et al.,"Design and synthesis of sialyl Lewis(x) mimics as E- and P-selectin inhibitors," Med Res Rev 22(6):566-601, Nov. 2002.
Kaila, N. et al.,"8-C-Mannosides as Selectin Inhibitors," Journal of Medicinal Chemistry 45(8): 1563-1566, 2002.
Kannagi et al.,"New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al.,"Stage-specific embryonic antigens (SSEA-3 and -4) are epitopes of a unique globo-series ganglioside isolated from human teratocarcinoma cells," Embo J. 2(12):2355-2361, 1983.
Kannagi, R. et al. "Carbohydrate-mediated cell adhesion in cancer metastasis and angiogenesis," Cancer Sci., 95(5): 377-384 (2004).
Kansas, G., "Selectins and Their Ligands: Current Concepts and Controversies," Blood, 88(9): 3259-3287 (1996).
Karaivanova et al.,"Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Kaul, D.K. et al.,"Hypoxia/reoxygenation causes inflammatory response in transgenic sickle mice but not in normal mice," The Journal of Clinical Investigation 106(3):411-420, Aug. 2000.
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al.,"Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al.,"Immunoaffinity Isolation of a Sialyl-Le.sup.a Oligosaccharide from Human Milk," J. Biochem. 104:591-594, 1988.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of *Pseudomonas aeruginosa* by Receptor Blocking Carbohydrates," Infection, 15(4): 21-24 (1987).
Koch, Alisa E et al., "Angiogenesis mediated by soluble forms of E-selectin and vascular cell adhesion molecule-1," Nature, 376(6540): 517-519 (1995).
Kogan, T.P. et al.,"Novel Synthetic Inhibitors of Selectin-Mediated Cell Adhesion: Synthesis of 1,6-Bis[3-(3- carboxymethylphenyl)-r-(2-.alpha.-.sub.D-monnopyranosyloxy)p-henyl]hexane (TBC1269)," J Med. Chem 41:1099-1111, 1998.
Kogan, T.P. et al.,"Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kogan, T.P. et al.,"Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kohler and Milstein,"Continuous cultures of fused cells secreting antibody of predefined specificity," Nature 256:495-497, 1975.
Kohler and Milstein,"Derivation of specific antibody-producing tissue culture and tumor lines by cell fusion," Eur. J. Immunol. 6:511-519, 1976.
Kojima and Hakomori,"Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb, H. C. et al.,"Development of Tool for the Design of Selectin Antagonists," Chem. Eur. J. 3(10):1571-1578, 1997.
Kolb, H. C. et al.,"Recent progress in the glycodrug area," Pure & Applied Chemistry 69(9):1879-1884, 1997.
Koprowski et al.,"Colorectal Carcinoma Antigens Detected by Hybridoma Antibodies," Somatic Cell Genetics 5(6):957-972, 1979.
Kuzuoka,"Antitumor activity of murine monoclonal antibody NCC-ST-421," Chem. Ab. 115:27344v, 1991.
Kwiatkowski et al.,"Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Lamblin et al.,"Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-1, to glycosphingolipids and other glycoconjugates," Glycoconjugate Journal, 11:292-298 (1994).
Larsen et al., Padgem-Dependent Adhesion of Platelets to Monocytes and Neutrophils is Mediated by a Lineage-Specific Carbohydrate, LNF III (CD15), Cell 63:467-474, 1990.
Lee et al.,"A new method of sequencing linear oligosaccharides on gels using charged, fluorescent coniugates" Carbohydrate Research, vol. 214, 1991, pp. 155-168, XP000226749.
Leppla, S H et al., "Anthrax Toxin Fusion Proteins for Intracellular Delivery of Macromolecules," Journal of Applied Microbiology., 87(2): p. 284 (Aug. 1, 1999).
Ley, K. "The role of selectins in inflammation and disease," Trends in Molecular Medicine, 9(6): 263-268 (Jun. 2003).
Ley, K. et al. "Selectins in T-cell Recruitment to Non-Lymphoid Tissues and Sites of Inflammation," Nature Reviews, 4: 1-11 (May 2004).
Li, B., et al.,"Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.
Lindenberg et al.,"Carbohydrate binding properties of mouse embryos," J. Reprod. Fert. 89:431-439, 1990.
Lipartiti et al.,"Monosialoganglioside GM1 Reduces NMDA Neurotoxicity in Neonatal Rat Brain," Experimental Neurology 113:301-305, 1991.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al.,"A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al.,"ELAM-1-Dependent Cell Adhesion to Vascular Endothelium Determined by a Transfected Human Fucosyltransferase cDNA," Cell 63:475-484, 1990.

(56) References Cited

OTHER PUBLICATIONS

Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.

Macher et al.,"A Novel Carbohydrate, Differentiation Antigen on Fucogangliosides of Human Myeloid Cells Recognized by Monoclonal Anitbody VIM-2," Journal of Biological Chemistry 257(23):14365-14369, 1982.

Magnani et al.,"A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.

Magnani et al.,"Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani, J.,"Carbohydrate Sequences Detected by Murine Monoclonal Antibodies," Chemistry and Physics of Lipids 42:65-74, 1986.

Magnani, J.,"Potent Glycomimetic Inhibitors of the Adhesion Molecule, PA-IIL, for the Bacterial Pathogen, *Pseudomonas auroginosa*," Glycobiology 13(11): 854, Abstract No. 104, Oct. 2003.

Mann, AP et al. "Identification of Thioaptamer Ligand against E-Selectin: Potential Application for Inflamed Vasculature Targeting," PLoS ONE, 5(9): 1-11 (Sep. 2010).

Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.

Matsui, N. M. et al.,"Heparin inhibits the flow adhesion of sickle red blood cells to Pselectin," Blood 100(10):3790-3796, Nov. 15, 2002.

Matsui, N. M. et al.,"The Novel Adhesion of Erythrocytes to P-Selectin in Sickle Cell Disease," Blood 96(11) Pt. 1:600a, Abstract #2575, Nov. 16, 2000.

Matsui, N. M.et al.,"P-selectin mediates the adhesion of sickle erythrocytes to the endothelium," Blood 98(6):1955-1962, Sep. 15, 2001.

Menendez, A., et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.

Moore, P. L. et al., "Evolution of an HIV Glycan-Dependent Broadly Neutralizing Antibody Epitope Through Immune Escape," Nature Medicine doi:10.1038/nm.2985 pp. 1-6, Oct. 2012.

Mosley et al., "Recent Patents Regarding the Discovery of Small Molecule CXCR4 Antagonists," Expert Opin. Ther. Patents 19(1):23-38, 2009.

Mulligan and Berg,"Selection for animal cells that express the *Escherichia coli* gene coding for xanthine-gunine phosphoribosyltransferase," Proc. Natl. Acad. Sci. USA 78:2072-2076, 1981.

Nagel, R. L.,"A Knockout of a Transgenic Mouse-Animal Models of Sickle Cell Anemia," The New England Journal of Medicine 339:194-195, Jul. 16, 1998.

Narita, T. et al. "Corticosteroids and medroxyprogesterone acetate inhibit the induction of breast cancer cells," Anticancer Research, 15(6B): 2523-2527 (1995)—Abstract.

Narum, Tetsuo et al., "Synthesis and Biological Evaluation of Selective CXCR4 Antagonists Containing Alkene Dipeptide Isosteres," Organic & Biomolecular Chemistry, 8(3): 616-621(Feb. 7, 2010).

Natarajan, M.M. et al.,"Adhesion of sickle red blood cells and damage to interleukinIbeta stimulated endothelial cells under flow in vitro," Blood 87:4845-4852, 1996.

Nguyen, M et al., "Novel synthetic analogs 1-29 of sialyl Lewis X can inhibit angiogenesis in vitro and in vivo," Biochemical and Biophysical Research Communications, 228(3): 716-723 (Nov. 21, 1996).

Nicolaou et al.,"Total Synthesis of the Tumor-Associated Le.sup.x Family of Glycosphingolipids," J. Amer. Chem. Soc. 112:3693-3695, 1990.

Noguchi, M. et al. "A minor E-selectin ligand, CD65, is critical for extravascular infiltration of acute myeloid leukemia cells," Leukemia Research, 25: 847-853 (2001).

Norman et al., "Sialyl Lewisx(sLex) and an sLex Mimetic, CGP69669A, Disrupt E-Selectin-Dependent Leukocyte Rolling In Vivo," Blood , 91(2):475-483 (Jan. 15, 1998).

Notice of Allowance mailed Dec. 11, 2008 in U.S. Appl. No. 11/501,464.

Notice of Allowance mailed Dec. 3, 2012 in U.S. Appl. No. 12/768,173.

Notice of Allowance mailed Feb. 9, 2011 in U.S. Appl. No. 11/973,891.

Notice of Allowance mailed May 25, 2011 in U.S. Appl. No. 12/069,436.

Notice of Allowance mailed May 9, 2012 in U.S. Appl. No. 12/370,826.

Nudelman et al.,"Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.

Nutku, E. et al., "Ligation of Siglec-8: a selective mechanism for induction of human eosinophil apoptosis," Blood, 101(12): 5014-5020 (2003).

Obermajer, N. et al., "Design, synthesis and activity evaluation of mannose-based DC-SIGN antagonists," Molecular Diversity 15:347-360, May 2011.

Office Action Mailed Apr. 5, 2012 in U.S. Appl. No. 12/418,774.
Office Action mailed Apr. 8, 2010 in U.S. Appl. No. 11/973,891.
Office Action mailed Apr. 8, 2013 in U.S. Appl. No. 13/566,522.
Office Action mailed Aug. 13, 2008 in U.S. Appl. No. 10/992,238.
Office Action mailed Aug. 8, 2006 in U.S. Appl. No. 10/601,080.
Office Action mailed Feb. 11, 2013 in U.S. Appl. No. 13/566,522.
Office Action mailed Feb. 23, 2006 in U.S. Appl. No. 10/742,631.
Office Action mailed Feb. 23, 2011 in U.S. Appl. No. 11/973,891.
Office Action mailed Feb. 23, 2012 in U.S. Appl. No. 12/370,826.
Office Action mailed Feb. 6, 2008 in U.S. Appl. No. 10/992,238.
Office Action mailed Feb. 6, 2014 in U.S. Appl. No. 14/057,729 (Reissue Application of U.S. Pat. No. 8,039,442).
Office Action mailed Jan. 31, 2014 in U.S. Appl. No. 12/418,774.
Office Action mailed Jul. 14, 2010 in U.S. Appl. No. 12/069,436.
Office Action mailed Jul. 16, 2014 in U.S. Appl. No. 13/877,633.
Office Action mailed Jul. 8, 2011 in U.S. Appl. No. 12/370,826.
Office Action mailed Jun. 14, 2007 in U.S. Appl. No. 10/992,480.
Office Action mailed Jun. 19, 2012 in U.S. Appl. No. 12/768,173.
Office Action mailed Jun. 2, 2006 in U.S. Appl. No. 10/601,080.
Office Action mailed Jun. 20, 2013 in U.S. Appl. No. 13/224,847.
Office Action mailed Jun. 23, 2010 in U.S. Appl. No. 11/920,499.
Office Action mailed Jun. 6, 2005 in U.S. Appl. No. 10/742,631.
Office Action mailed Mar. 18, 2013 in U.S. Appl. No. 13/224,847.
Office Action mailed Mar. 20, 2013 in U.S. Appl. No. 13/081,068.
Office Action mailed Mar. 25, 2011 in U.S. Appl. No. 12/370,826.
Office Action mailed May 10, 2011 in U.S. Appl. No. 12/302,092.
Office Action mailed May 15, 2013 in U.S. Appl. No. 13/081,068.
Office Action mailed May 25, 2011 in U.S. Appl. No. 12/304,879.
Office Action mailed May 28, 2008 in U.S. Appl. No. 11/501,464.
Office Action mailed May 8, 2014 in U.S. Appl. No. 13/822,573.
Office Action mailed Nov. 2, 2005 in U.S. Appl. No. 10/742,631.
Office Action mailed Nov. 25, 2011 in U.S. Appl. No. 13/093,611.
Office Action mailed Oct. 13, 2010 in U.S. Appl. No. 11/920,499.
Office Action mailed Oct. 13, 2011 in U.S. Appl. No. 12/418,774.
Office Action mailed Oct. 29, 2010 in U.S. Appl. No. 12/069,436.
Office Action mailed Sep. 12, 2008 in U.S. Appl. No. 11/501,464.
Office Action mailed Sep. 20, 2010 in U.S. Appl. No. 11/973,891.
Office Action mailed Sep. 25, 2007 in U.S. Appl. No. 10/992,238.
Office Action mailed Sep. 27, 2011 in U.S. Appl. No. 12/304,879.

Orhlein, R.,"Carbohydrates and Derivatives as Potential Drug Candidates with Emphasis on the Selectin and Linear-B Area," Mini Reviews in Medicinal Chemistry 1: 349-361, 2001.

Oxford Textbook of Oncology, vol. 1, published 1995 by Oxford University Press, pp. 447-453.

Palcic et al.,"A Bisubstrate Analog Inhibitor for .alpha.(1.fwdarw.2)-Fucosyltransferase," J. Biol. Chem. 264:17174-17181, 1989.

(56) References Cited

OTHER PUBLICATIONS

Palcic et al.,"Enzymic Synthesis of Oligosaccharides Terminating in the Tumor-Associated Sialyl-Lewis-a Determinant," Carbohydr. Res. 190:1-11, 1989.

Palcic et al.,"Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.

Palma-Vargas, J.M. et al.,"Small-Molecule Selectin Inhibitor Protects Against Liver Inflammatory Response After Ischemia and Reperfusion," J. Am. Coll. Surg. 185: 365-372, 1997.

Patton, J. T. et al.,"GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.

Payre, et al.,"Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.

Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).

Pejchal R. et al., "A Potent and Broad Neutralizing Antibody Recognizes and Penetrates the HIV Glycan Shield," Science 334:1097-1103, Nov. 2011.

Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).

Pentelute, Brad L. et al., "Chemica 1 1-16 dissection of protein translocation through the anthrax toxin pore," Angewandte Chemie, 50(10): 2294-2296 (Mar. 1, 2011).

Perret, S. et al.,"Structural basis for the interaction between human milk oligosaccharides and the bacterial lectin PA-IIL of *Pseudomonas aeruginosa*," Biochem. J. 389: 325-332, 2005.

Phillips et al.,"ELAM-1 Mediates Cell Adhesion by Recognition of a Carbohydrate Ligand, Sialyl-Le.sup.x," Science 250:1130-1132, 1990.

Picker er al.,"The Neutrophil Selectin LECAM-1 Presents Carbohydrate Ligands to the Vascular Selectins ELAM-1 and GMP-140," Cell 66:921-933, 1991.

Prokazova et al., "Sialylated lactosylceramides. Possible inducers of non-specific immunosuppression and atherosclerotic lesions," European Journal of Biochemistry 172:1-6, 1988.

Purton, L. E. et al., "Limiting Factors in Murine Hematopoietic Stem Cell Assays," Cell Stem Cell 1: 263-270, Sep. 2007.

Rapoport, E. et al., "Probing Sialic Acid Binding Ig-Like Lectins (Siglecs) with Sulfated Oligosaccharides," Biochemistry (Moscow), 71(5): 496-504 (2006).

Rauvala et al.,"Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.

Reina, J. J. et al., "1,2-Mannobioside Mimic: Synthesis, DC-SIGN Interaction by NMR and Docking, and Antiviral Activity," ChemMedChem 2:1030-1036, 2007.

Rice and Bevilacqua,"An Inducible Endothelial Cell Surface Glycoprotein Mediates Melanoma Adhesion," Science 246:1303-1306, 1989.

Richert et al., "Inhibition of CXCR4 by CTCE-9908 Inhibits Breast Cancer Metastasis to Lung and Bone," Oncology Reports 21:761-767, 2009.

Ruoslahti and Pierschbacher,"New Perspectives in Cell Adhesion: RGD and Integrins," Science 238:491-497, 1987.

Sakurai et al.,"Selection of a Monoclonal Antibody Reactive with a High-Molecular-Weight Glycoprotein Circulating in the Body Fluid of Gastrointestinal Cancer Patients," Cancer Research 48:4053-4058, 1988.

Sastry et al.,"Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.

Scanlan, C. N. et al., "Exploiting the Defensive Sugars of HIV-1 for Drug and Vaccine Design," Nature 446:1038-1045, Apr. 2007.

Scanlan, C. N. et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.

Scharfman, A. et al.,"*Pseudomonas aeruginosa* binds to neoglycoconjugates bearing mucin carbohydrate determinants and predominantly to sialyl-Lewis x conjugates," Glycobiology 9(8): 757-764, 1999.

Scharfman, A. et al.,"Recognition of Lewis x Derivatives Present on Mucins by Flagellar Components of *Pseudomonas aeruginosa*," Infection and Immunity 69(9): 5243-5248, Sep. 2001.

Schief, W. R. et al., "Challenges for Structure-Based HIV Vaccine Design," Current Opinion in HIV and AIDS 4:431-440, 2009.

Schwizer, D. et al. "Pre-organization of the Core Structure of E-Selectin Antagonist," Chemistry—A European Journal, 18(5): 1342-1351 (Jan. 2012).

Shan, M. et al., "HIV-1 gp120 Mannoses Induce Immunosuppressive Responses from Dendritic Cells," PLoS Pathogens 3(11):e169 1637-1650, Nov. 2007.

Shitara et al.,"Application of Anti-Sialyl Le.sup.a Monoclonal antibody, KM231, for Immunotherapy of Cancer," Anticancer Res. 11:2003-2014, 1991.

Simanek Eric A. et al. "Selectin-carbohydrate interactions: from natural ligands to designed mimics", Chemical Reviews vol. 98, No. 2, pp. 833-862, Jan. 1998.

Singh et al., "Evaluation of a CXCR4 Antagonist in a Xenograft Mouse Model of Inflammatory Breast Cancer," Clin. Exp. Metastasis 27:233-240, Mar. 2010.

Sipkins, Dorothy A. et al., "In Vivo Imaging of Specialized Bone Marrow Endothelial Microdomains for Tumor Engraftment," Nature Pub. Group GB 435 (7044):969-973, Jun. 2005.

Siuzdak et al.,"Examination of the Sialyl Lewis X—Calcium Complex by Electrospray Mass Spectrometry," Bioorganic & Medicinal Chemistry Letters 4(24): 2863-2866, 1994.

Solovey et al.,"Circulating Activated Endothelial Cells in Sickle Cell Anemia," The New England Journal of Medicine 337:1584-1590, Nov. 27, 1997.

Solovey, AA et al. "Modulation of endothelial cell activation in sickle cell disease: a pilot study," Blood, 97(7): 1937-1941 (Apr. 2001).

Sprengard, U. et al.,"Synthesis and Biological Activity of Novel Sialyl-Lewis.sup.X Conjugates," Bioorganic & Medicinal Chemistry Letters 6(5): 509-514, 1996.

Stanley and Atkinson,"The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.

Stephens and Cockett,"The construction of highly efficient and versatile set of mammalian expression vectors," Nucleic Acids Research. 17:7110, 1989.

Stevenson, J. et al.,"Differential metastasis inhibition by clinically relevant levels of heparins," Clin. Cancer Res. 11(19): 7003-7011 (2005).

Streeter et al.,"Immunohistologic and Functional Characterization of a Vascular Addressin Involved in Lymphocyte Homing into Peripheral Lymph Nodes," Journal of Cell Biology 107: 1853-1862, 1988.

Stroud et al.,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.

Supplementary European Search Report in EP 03739223 dated Jan. 16, 2009.

Suzuma, I. et al. "Contribution of E-Selectin to Cellular Infiltration during Endotoxin-Induced Uveitis," Invest. Ophthalmol. Vis. Sci., 39: 1620-1630 (1998).

Svenson and Lindberg,"Coupling of Acid Labile *Salmonella* Specific Oligosaccharides to Macromolecular Carriers," J. Immunol. Meth. 25:323-335, 1979.

(56) References Cited

OTHER PUBLICATIONS

Symon, FA et al. "Selectins and their Counter receptors: a bitter sweet attraction," Thorax, 51: 1155-1157 (1996).
Tabarani G. et al., "Mannose Hyperbranched Dendritic Polymers Interact with Clustered Organization of DC-SGIN and Inhibit gp120 Binding," FEBS Letters 580:2402-2408, Mar. 2006.
Takada et al.,"Adhesion of Human Cancer Cells to Vascular Endothelium Mediated by a Carbohydrate Antigen, Sialyl Lewis A.sup.1," Biochem. Biophys. Res. Commun. 179(2):713-719, 1991.
Takahashi, Takashi et al., "Design and Synthesis of a Water-Soluble Taxol Analogue : Taxol-Sialyl Conjugate," Bioorg. & Med. Chem. Letters 8:113-116, 1998.
Takeichi, M.,"Cadherins: a molecular family essential for selective cell-cell adhesion and animal morphogenesis," Trends Genet. 3(8):213-217, 1987.
Tamamura, H. et al. "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka, T. et al. "Azamacrocyclic Metal Complexes as CXCR4 Antagonists," ChemMedChem, 6: 834-839 (2011).
Tedder, TF et al. "The selectins: vascular adhesion molecules," FASEB J, 9(10): 866-73 (1995).
The Merck Manual of Diagnosis and Therapy, Seventeenth Edition, published 1999 by Merck Research Laboratories, pp. 397, 398, 948,949, 1916, 1979-1981.
Thoma G. et al.,"A readily Available, Highly Potent E-Selectin Antagonist," Angew. Chem. Int. Ed. 40(19): 3644-3647, 2001.
Thoma, G et al., "Nanomolar E-selectin inhibitors: 700-fold potentiation of affinity by multivalent ligand presentation," Journal of the American Chemical Society, 123(41): 10113-10114 (Oct. 17, 2001).
Thoma, G. et al.,"Preorganization of the Bioactive Conformation of Sialyl Lewis.sup.X Analogues Correlates with Their Affinity to E-Selectin," Angew. Chem. Int. Ed. 40(10): 1941-1945, 2001.
Thoma, G. et al.,"Synthesis and biological evaluation of a potent E-selectin antagonist," J. Med. Chem. 42 (23): 4909-4913, Nov. 18, 1999.
Thoma, G. et al.,"Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G.,"Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz, A. et al., "Probing the carbohydrate recognition domain of E-selectin: The importance of the acid orientation in sLex mimetics," Bioorg. Med. Chem., 18(1): 19-27 (2010).
Toepfer, et al., "Synthesis of novel mimetics of the sialyl Lewis X determinant," Tetrahedron Letter, 36(50): 9161-9164 (1995).
Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trouet et al.,"A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al.,"Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements for the carbohydrate ligand of E-selectin," PNAS, 88: 10372-10376 (Nov. 1991).
U.S. Appl. No. 10/601,080, filed Jun. 19, 2003.
U.S. Appl. No. 10/742,631, filed Dec. 19, 2003.
U.S. Appl. No. 10/992,238, filed Nov. 18, 2004.
U.S. Appl. No. 11/920,499, filed Nov. 16, 2007.
U.S. Appl. No. 12/302,092, filed Nov. 24, 2008.
U.S. Appl. No. 12/304,879, filed Dec. 15, 2008.
U.S. Appl. No. 12/418,774, filed Apr. 6, 2009.
U.S. Appl. No. 13/081,068, filed Nov. 15, 2013.
U.S. Appl. No. 13/093,611, filed Apr. 25, 2011.
U.S. Appl. No. 13/224,847, filed Sep. 2, 2011.
U.S. Appl. No. 13/566,522, filed Aug. 3, 2012.
U.S. Appl. No. 13/785,439, filed Mar. 5, 2013.
U.S. Appl. No. 13/822,573, filed Mar. 12, 2013.
U.S. Appl. No. 13/877,633, filed Jun. 17, 2013.
U.S. Appl. No. 14/057,729, filed Oct. 18, 2013 (Re-Issue Application of U.S. Pat. No. 8,039,442).
U.S. Appl. No. 14/080,926, filed Nov. 15, 2013.
U.S. Appl. No. 14/106,662, filed Dec. 13, 2013.
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Venkataraman, Nitya, et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Waldmann, H. et al.,"Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walker, L. M. et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, GM. "Novel Therapies for Asthma—Advances and Problems," Current Pharmaceutical Design, 11(23): 3027-3038 (2005).
Walz et al.,"Recognition by ELAM-1 of the Sialyl-Le.sup.X Determinant on Myeloid and Tumor Cells," Science 250:1132-1135, 1990.
Wang, L.X. et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang, S.K. et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.
Wang, Y. et al. "Effect of ginsenoside rg1 and rh1 on the expression of hla-dr, cd25, cd44, cd1 1c and e-selectin on dendritic cell,"Zhongguo Mianyixue Zazhi, 23(1): 46-48 (2007)—Abstract.
Ward and Mulligan,"Blocking of adhesion molecules in vivo as anti-inflammatory therapy," Immunology 1: 165-171, 1994.
Wesche, Jorgen et al., "Characterization of membrane translocation by anthrax protective antigen," Biochemistry, 37(45): 15737-15746 (Nov. 10, 1998).
Whisler and Yates,"Regulation of Lymphocyte Responses by Human Gangliosides. I. Characteristics of Inhibitory Effects and the Induction of Impaired Activation," Journal of Immunology 125(5):2106-2111, 1980.
Winnard, P. et al., "Real time non-invasive imaging of receptor-ligand interactions in vivo," J. Cell. Biochem., 90: 454-463 (2003).
Winzer, K. et al. "The *Pseudomonas aeruginosa* Lectins PA-IL and PA-IIL are Controlled by Quorom Sensing and by RpoS," J. Bacteriol. 182(22): 6401-6411 (2000).
Wu, B. et al. "Structures of the CXCR4 Chemokine GPCR with Small-Molecule and Cyclic Peptide Antagonists," Science, 330(6007): 1066-1071 (Nov. 2010).
Xu, J. et al., "Molecular insights and therapeutic targets for diabetic endothelial dysfunction," Circulation, 120: 1266-1286 (2009).
Yamazaki, F. et al,."Synthesis of an appropriately protected core glycotetraoside, a key intermediate for the synthesis of 'bisected' complex-type glycans of a glycoprotein," Carbohydrate Research 201: 15-30, 1990.

(56) References Cited

OTHER PUBLICATIONS

Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zheng, CX et al. "The prognostic value of preoperative serum levels of CEA, CA19-9 and CA72-4 in patients with colorectal cancer," World J. Gastroentero, 7(3): 431-434 (2001).
Zhou et al.,"The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al.,"Affinity Purification of Antibodies Using Oligosaccharide-Phenethylamine Derivatives Coupled to Sepharose," Meth. Enzymol. 50:171-175, 1978.
Aggoune et al., "The Vascular Niche Is Involved in Regulating Leukemic Stem Cells in Murine Chronic Myelogenous Leukemia" Blood, 124(21):516, Dec. 6, 2014.
Azab et al, "Role of Selectins in the Pathogenesis of Multiple Myeloma", ASCO Annual Meeting 2009, Poster #11103, May 2009.
Azab et al., "P-selectin Glycoprotein Ligand Regulates the Interaction of Multiple Myeloma Cells with the Bone Marrow Microenvironment", Blood, 119:1468-1478, Nov. 16, 2011.
Azab et al., "Role of Selectins in the Pathogenesis of Multiple Myeloma", J Clin Oncol, 27(15s):absrt 11103, 2009.
Barasch et al., "Palifermin for Management of Treatment-Induced Oral Mucositis in Cancer Patients", Biologics: Targets & Therapy, 3:111-116, 2009.
Chang et al., "Effects of Pan-Selectin Antagonist GMI-1070 on the Treatment of Vaso-Occlusion in Sickle Cell Mice", Blood, 112(11), Abstract #535, Nov. 2008.
Chase et al., "E-Selectin Ligands as Mechanosensitive Receptors on Neutrophils in Health and Disease", Annals of Biomedical Engineering, DOI:10.1007/s10439-011-0507-y, Jan. 24, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", Blood, 120(21), Abstract #4092, Nov. 16, 2012.
Chien et al., "A Novel Small Molecule E-Selectin Inhibitor GMI-1271 Blocks Adhesion of AML Blasts to E-Selectin and Mobilizes Blood Cells in Nodscid IL2Rgc-/- Mice Engrafted with Human AML", 2012 ASH Annual Meeting, Poster #54715, Dec. 10, 2012.
Chien et al., "Adhesion of Acute Myeloid Leukemia Blasts to E-Selectin in the Vascular Niche Enhances Their Survival by Mechanisms Such as Wnt Activation", Blood, 122(21):61, Nov. 15, 2013.
Chien et al., "Novel Dual E-Selectin-CXCR4 Inhibitors Mobilize Human Acute Myeloid Leukemia (AML) Cells in the NODscid IL2R{gamma}c-/- Xenograft and Confer Susceptibility to Cytarabine", Blood, 118(21), Abstract #579, Nov. 18, 2011.
Decastro et al., "Effects of GMI-1070, a Pan-Selectin Inhibitor, on Pain Intensity and Opioid Utilization in Sickle Cell Disease", Blood, 122(21):775, Nov. 15, 2013.
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.

Esposito et al., "Exploration of a Potent E-selectin Antagonist (GMI-1271) as a Potential Therapeutic for Treating Breast Cancer Metastasis to the Lung and Bone", Cancer Res, Abstract #4039, Oct. 1, 2014.
European Search Report for EP 2249854 dated Feb. 18, 2009.
Flanner et al., "Comparison of Predicted GMI-1070 Human Intravenous Pharmacokinetics from in silico PBPK and Allometric Scaling Models", AAPS Annual Meeting, Poster, Nov. 2009.
Flanner et al., "Comparison of Predicted GMI-1070 Human Intravenous Pharmacokinetics from in silico PBPK and Allometric Scaling Models", AAPS Annual Meeting, Abstract, Nov. 2009.
International Search Report for PCT/US2013/067705 dated Dec. 10, 2013.
International Search Report for PCT/US2014/021142 dated Mar. 6, 2014.
International Search Report for PCT/US2014/57978 dated Dec. 14, 2014.
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "The Discovery, Biology, and Drug Development of Sialyl $Le^a$ and Sialyl $Le^x$", Archives of Biochemistry and Biophysics, 426:122-131, May 8, 2004.
McCavit et al., "An Analysis of the Pediatric Sub-Group From the Phase 2 Study of GMI-1070—A Novel Agent for the Vaso-Occlusive Crisis of Sickle Cell Anemia", Blood, 122(21):2206, Nov. 15, 2013.
McCavit et al., "An Analysis of the Pediatric Sub-Group From the Phase 2 Study of GMI-1070—A Novel Agent for the Vaso-Occlusive Crisis of Sickle Cell Anemia", ASH Annual Meeting 2013, Poster #56448, Dec. 8, 2013.
Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.
Myers et al., "Novel E-Selectin Antagonist GMI-1271 Decreases Venous Thrombosis without Increased Bleeding Potential in a Mouse Model", ASH Annual Meeting 2012, Poster #53444, Dec. 10, 2012.
Myers et al., "Pan-Selectin Antagonist, GMI-1070 Decreases Venous Thrombosis in a Mouse Model", Blood, 118, Abstract #3273, Nov. 2011.
Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.
Notice of Allowance mailed Aug. 28, 2014 in U.S. Appl. No. 13/822,573.
Office Action mailed Feb. 3, 2015 in U.S. Appl. No. 13/877,633.
Office Action mailed Feb. 4, 2013 in U.S. Appl. No. 12/747,324.
Office Action mailed Jan. 27, 2014 in U.S. Appl. No. 12/746,894.
Office Action mailed Jul. 10, 2014 in U.S. Appl. No. 12/747,324.
Office Action mailed Jun. 7, 2013 in U.S. Appl. No. 12/746,894.
Office Action mailed Mar. 13, 2015 in U.S. Appl. No. 13/785,439.
Office Action mailed Mar. 31, 2015 in U.S. Appl. No. 14/080,926.
Office Action mailed Mar. 5, 2015 in U.S. Appl. No. 12/747,324.
Office Action mailed Nov. 27, 2012 in U.S. Appl. No. 12/746,894.
Office Action mailed Oct. 16, 2013 in U.S. Appl. No. 12/747,324.
Office Action mailed Sep. 25, 2014 in U.S. Appl. No. 14/057,729.
Price et al., "Breast Cancer Cells Metastasize to Bone through E-Selectin Positive Vascular Gateways", AACR Annual Meeting 2014, Poster #4831, Apr. 9, 2014.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Simon et al, "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.

(56) References Cited

OTHER PUBLICATIONS

Simon et al., "Mightier than the sickle cell (editorial)", Blood, 116(10), 1633, Sep. 9, 2010.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "A Small Molecule Glycomimetic Antagonist of E-selectin (GMI-1271) Prevents Pancreatic Tumor Metastasis and Offers Improved Efficacy of Chemotherapy", Cancer Res, 74:Abstract4503, Oct. 1, 2014.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Telen et al., "GMI 1070: Reduction in Time to Resolution of Vaso-Occlusive Crisis and Decreased Opioid Use in a Prospective, Randomized, Multi-Center Double Blind, Adaptive Phase 2 Study in Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.
Titz et al., "Mimetics of Sialyl Lewisx: The Pre-Organization of the Carboxylic Acid is Essential for Binding to Selectins", Chimia, 61:194-197, 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract #564, Dec. 7, 2009.
Winkler et al., "Administration of E-selectin Antagonist GMI-1271 Improves Survival to High-Dose Chemotherapy by Alleviating Mucositis and Accelerating Neutrophil Recovery", Blood, 122(21):2266, Nov. 15, 2013.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster #63045, Dec. 8, 2013.
Winkler et al., "Mobilisation of Reconstituting HSC Is Boosted by Synergy Between G-CSF and E-Selectin Antagonist GMI-1271", Blood, 124(21):317, Dec. 6, 2014.
Winkler et al., "Vascular Niche E-Selectin Protects Acute Myeloid Leukemia Stem Cells from Chemotherapy", Blood, 124(21):620, Dec. 6, 2014.
Winkler et al., "Vascular Niche E-Selectin Regulates Hematopoietic Stem Cell Dormancy, Self Renewal and Chemoresistance", Nature Medicine, doi:10.1038/nm2969, Oct. 21, 2012.
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.

* cited by examiner

Synthesis of compound 10

Synthesis of compound 14

Synthesis of compound 20

Synthesis of compound 23

Synthesis of compound 25

E-SELECTIN ANTAGONIST COMPOUNDS, COMPOSITIONS, AND METHODS OF USE

CROSS REFERENCE TO RELATED APPLICATIONS

This application is a United States national stage application filed under 35 U.S.C. §371 of International Patent Application No. PCT/US2012/071519 accorded an international filing date of Dec. 21, 2012; which application claims the benefit under 35 U.S.C. §119(e) to U.S. Provisional Application No. 61/579,646 filed Dec. 22, 2011, U.S. Provisional Application No. 61/583,547 filed Jan. 5, 2012, U.S. Provisional Application No. 61/704,399 filed Sep. 21, 2012, U.S. Provisional Application No. 61/704,424 filed Sep. 21, 2012, and U.S. Provisional Application No. 61/734,924 filed Dec. 7, 2012, which applications are incorporated by reference herein in their entirety.

BACKGROUND

1. Technical Field

Agents and compositions thereof are described herein that are E-selectin antagonists and may be used as therapeutics. Methods and uses for these E-selectin antagonists for treating and preventing diseases, disorders, and conditions associated with E-selectin activity are described herein.

2. Description of the Related Art

Many pathological conditions such as autoimmune and inflammatory diseases, shock, and reperfusion injuries involve abnormal adhesion of white blood cells. When abnormal adhesion of selectin-mediated cell adhesion occurs tissue damage may result instead of repair. Selectins include three cell adhesion molecules that have well-characterized roles in leukocyte homing. E-selectin (endothelial selectin) and P-selectin (platelet selectin) are expressed by endothelial cells at sites of inflammation or injury. Recent investigations have suggested that cancer cells are immunostimulatory and interact with selectins to extravasate and metastasize (see, e.g., Gout et al., *Clin. Exp. Metastasis* 25:335-344 (2008); Kannagi et al., *Cancer Sci.* 95:377-84 (2004); Witz, *Immunol. Lett.* 104:89-93 (2006); Brodt et al., *Int. J. Cancer* 71:612-19 (1997)).

A number of cancers are highly treatable when treated before the cancer has moved beyond the primary site. However, often once the cancer has spread beyond the primary site, the treatment options are limited and the survival statistics decline dramatically. For example, when colorectal cancer is detected at a local stage (i.e., confined to the colon or rectum), over 90% of those diagnosed survive more than five years. Conversely, when colorectal cancer has spread to distant sites (i.e., metastasized from the primary site to distant sites), the five-year survival rate of those diagnosed drops dramatically to only 11%.

The most common types of cancer include prostate, breast, lung, colorectal, melanoma, bladder, non-Hodgkin lymphoma, kidney, thyroid, leukemias, endometrial, and pancreatic cancers based on estimated incidence for 2012. The cancer with the highest expected incidence is prostate cancer, with more than 240,000 new cases expected in the U.S. in 2012, and the lowest expected incidence is pancreatic cancer, with approximately 44,000 new cases expected in 2012.

The highest mortality rate is for patients who have lung cancer. More than 160,000 patients are expected to succumb to the disease in 2012. Despite enormous investments of financial and human resources, cancer such as colorectal cancer remains one of the major causes of death. Colorectal cancer is the second leading cause of cancer-related deaths in the United States of cancers that affect both men and women. Over the last several years, more than 50,000 patients with colorectal cancer have died every year.

The four hematological cancers that are most common are acute lymphocytic leukemia (ALL), chronic lymphocytic leukemia (CLL), chronic myelogenous leukemia (CML), and acute myelogenous leukemia (AML). Leukemias and other cancers of the blood, bone marrow, and lymphatic system, affect 10 times more adults than children; however, leukemia is the most common childhood cancer, and 75% of childhood leukemias are ALL. AML is the most common leukemia in adults. Approximately 47,000 new cases are diagnosed every year, and approximately 23,500 people die every year from leukemia.

Cancer therapeutic drugs may contribute to endothelial injury, which can in turn cause venous thromboembolism (VTE). Other risk factors that predispose an individual to VTE include stasis or endothelial injury (e.g., resulting from indwelling venous device; major trauma or injury), medical conditions, (e.g., malignancy, pregnancy, cardiovascular conditions or events), administration of other drugs such as hormones, and thrombophilia. Blockage of the flow of blood in a body deprives tissue of oxygen and results in damage, destruction or death of the tissue. A thrombus and an embolism can lodge in a blood vessel and block the flow of blood. In the United States, approximately 900,000 cases of VTE, which includes deep venous thrombosis (DVT) and pulmonary embolism (PE), are diagnosed annually and about 300,000 cases are fatal (Heit et al., *Blood* 2005; 106 (abstract)). Venous thrombosis occurs when red blood cells and fibrin, and to a minor degree, platelets and leukocytes, form a mass within an intact vein. Typically, a pulmonary embolism occurs when a thrombus or a portion of the thrombus detaches from a vein wall and lodges within a pulmonary artery. Because signs and symptoms of VTE are nonspecific and difficult to diagnose, the exact incidence of VTE is unknown but may have an annual incidence of 0.1-0.2% (see, e.g., Anderson et al., *Arch. Intern. Med* 151:933-38 (1991); Silverstein et al., *Arch. Intern. Med.* 158:585-93 (1998)).

BRIEF SUMMARY

Briefly, provided herein are agents that are E-selectin antagonists, compositions comprising the agents, and methods for using the agents. These agents are useful for treating and preventing diseases and disorders treatable by inhibiting binding of an E-selectin to an E-selectin ligand, such as cancer, metastasis, and thrombosis among others described herein. In certain embodiments, glycomimetic compounds that are E-selectin antagonists are provided. Disclosed herein are the following embodiments.

In one embodiment, provided herein is a compound (which is a glycomimetic compound) having the following formula (I):

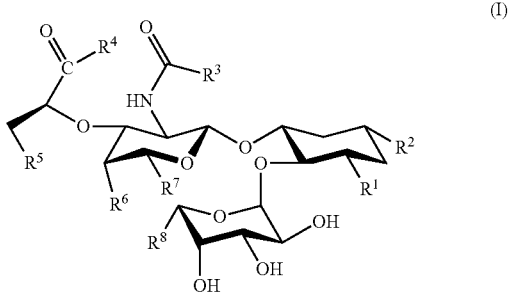

or a pharmaceutically acceptable salt, isomer, tautomer, hydrate, or solvate thereof, wherein each of $R^1$, $R^2$, $R^3$, $R^4$, $R^5$, $R^6$, $R^7$ and $R^8$ have the definitions described herein.

In certain embodiments, $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^2$ is H, or a non-glycomimetic moiety or a linker-non-glycomimetic moiety, wherein the non-glycomimetic moiety is selected from polyethylene glycol, thiazolyl, chromenyl, —C(=O)NH(CH$_2$)$_{1-4}$NH$_2$, $C_1$-$C_8$ alkyl, and —C(=O)OY where Y is $C_1$-$C_4$ alkyl, $C_2$-$C_4$ alkenyl or $C_2$-$C_4$ alkynyl;

$R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;

$R^4$ is —OH or —NZ$^1$Z$^2$ where $Z^1$ and $Z^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein $Z^1$ and $Z^2$ join to form a ring;

$R^5$ is $C_3$-$C_8$ cycloalkyl;

$R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^7$ is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

Additional substructures including, for example compounds of formula (Ia) and other substructures and specific structures of the glycomimetic compound of formula (I) are described in greater detail herein. Pharmaceutical compositions are also provided that comprise any one or more of the compounds described above and herein and a pharmaceutically acceptable excipient.

Provided herein is a method for treating or preventing metastasis of cancer cells in a subject, comprising administering to the subject a compound having a structure of formula (I), substructure (Ia), or any other substructure or specific structure described herein, or administering a pharmaceutical composition comprising the compound and a pharmaceutically acceptable excipient.

In another embodiment, a method is provided for treating or preventing metastasis of cancer cells in a subject, comprising administering to the subject a pharmaceutical composition comprising (a) a pharmaceutically acceptable excipient, and (b) an agent that is capable of competing with a compound having a structure of formula (I), substructure (Ia), or any other substructure or specific structure described herein for binding to E-selectin; wherein the agent is an antibody, polypeptide, peptide or aptamer.

In still another embodiment, a method is provided for inhibiting infiltration of cancer cells into bone marrow in a subject, comprising administering to the subject a compound having a structure of formula (I), substructure (Ia), or any other substructure or specific structure described herein, or administering a pharmaceutical composition comprising the compound and a pharmaceutically acceptable excipient.

In another embodiment, a method is provided for inhibiting infiltration of cancer cells into bone marrow in a subject, comprising administering to the subject a pharmaceutical composition comprising (a) a pharmaceutically acceptable excipient, and (b) an agent that is capable of competing with a compound having a structure of formula (I), substructure (Ia), or any other substructure or specific structure described herein for binding to E-selectin; wherein the agent is an antibody, polypeptide, peptide or aptamer.

In one embodiment, a method is provided for inhibiting adhesion of a tumor cell that expresses a ligand of E-selectin to an endothelial cell expressing E-selectin, wherein the method comprises contacting the endothelial cell with a compound having a structure of formula (I), substructure (Ia), or any other substructure or specific structure described herein, or administering a pharmaceutical composition comprising the compound and a pharmaceutically acceptable excipient, permitting the compound to interact with E-selectin present on the endothelial cell, and thereby inhibiting binding of the tumor cell to the endothelial cell. In a specific embodiment, the endothelial cell is present in the bone marrow.

In another embodiment, a method is provided for treating a cancer in a subject comprising administering to the subject (a) a compound having a structure of formula (I), substructure (Ia), or any other substructure or specific structure described herein, or administering a pharmaceutical composition comprising the compound and a pharmaceutically acceptable excipient; and (b) at least one of (i) chemotherapy and (ii) radiotherapy.

In still another embodiment, a method is provided for treating or preventing thrombosis in a subject, comprising administering to the subject a compound having a structure of formula (I), substructure (Ia), or any other substructure or specific structure described herein, or administering a pharmaceutical composition comprising the compound and a pharmaceutically acceptable excipient.

In yet another a method for treating or preventing thrombosis in a subject, comprising administering to the subject a pharmaceutical composition comprising a pharmaceutical composition comprising (a) a pharmaceutically acceptable excipient, and (b) an agent that is capable of competing with a compound having a structure of formula (I), substructure (Ia), or any other substructure or specific structure described herein for binding to E-selectin; wherein the agent is an antibody, polypeptide, peptide or aptamer.

In one embodiment, a method is provided for enhancing hematopoietic stem cell survival in a subject, comprising administering to the subject a compound having a structure of formula (I), substructure (Ia), or any other substructure or specific structure described herein, or administering a pharmaceutical composition comprising the compound and a pharmaceutically acceptable excipient. In yet another embodiment, a method is provided for enhancing hematopoietic stem cell survival in a subject, comprising administering to the subject a pharmaceutical composition comprising (a) a pharmaceutically acceptable excipient, and (b) an agent that is capable of competing with a compound having a structure of formula (I), substructure (Ia), or any other substructure or specific structure described herein for binding to E-selectin; wherein the agent is an antibody, polypeptide, peptide or aptamer. In certain embodiments, the subject has received or will receive chemotherapy or radiotherapy or both chemotherapy and radiotherapy.

Also provided herein is a use of a compound having a structure of formula (I), substructure (Ia), or any other substructure or specific structure described herein in the manufacture of a medicament for treating or preventing metastasis of cancer cells.

In another embodiment, provided herein is a use of a compound having a structure of formula (I), substructure (Ia), or any other substructure or specific structure described herein in the manufacture of a medicament for use in combination with chemotherapy or radiotherapy or both chemotherapy and radiotherapy for treating cancer.

In another embodiment, provided herein is a use of a compound having a structure of formula (I), substructure (Ia), or any other substructure or specific structure described herein in the manufacture of a medicament for treating or preventing thrombosis.

In yet another embodiment, provided herein is a use of a compound having a structure of formula (I), substructure (Ia), or any other substructure or specific structure described herein in the manufacture of a medicament for inhibiting infiltration of cancer cells into bone marrow.

In still another embodiment, provided herein is a use of a compound having a structure of formula (I), substructure (Ia), or any other substructure or specific structure described herein in the manufacture of a medicament for inhibiting adhesion of a tumor cell that expresses a ligand of E-selectin to an endothelial cell expressing E-selectin.

In another embodiment, provided herein is a use of a compound having a structure of formula (I), substructure (Ia), or any other substructure or specific structure described herein in the manufacture of a medicament for enhancing hematopoietic stem cell survival.

In another embodiment, a method is provided for treating or preventing (i.e., decreasing or reducing the likelihood of occurrence of) metastasis of cancer cells in an individual (i.e., subject) who is in need thereof, comprising administering to the individual any one or more of the glycomimetic compounds of formula (I) described above and herein or a pharmaceutical composition comprising the compound.

In yet another embodiment, a method is provided for decreasing the likelihood of occurrence of metastasis of cancer cells in an individual who is in need thereof, comprising administering to the individual an agent that competes with the compound of formula (I) described above and herein for binding to E-selectin; wherein the agent is an antibody, polypeptide, peptide or aptamer. In certain embodiments, the agent is in combination with a pharmaceutically acceptable excipient (i.e., a pharmaceutical composition).

In still another embodiment, a method is provided for decreasing the likelihood of occurrence of infiltration of cancer cells into bone marrow in an individual who is in need thereof, said method comprising administering to the individual any one or more of the glycomimetic compounds of formula (I) described above and herein or a pharmaceutical composition comprising the compound.

In another embodiment, a method is provided for decreasing the likelihood of occurrence of infiltration of cancer cells into bone marrow in an individual who is in need thereof, comprising administering to the individual an agent that competes (i.e., is capable of competing) with the compound of formula (I) described above and herein for binding to E-selectin; wherein the agent is an antibody, polypeptide, peptide or aptamer. In certain embodiments, the agent is in combination with a pharmaceutically acceptable excipient (i.e., a pharmaceutical composition).

In yet another embodiment, a method is provided for decreasing the likelihood of occurrence of thrombus formation in an individual, comprising administering to the individual any one or more of the glycomimetic compounds described above and herein, or a pharmaceutical composition comprising the compounds. In other particular embodiments, a method is provided for decreasing the likelihood of occurrence of thrombus formation in an individual, comprising administering to the individual any one or more of an agent that competes (i.e., is capable of competing) with the compound described above and herein for binding to E-selectin; wherein the agent is an antibody, polypeptide, peptide or aptamer.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a compound" may refer to one or more compounds, or a plurality of such compounds, and reference to "a cell" or "the cell" includes reference to one or more cells and equivalents thereof (e.g., plurality of cells) known to those skilled in the art, and so forth. Similarly, reference to "a composition" includes a plurality of such compositions, and refers to one or more compositions unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1A:
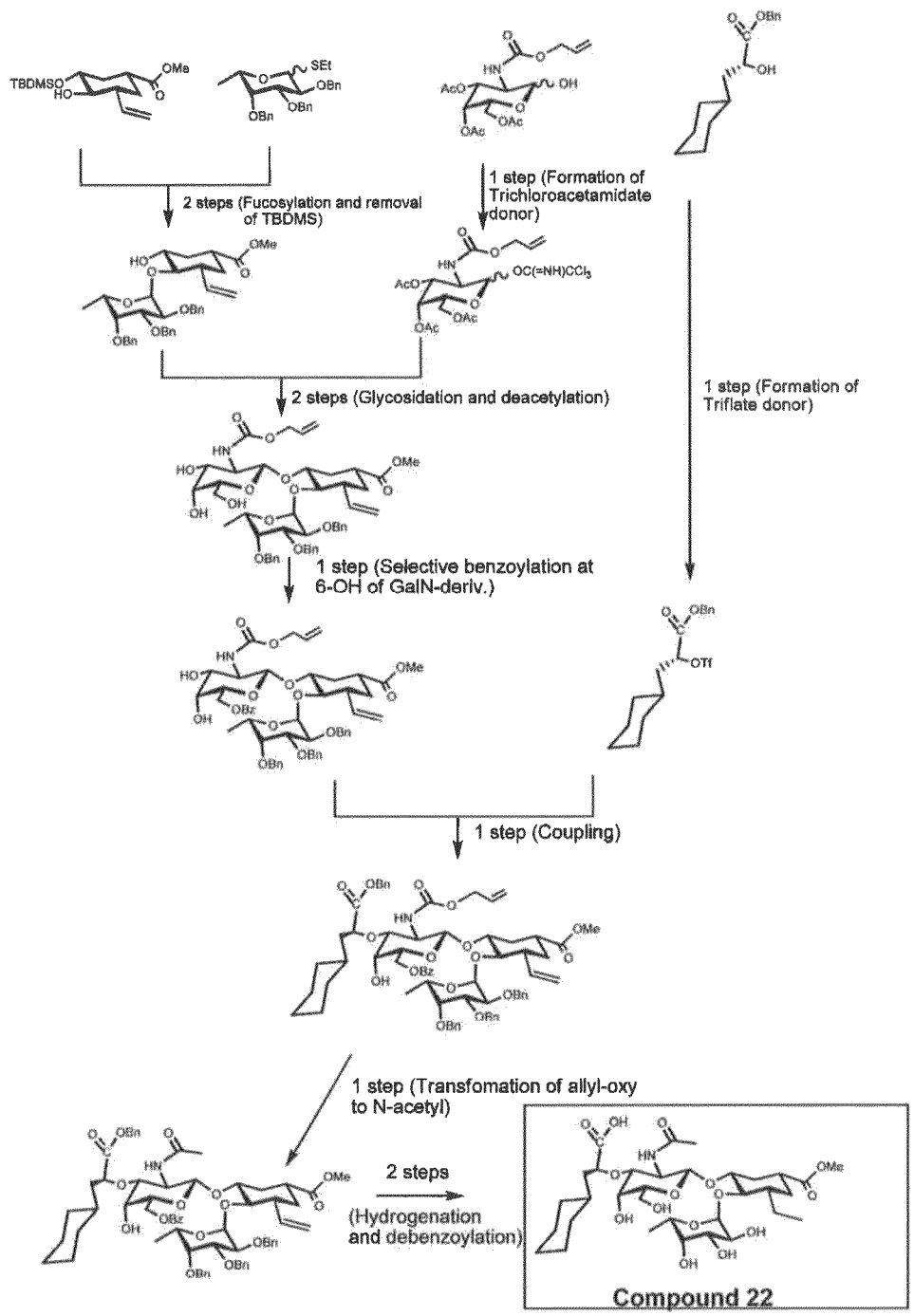
FIG. 1 (FIG. 1A, FIG. 1B, FIG. 1C and FIG. 1D) is a diagram illustrating the synthesis of an embodiment (compound 25) of the compounds having formula I provided herein.
Figure 1B:
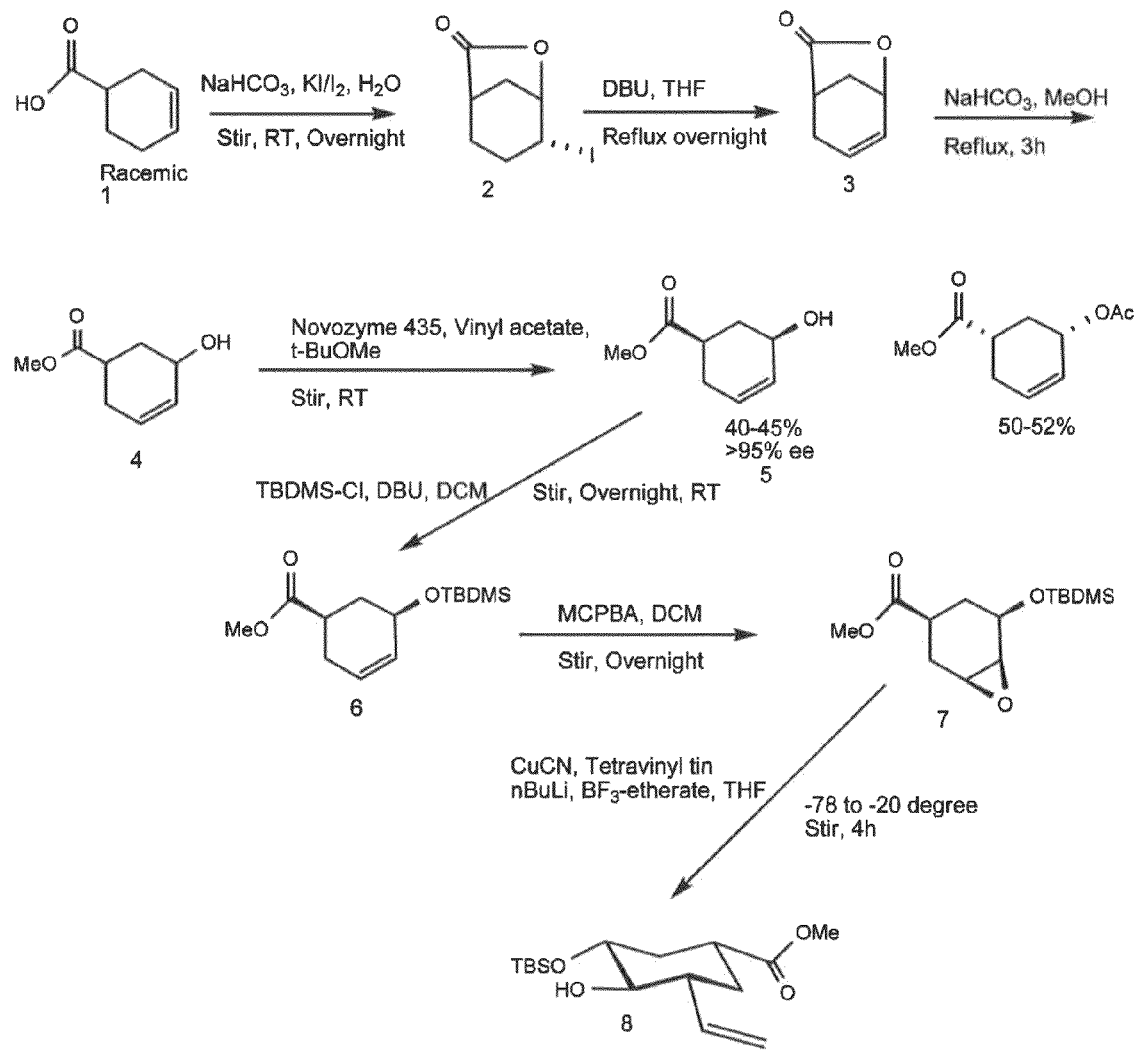
Figure 1C:
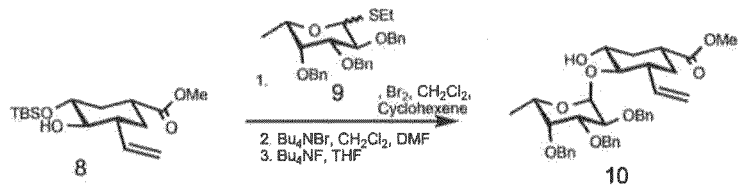
Figure 1C:
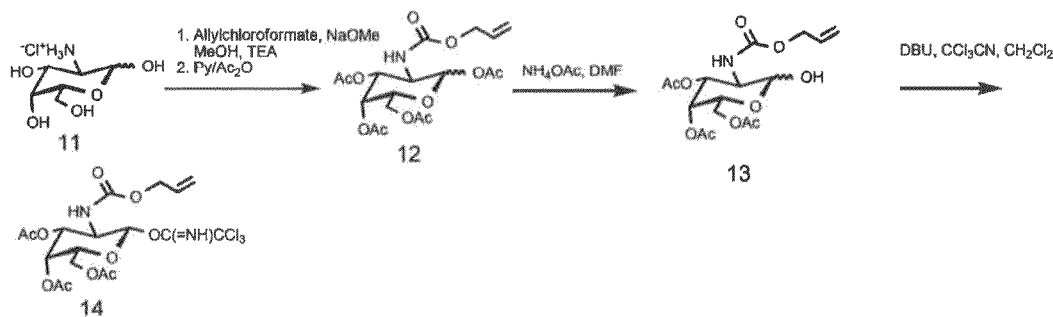
Figure 1C:
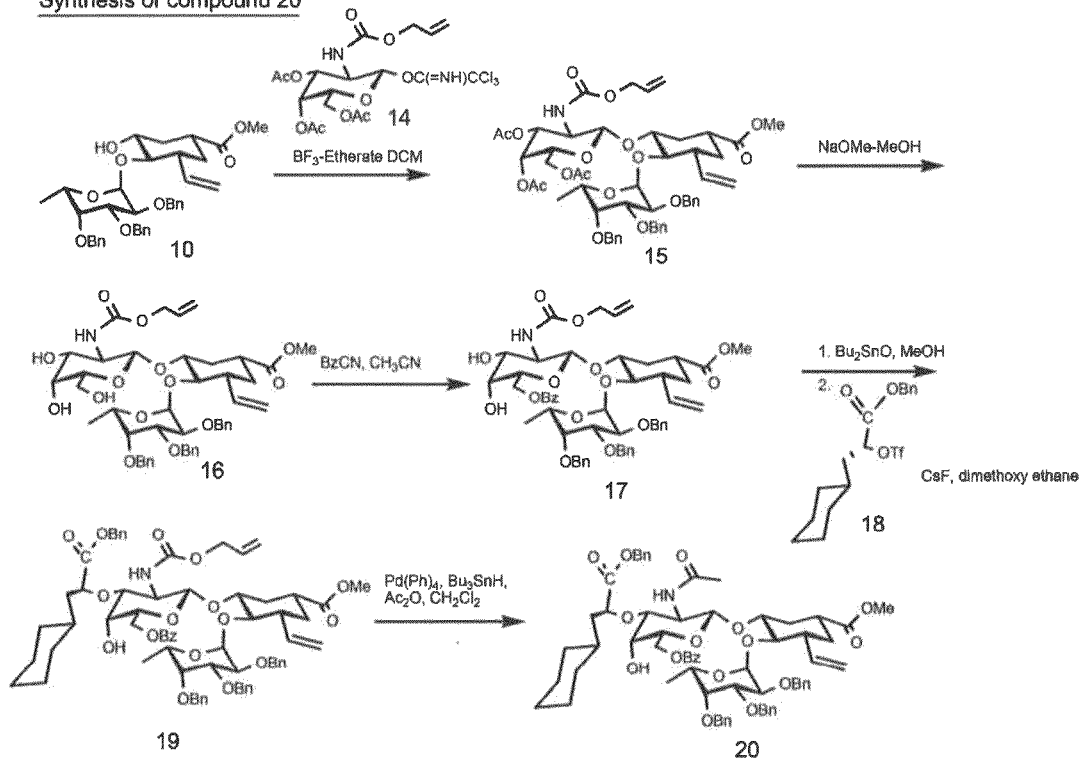
Figure 1D:
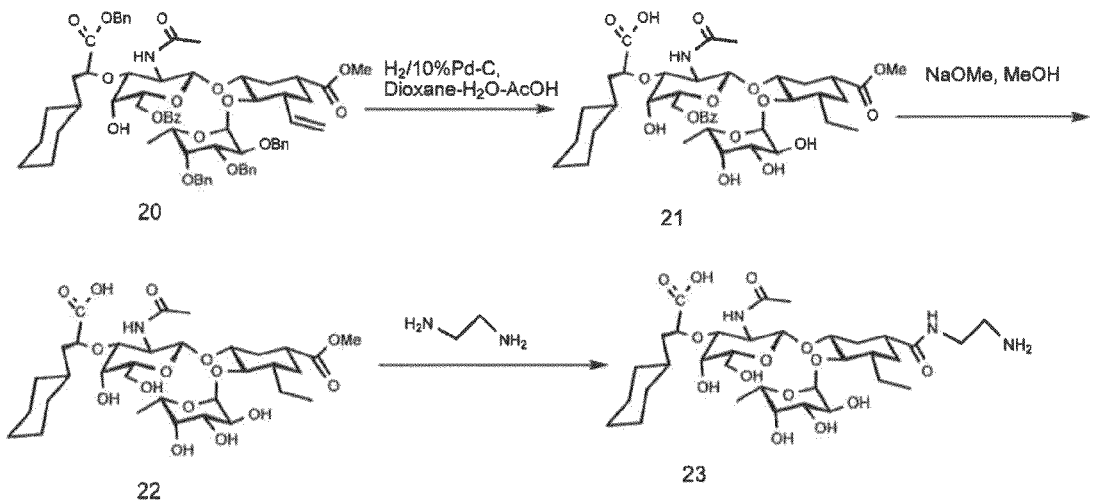
Figure 1D:
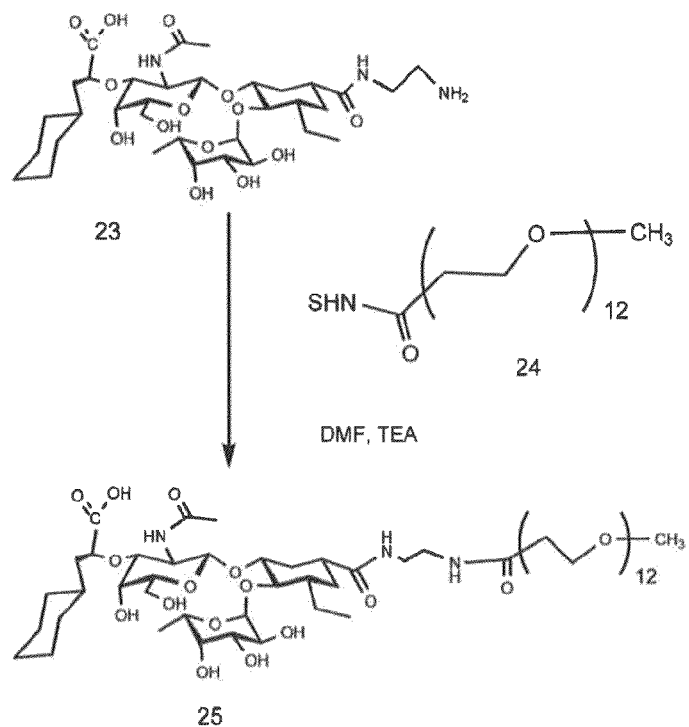

Provided herein are agents that inhibit binding of E-selectin to an E-selectin ligand. The agents include glycomimetic compounds described herein that inhibit interaction of E-selectin with sialyl Le$^a$ (sLe$^a$) or sialyl Le$^x$ (sLe$^x$). Agents that are also provided are antibodies, polypeptides, peptides and aptamers that bind at or near the binding site on E-selectin to which the compounds bind (i.e., an antibody, polypeptide, peptide, or aptamer as described herein that is capable of competing with the compounds to inhibit E-selectin interaction with sialyl Le$^a$ (sLe$^a$) or sialyl Le$^x$ (sLe$^x$)).

The E-selectin antagonists described herein may be used in methods for treating a disease or disorder associated with, mediated by, or exacerbated by E-selectin binding to an E-selectin ligand, which in turn causes an undesired biological activity, including, for example, an inflammatory response, promotion of tumor cell migration (i.e., promoting or enhancing metastasis), enhancing chemotherapy resistance of tumor cells, and contributing to thrombus formation. In certain embodiments, the agents, including the E-selectin antagonist glycomimetic compounds described herein, may be used in the treatment of cancers in combination with chemotherapy, radiotherapy, or both. In still other embodiments, the compounds described herein may be used for treatment and prevention of metastasis of cancer cells (also called herein tumor cells), including inhibiting infiltration of the cancer cells into bone marrow and reducing or inhibiting adhesion of the cancer cells to endothelial cells including cells in bone marrow.

Provided herein are agents, such as glycomimetic compounds, that significantly inhibited venous thromboembolism in a treatment model of thrombus formation and which have certain advantages over current treatments of thrombosis. The agents described herein therefore can be used for treating and preventing (i.e., decreasing, inhibiting, or reducing the likelihood of occurrence in a statistical, biological, or clinically significant manner) thrombosis, including deep vein thrombosis and accompanying pulmonary embolism.

E-selectin antagonists (e.g., compounds of formula I) described herein comprise substituents that are less likely to be cleaved by esterases and thus have increased stability. These compounds therefore provide improved compounds than those previously described in the art.

Agents

In one embodiment provided herein, the E-selectin antagonist is a glycomimetic compound that has the following formula (I):

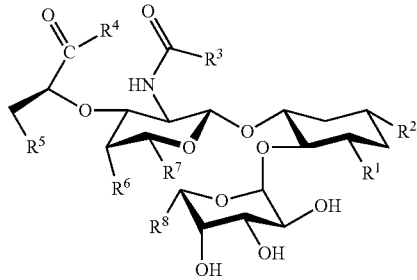

(I)

or a pharmaceutically acceptable salt (i.e., physiologically suitable salt), isomer, tautomer, hydrate or solvate thereof. Formula I comprises $R^1$ to $R^8$ that represent positions on the compound at which a substituent (e.g., $R^8$) or a portion of a substituent (e.g., $R^3$) may be varied according to the choices provided herein.

In one embodiment, $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^2$ is H, or a non-glycomimetic moiety or a linker-non-glycomimetic moiety (i.e., a linker joined to a non-glycomimetic moiety), wherein the non-glycomimetic moiety is selected from polyethylene glycol, thiazolyl, chromenyl, $C_1$-$C_8$ alkyl, —C(═O)NH(CH$_2$)$_{1-4}$NH$_2$ and —C(═O)OY where Y is $C_1$-$C_4$ alkyl, $C_2$-$C_4$ alkenyl or $C_2$-$C_4$ alkynyl;

$R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;

$R^4$ is —OH, or —NZ$^1$Z$^2$, where Z$^1$ and Z$^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein Z$^1$ and Z$^2$ join to form a ring;

$R^5$ is $C_3$-$C_8$ cycloalkyl;

$R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^7$ is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

In some embodiments, the compound of formula (I) is selected from compounds wherein (a) at least one of $R^1$, $R^3$, $R^6$, $R^7$ and $R^8$ is $C_1$-$C_8$ haloalkyl; (b) at least one of $R^3$, $R^6$, $R^7$ and $R^8$ is $C_1$-$C_8$ haloalkyl; (c) at least two of $R^1$, $R^3$, $R^6$, $R^7$ and $R^8$ are $C_1$-$C_8$ haloalkyl; (d) $R^2$ is a linker-non-glycomimetic moiety; or (e) at least one of $R^1$, $R^3$, $R^6$, $R^7$ and $R^8$ is $C_1$-$C_8$ haloalkyl, and $R^2$ is a linker-non-glycomimetic moiety.

In a particular embodiment of the compound of formula I, $C_1$-$C_8$ haloalkyl is selected from —CH$_2$X, —CH$_2$—(CH$_2$)$_m$—CH$_2$X, —CHX$_2$, —CH$_2$—(CH$_2$)$_m$—CHX$_2$, —CX$_3$ and —CH$_2$—(CH$_2$)$_m$—CX$_3$, wherein m is 0-6 and X is F, Cl, Br or I. In this embodiment, the terminal carbon is substituted with one or more halo radicals. In specific embodiments, X is F. When two or more halo radicals are present, each is independently selected. The number of methylene groups represented by "m" is "0-6" which includes 0, 1, 2, 3, 4, 5, 6 and all ranges between and including 0 to 6. In certain embodiments, at least one of $C_1$-$C_8$ haloalkyl is CH$_2$X, —CHX$_2$, or —CX$_3$; in certain more specific embodiments, X is F.

In one embodiment of the compound of formula (I), $R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In certain embodiments of the compound of formula I, $R^1$ is $C_1$-$C_8$ alkyl or $C_1$-$C_8$ haloalkyl. In more particular embodiments, $R^1$ is $C_1$-$C_3$ alkyl or $C_1$-$C_3$ haloalkyl. In a more specific embodiment, $R^1$ is methyl (—$CH_3$), ethyl ($CH_2CH_3$), or —$CF_3$ or —$CHF_2$. In another embodiment, $R^1$ is methyl (—$CH_3$) or —$CHF_2$.

In one embodiment of the compound of formula (I), $R^2$ is H, or a non-glycomimetic moiety (M) or a linker (L)-non-glycomimetic moiety, wherein the non-glycomimetic moiety is selected from $C_1$-$C_8$ alkyl, —C(=O)NH($CH_2$)$_{1-4}$$NH_2$, polyethylene glycol (PEG), thiazolyl, chromenyl and —C(=O)OY wherein Y is $C_1$-$C_4$ alkyl, $C_2$-$C_4$ alkenyl or $C_2$-$C_4$ alkynyl. In one particular embodiment, $R^2$ is a non-glycomimetic moiety (M), linker (L)-non-glycomimetic moiety (also indicated as -L-non-glycomimetic moiety or -L-M), wherein the non-glycomimetic moiety is polyethylene glycol. In a particular embodiment, $R^2$ is —C(=O)NH($CH_2$)$_2$$NH_2$. In certain embodiments, when $R^2$ comprises the non-glycomimetic moiety or a linker-non-glycomimetic moiety described herein, these moieties provide advantageous or improved characteristics such as enhanced bioavailability; desired pharmacokinetics; improved stability, and the like, to the compound and are non-immunogenic. Other exemplary non-glycomimetic moieties described herein include thiazolyl and chromenyl heteroaryls, for example 4-methylthiazolyl and 7-hydroxy-2H-chromen-2-on-yl. In some embodiments, $R^2$ is H.

$R^2$ may be attached to the glycomimetic portion of the compounds of formula (I) either directly or via a linker (L).

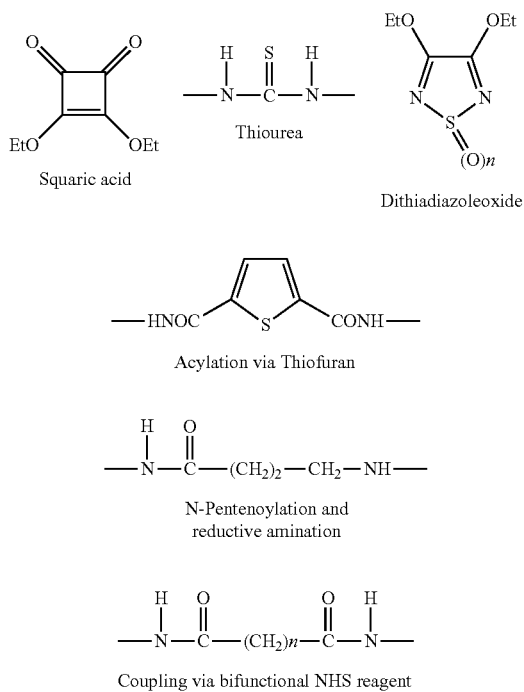

Squaric acid

Thiourea

Dithiadiazoleoxide

Acylation via Thiofuran

N-Pentenoylation and reductive amination

Coupling via bifunctional NHS reagent

In still other embodiments, the linker is

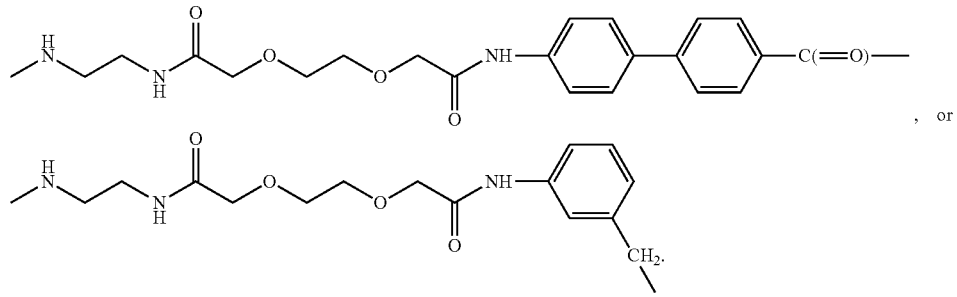

, or

Linkers are well known to a person of ordinary skill in the art. In particular embodiments, the linker that joins the glycomimetic moiety of formula I to a non-glycomimetic moiety (M) is —C(=O)NH($CH_2$)$_{1-4}$NHC(=O)—; in more specific embodiments, the linker is —C(=O)NH($CH_2$)NHC(=O)—, or the linker is —C(=O)NH($CH_2$)$_2$NHC(=O)—. In other certain embodiments, the linker is —C(=O)NH($CH_2$)$_{1-4}$NHC(=O)($CH_2$)$_{1-4}$; in more specific embodiments, the linker is —C(=O)NH($CH_2$)NHC(=O)—$CH_2$, or the linker is —C(=O)NH($CH_2$)$_2$NHC(=O)—($CH_2$)$_2$. Linkers also include those called in the art "click chemistry" linkers (see, e.g., Brik et al., *Chem. Bio. Chem.* 2003, 4, 1246; Helms et al., *J. Am. Chem. Soc.* 2004, 126, 15020; Lober et al., *Org. Lett.* 2003, 5, 1753; Moses et al., *Chem. Soc. Rev* 2007, 36, 1249-1262).

Other exemplary linkers are described in International Application Publication WO 2007/028050. By way of additional example, linkers include the following.

In another embodiment, the linker is —C(=O)—NH—($CH_2$)$_2$—NH—; —$CH_2$—NH—$CH_2$—, or is —C(=O)—NH—$CH_2$—.

In one embodiment of the compound of formula (I), $R^3$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl. In other certain embodiments of the compound of formula I, $R^3$ is $C_1$-$C_8$ alkyl or $C_1$-$C_8$ haloalkyl or cyclopropyl. In more particular embodiments, $R^3$ is $C_1$-$C_3$ alkyl or $C_1$-$C_3$ haloalkyl. In more specific embodiments, $R^3$ is —$CH_3$ (methyl) or —$CH_2$—$CH_3$ (ethyl) or —$CF_3$ or —$CHF_2$. In still other embodiments, $R^3$ is methyl or trifluoromethyl.

In one embodiment of the compound of formula (I), $R^4$ is —OH, or —$NZ^1Z^2$, where —$Z^1$ and $Z^2$ are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein $Z^1$ and $Z^2$ join to form a ring. When $Z^1$ and $Z^2$ join to form a ring, the ring is a heterocyclic ring wherein the heteroatom is N. In one specific embodiment, $R^4$ is —OH or —$NZ^1Z^2$ wherein $Z^1$ and $Z^2$ are each H or $C_1$-$C_8$ alkyl. In a more specific embodiment, $Z^1$ and $Z^2$ are each —$CH_3$ and —$NZ^1Z^2$ is —$N(CH_3)_2$.

In one embodiment of the compound of formula (I), $R^5$ is $C_3$-$C_8$ cycloalkyl (i.e., cyclopropyl, cyclobutyl, cyclopentyl, cyclohexyl, cycloheptyl or cyclooctyl). In another embodiment, $R^5$ is $C_3$-$C_6$ cycloalkyl (i.e., cyclopropyl, cyclobutyl, cyclopentyl or cyclohexyl). In a particular embodiment of the compound of formula I, $R^5$ is cyclohexyl.

In one embodiment of the compound of formula (I), $R^6$ is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In other particular embodiments of the compound of formula I, $R^6$ is —OH.

In one embodiment of the compound of formula (I), $R^7$ is —$CH_2OH$, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In yet another specific embodiment of the compound of formula I, $R^7$ is —$CH_2OH$, $C_1$-$C_8$ alkyl, or $C_1$-$C_8$ haloalkyl. In more particular embodiments, $R^7$ is —$CH_2OH$ or —$CH_3$. In another specific embodiment, $R^7$ is $C_1$-$C_3$ haloalkyl. In a more specific embodiment, $R^7$ is —$CH_2F$, —$CHF_2$ or —$CF_3$. In another specific embodiment, $R^7$ is —$CH_2OH$ or —$CHF_2$.

In one embodiment of the compound of formula (I), $R^8$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl. In another particular embodiment of the compound of formula I, $R^8$ is $C_1$-$C_8$ alkyl or $C_1$-$C_8$ haloalkyl. In more particular embodiments, $R^8$ is $C_1$-$C_3$ alkyl or $C_1$-$C_3$ haloalkyl. In a more particular embodiment, $R^8$ is methyl (—$CH_3$), —$CH2F$, —$CHF_2$ or trifluoromethyl (—$CF_3$). In another particular embodiment, $R^8$ is methyl or trifluoromethyl (—$CF_3$).

In a particular embodiment of the compound of formula I, at least one or at least two of $R^1$, $R^3$, $R^6$, $R^7$ and $R^8$ is $C_1$-$C_8$ haloalkyl. In other certain embodiments, at least one of $R^3$, $R^6$, $R^7$ and $R^8$ is $C_1$-$C_8$ haloalkyl. In other particular embodiments, $R^2$ is a linker (L)-non-glycomimetic moiety (M); in still other particular embodiments, $R^2$ is a linker (L)-non-glycomimetic moiety (M) and at least one of $R^1$, $R^3$, $R^6$, $R^7$ and $R^8$ is $C_1$-$C_8$ haloalkyl. When two or more of $R^1$, $R^3$, $R^6$, $R^7$ and $R^8$ are $C_1$-$C_8$ haloalkyl, the haloalkyls are independently selected, i.e., may be the same or different or both (if at least three present). Oral bioavailability of a compound may be improved and/or the half-life of the compound increased when at least one or more of $R^1$, $R^3$, $R^6$, $R^7$ and $R^8$ is $C_1$-$C_8$ haloalkyl and when $R^2$ comprises a non-glycomimetic moiety (M) or linker (L)-non-glycomimetic moiety (-L-M).

In another embodiment of the compound of formula (I) provided herein, $R^5$ is cyclohexyl and $R^6$ is —OH and the compound has the following formula (Ia):

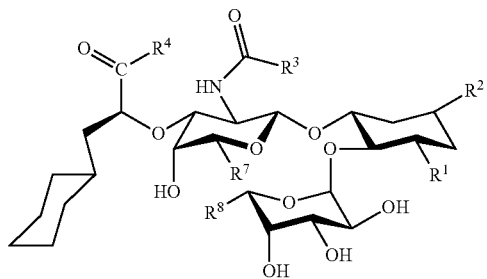

or a pharmaceutically acceptable salt (i.e., physiologically suitable salt), isomer, tautomer, hydrate or solvate thereof, wherein $R^1$ is $C_1$-$C_8$ alkyl or $C_1$-$C_8$ haloalkyl;

$R^2$ is H, a non-glycomimetic moiety or a linker-non-glycomimetic moiety, wherein the non-glycomimetic moiety is selected from polyethylene glycol, thiazolyl, chromenyl, $C_1$-$C_8$ alkyl, —$C(=O)NH(CH_2)_{1-4}NH_2$ and —$C(=O)OY$ where Y is $C_1$-$C_4$ alkyl;

$R^3$ is $C_1$-$C_8$ alkyl, $C_1$-$C_8$ haloalkyl, or cyclopropyl;

$R^4$ is —OH or —$NZ^1Z^2$ where $Z^1$ and $Z^2$ are each independently H or $C_1$-$C_8$ alkyl;

$R^7$ is —$CH_2OH$, $C_1$-$C_8$ alkyl, $C_1$-$C_8$ haloalkyl, and $R^8$ is $C_1$-$C_8$ alkyl or $C_1$-$C_8$ haloalkyl.

In certain embodiments, halo is F. In other particular embodiments, $R^1$ is —$CH_3$, —$CH_2CH_3$, —$CH_2F$, —$CHF_2$, —$CF_3$, —$CH_2CH_2F$, —$CH_2CHF_2$, or —$CH_2CF_3$. In other embodiments, $R^3$ is —$CH_3$, —$CH_2F$, —$CHF_2$, or —$CF_3$. In yet another particular embodiment, $R^4$ is —OH or —$N(CH_3)_2$. In certain embodiments, $R^7$ is —$CH_2OH$, —$CH_3$, —$CH_2F$, —$CHF_2$, or —$CF_3$. In still another specific embodiment, $R^8$ is —$CH_3$, —$CH_2F$, —$CHF_2$, or —$CF_3$.

In certain particular embodiments, exemplary compounds of formula (I) are provided, wherein $R^1$ is ethyl, $CF_3$, or —$CHF_2$; $R^3$ is methyl or —$CF_3$; $R^4$ is —OH, or —$N(CH_3)_2$; $R^5$ is cyclohexyl; $R^6$ is —OH; $R^7$ is —$CH_2$—OH, —$CHF_2$, or $CF_3$; $R^8$ is methyl, —$CF_3$, or —$CHF_2$; and $R^2$ is H, or a non-glycomimetic moiety or linker-non-glycomimetic moiety as described above for a compound of formula I. Examples described herein have one of the following structural formulae.

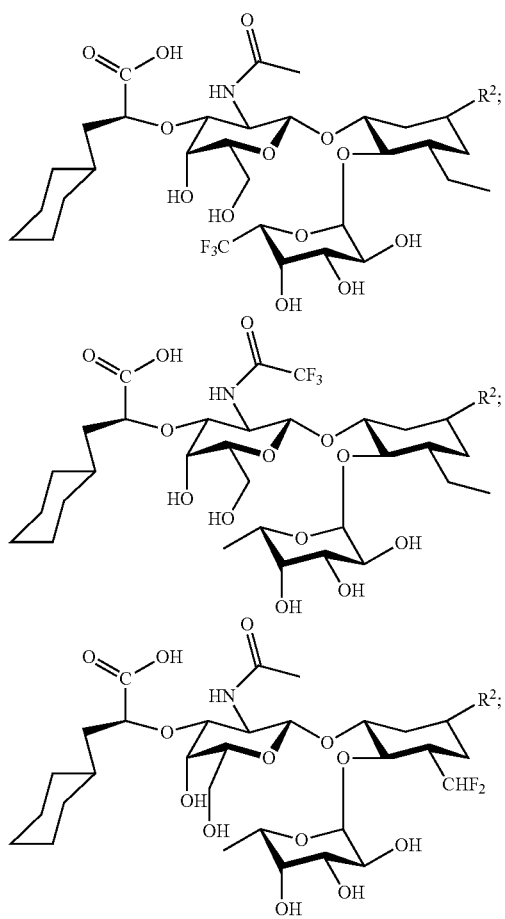

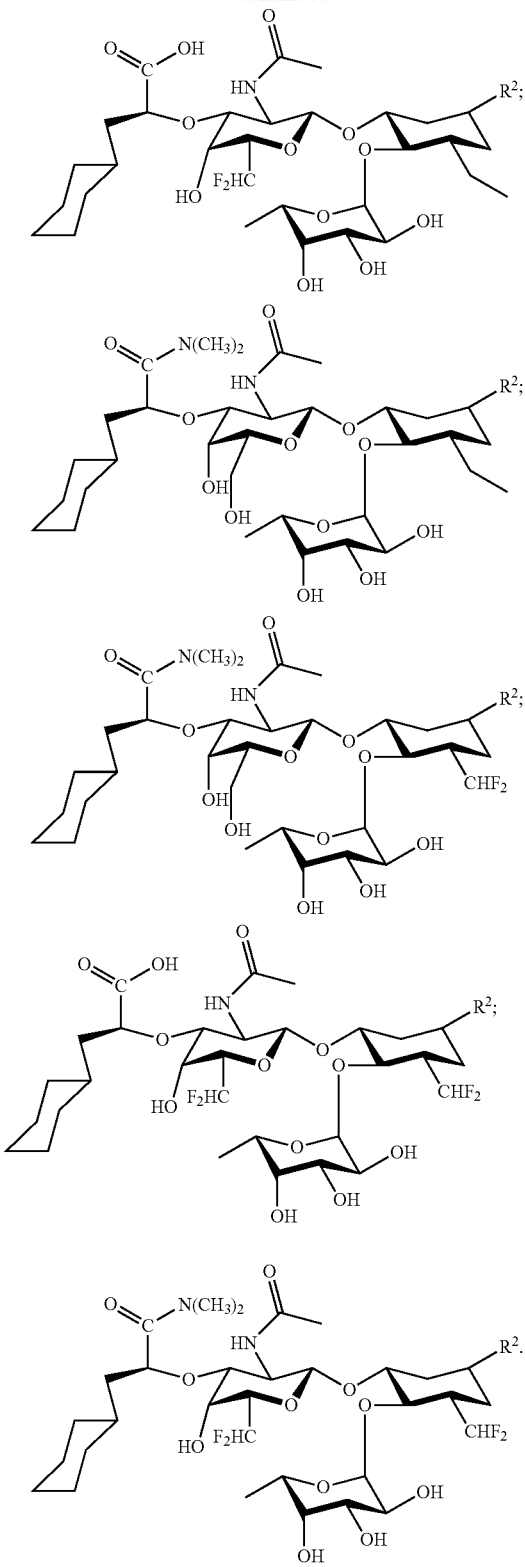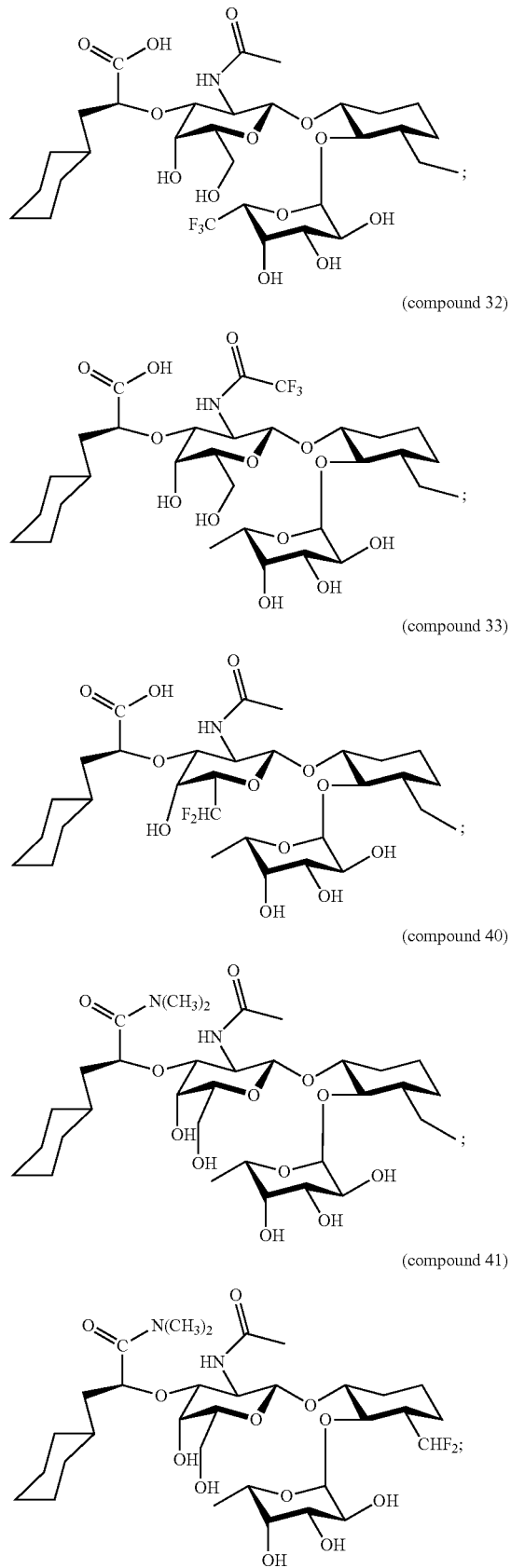
In certain particular embodiments, $R^2$ is H, —C(=O)NH(CH$_2$)$_2$NH$_2$, or —C(=O)OCH$_3$ (also depicted as —COOCH$_3$) and exemplary compounds have one of the following formulae.

(compound 36)

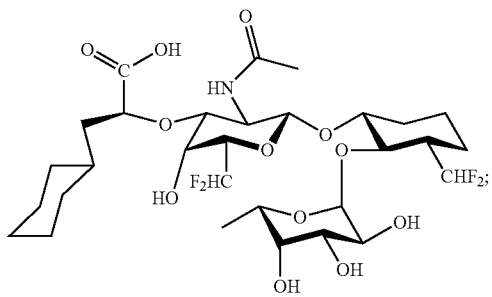

(compound 42)

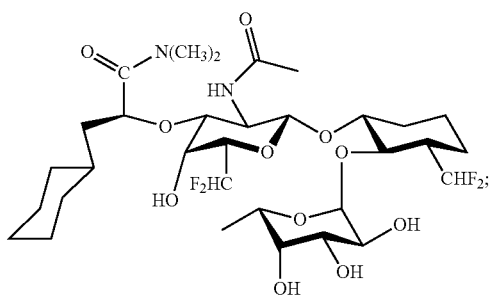

(compound 27)

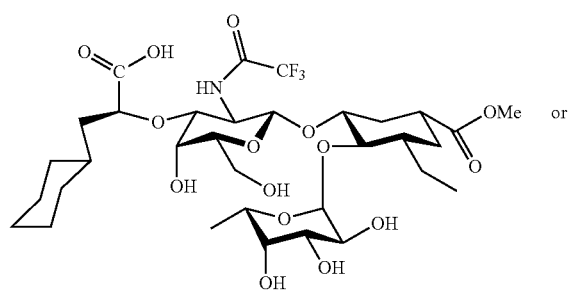

(compound 43)

Also provided herein is the following compound of formula (I):

(compound 22)

In a particular embodiment of the compound of formula I and formula Ia, $R^2$ is a non-glycomimetic moiety that is a polyethylene glycol (PEG). PEG is a polymer of repeating ethylene oxide units. Length and thus molecular weight vary depending upon how many of repeating units are present. The ethylene oxide units are abbreviated herein as $$(\diagdown\diagup O)_n$$

where n is an integer or a general range of integers from 1 to 100, and any smaller range within the general range. For example the range of integers for n may be 1 to 25, 1 to 50, 2 to 15, 2 to 20, 2 to 25, 2 to 40, 2 to 50, 2 to 100, 5 to 20, 5 to 40, 5 to 100, as well as all the other numerical combinations. In particular embodiments, n is 4, 8, 12, 16, 20, 24, or 28.

In a particular embodiment, PEG is the non-glycomimetic moiety (M) and the linker (L) is —C(═O)NH(CH₂)₂NHC(═O)— to provide one of the following compounds:

or

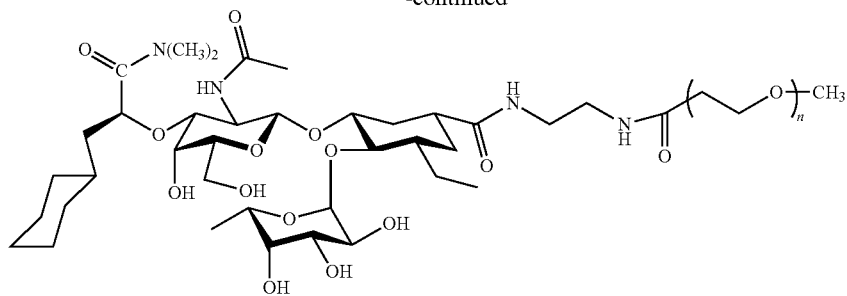
wherein n is 1 to 100. In particular embodiments, n is 4, 8, 12, 16, 20, 24, or 28.
In two particular embodiments with PEG as $R^2$, the compound of formula I has one of the following formulae:
(compound 26)
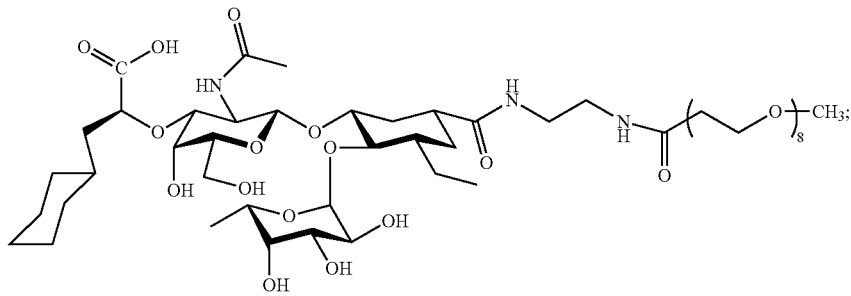
(compound 25)
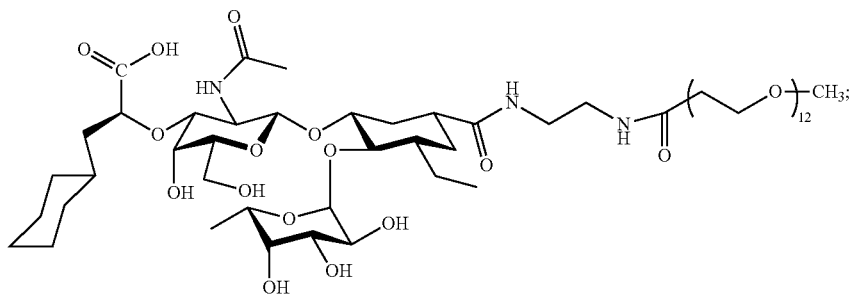
(compound 44)
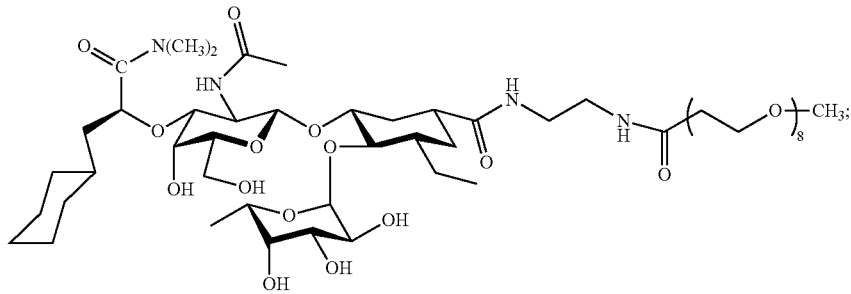
(compound 45)
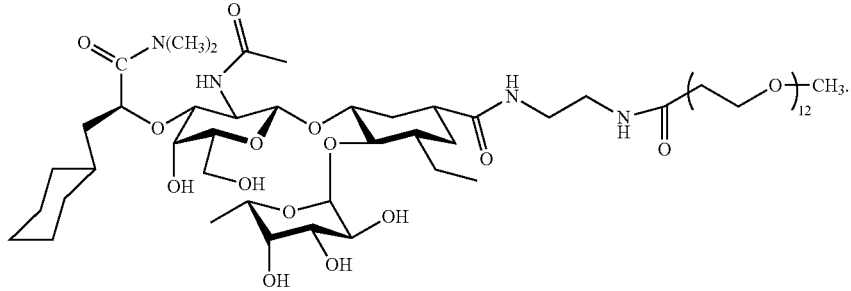

In a particular embodiment, R² is a linker-non-glycomimetic moiety, and the non-glycomimetic moiety is thiazolyl or chromenyl, for example, 4-methylthiazolyl or 7-hydroxy-2H-chromen-2-on-yl and the compound of formula (I) has one of the following formulae:

(compound 28)

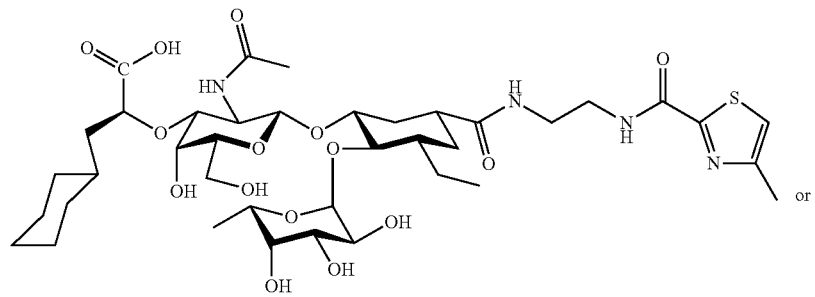

or (compound 29)

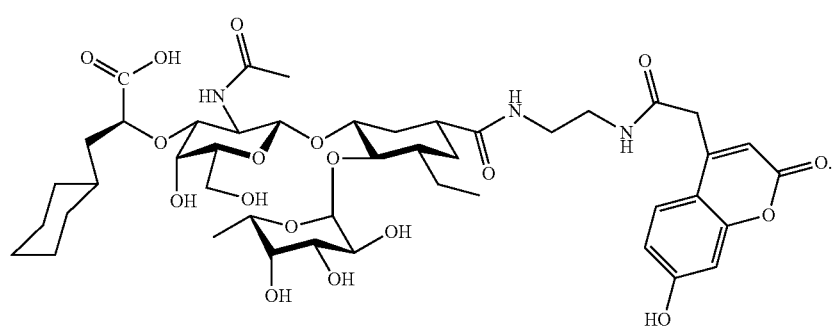

Compounds of formula I include all isomers, physiologically acceptable salts (i.e., pharmaceutically acceptable salts), hydrates, solvates, polymorphs, metabolites and prodrugs of any. Examples of isomers are stereoisomers (e.g., enantiomers and racemates) and tautomers.

Also provided herein are pharmaceutical compositions that comprise one or more of the compounds of formula (I), substructures and specific structures thereof, and a pharmaceutically acceptable excipient. A compound of formula (I) or a pharmaceutical composition comprising the compound may be used in methods described herein for treating or preventing a disease, disorder, or condition that is treatable by inhibiting (i.e., blocking, reducing, preventing) the interaction between E-selectin and a ligand of E-selectin. Such diseases and disorders include an inflammatory response and related inflammation, cancer, undesired migration or movement of a cell through the vasculature (e.g., metastasis of a tumor cell), and thrombosis, for example.

The glycomimetic compounds of formula (I) may be used for treating any one or more of the diseases or conditions described herein or for the preparation or manufacture of a medicament for use in treating any one or more of the diseases or conditions described herein. Each of these methods and uses are described in greater detail herein.

DEFINITIONS

The terms below, as used herein, have the following meanings, unless indicated otherwise. Certain chemical groups named herein are preceded by a shorthand notation indicating the total number of carbon atoms that are to be found in the indicated chemical group.

As used herein, a "$C_1$-$C_8$ alkyl" or "$C_1$-$C_4$ alkyl" refers to an alkane substituent with one to eight carbon atoms or one to four carbon atoms, respectively, and may be straight chain, branched, or cyclic (e.g., cycloalkanyl). The term "alkanyl" may also be used herein and has the same meaning as alkyl. Examples include methyl ("Me"), ethyl, propyl, isopropyl, butyl and t-butyl. A "$C_1$-$C_8$ halo alkyl" refers to a $C_1$-$C_8$ alkanyl substituted with at least one halogen (halo). When more than one halogen is present, the halogens present may be the same or different or both (if at least three present). A "$C_2$-$C_8$ alkenyl" or "$C_2$-$C_4$ alkenyl" refers to an alkene substituent with two to eight carbon atoms or two to four carbon atoms, respectively, at least one carbon-carbon double bond, and may be straight chain, branched or cyclic (cycloalkenyl). Examples are similar to "$C_1$-$C_8$ alkyl" and "$C_1$-$C_8$ alkyl" examples except the alkenyl has at least one carbon-carbon double bond. A "$C_2$-$C_8$ haloalkenyl" refers to a $C_2$-$C_8$ alkenyl substituted with at least one halogen (halo). When more than one halogen is present, the halogens present may be the same or different or both (if at least three present). A "$C_2$-$C_8$ alkynyl" or "$C_2$-$C_4$ alkynyl" refers to an alkyne substituent with two to eight carbon atoms or two to four carbon atoms, respectively, at least one carbon-carbon triple bond, and may be straight chain, branched, or cyclic (e.g., cycloalkynyl). Examples are similar to "$C_1$-$C_8$ alkyl" and "$C_1$-$C_8$ alkyl" examples except the alkanyl has at least one carbon-carbon triple bond. A "$C_2$-$C_8$ haloalkynyl" refers to a "$C_2$-$C_8$ alkynyl" substituted with at least one halogen (halo). When more than one halogen is present, the halogens present may be the same or different or both (if at least three present).

A non-glycomimetic moiety (M) is a moiety that confers one or more advantageous properties on the compound that enhance the compound's efficacy and use in vivo. Examples of such a property include increased water solubility, decreased immunogenicity, improved stability, and improved pharmacokinetic profile. An improved pharmacokinetic profile includes increased serum half-life, reduced clearance and such that improve the therapeutic index.

"Halo" (or "halogen" or "halide") is fluoro (F), chloro (Cl), bromo (Br), or iodo (I) radical.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, and sulfur. In certain embodiments, the heterocyclyl radical is a 5-10 membered heterocycle that comprises 3-9 carbon atoms and from 1-3 heteroatoms. Unless stated otherwise specifically in the specification, the heterocyclyl radical may be a monocyclic, bicyclic, tricyclic or tetracyclic ring system, which may include fused or bridged ring systems; nitrogen, carbon or sulfur atom(s) in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heterocyclylalkyl" refers to a radical of the formula —$R_b$—$R_c$ where $R_b$ is an alkylene chain as defined above and $R_c$ is one or more heterocyclyl radicals as defined above, for example, tetrahydrofuranyl-methyl, tetrahydropyranyl-methyl and the like. A 6-membered heterocyclylalkyl refers to a heterocyclylalkyl, wherein the heterocyclyl moiety has 6 atoms in the ring. Unless stated otherwise specifically in the specification, a heterocyclalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, and sulfur, and at least one aromatic ring. In certain embodiments, the heteroaryl radical is a 5-10 membered heteroaryl that comprises 3-9 carbon atoms and from 1-3 heteroatoms. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"Heteroarylalkyl" refers to a radical of the formula —$R_b$—$R_c$ where $R_b$ is an alkylene chain as defined above and $R_c$ is one or more heteroaryl radicals as defined above, for example, furanyl-methyl, pyridyl-methyl and the like. A 6-membered heteroarylalkyl refers to a heteroarylalkyl, wherein the heteroaryl moiety has 6 atoms in the ring. Unless stated otherwise specifically in the specification, a heteroarylalkyl group may be optionally substituted.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" (or physiologically suitable salt) of compounds of formula I and substructures thereof, as well as any and all substructures and specific compounds described herein is intended to encompass any and all pharmaceutically suitable salt forms.

Compounds of formula I and substructures thereof and specific structures may sometimes be depicted as an anionic species. One of ordinary skill in the art will recognize that the compounds exist with an equimolar ratio of cation. For instance, the compounds described herein can exist in the fully protonated form, or in the form of a salt such as sodium, potassium, ammonium or in combination with any inorganic base as described above. When more than one anionic species is depicted, each anionic species may independently exist as either the protonated species or as the salt species. In some specific embodiments, the compounds described herein exist as the sodium salt.

Furthermore, some of the crystalline forms of any compound described herein may exist as polymorphs, which are also included and contemplated by the present disclosure. In addition, some of the compounds may form solvates with water or other solvents. Such solvates are similarly included within the scope of compounds and compositions described herein.

With regard to stereoisomers, the compounds of formula I as well as any substructure or specific structure described herein, may have one or more chiral (or asymmetric) centers, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof include "enantiomers," which refers to two stereoisomers whose molecules are nonsuperimposeable mirror images of one another. Thus, the compounds may occur in any isomeric form, including racemates, racemic mixtures, and as individual enantiomers or diastereomers. A tautomer refers to a proton shift from one atom of a molecule to another atom of the same molecule.

"Prodrug" is meant to indicate a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound as described herein in vivo when such prodrug is administered to a mammalian subject. Prodrugs of a compound described herein may be prepared by modifying functional groups present in the compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound is administered to a mammalian subject, cleaves to form a free hydroxy, free amino or free mercapto group, respectively. Examples of prodrugs include, but are not limited to, ester and amide derivatives of hydroxy, carboxy, mercapto or amino functional groups in the compounds described herein and the like.

Compound Synthesis Procedures

Figure 2:
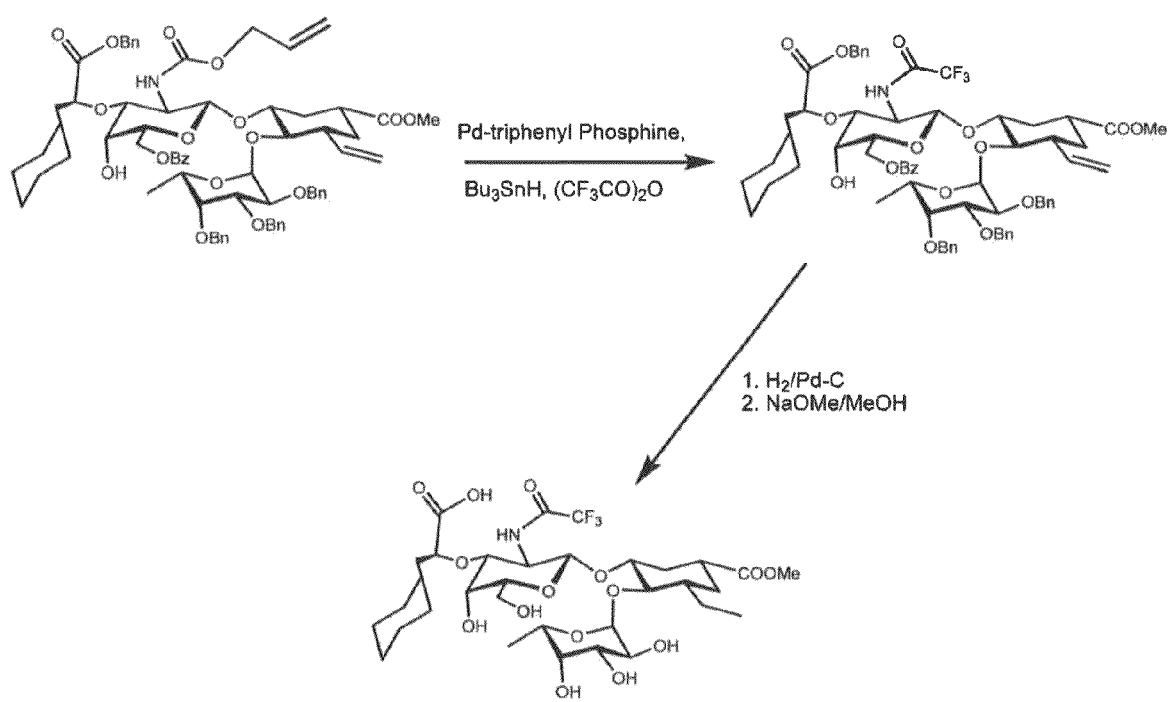
FIG. 2 is a diagram illustrating the synthesis of an embodiment of the compounds having formula I provided herein.

Synthesis of the compounds of formula I (and substructures, and specific compounds) may be performed as described herein, including the Examples, using techniques familiar to a person skilled in the art. Synthetic methods for preparing exemplary compounds described herein are described in Example 1. The methods may be used for synthesis of the compounds of formula I by using appropriate reactants for preparation of the specific compound using the techniques and methods described herein, and that are routinely practiced in the art. By way of further example, FIGS. 1 and 2 provide schematics of synthesis schemes for exemplary compounds described herein.

In general, compounds of formula (I) can be prepared according to the following General Reaction Scheme I:

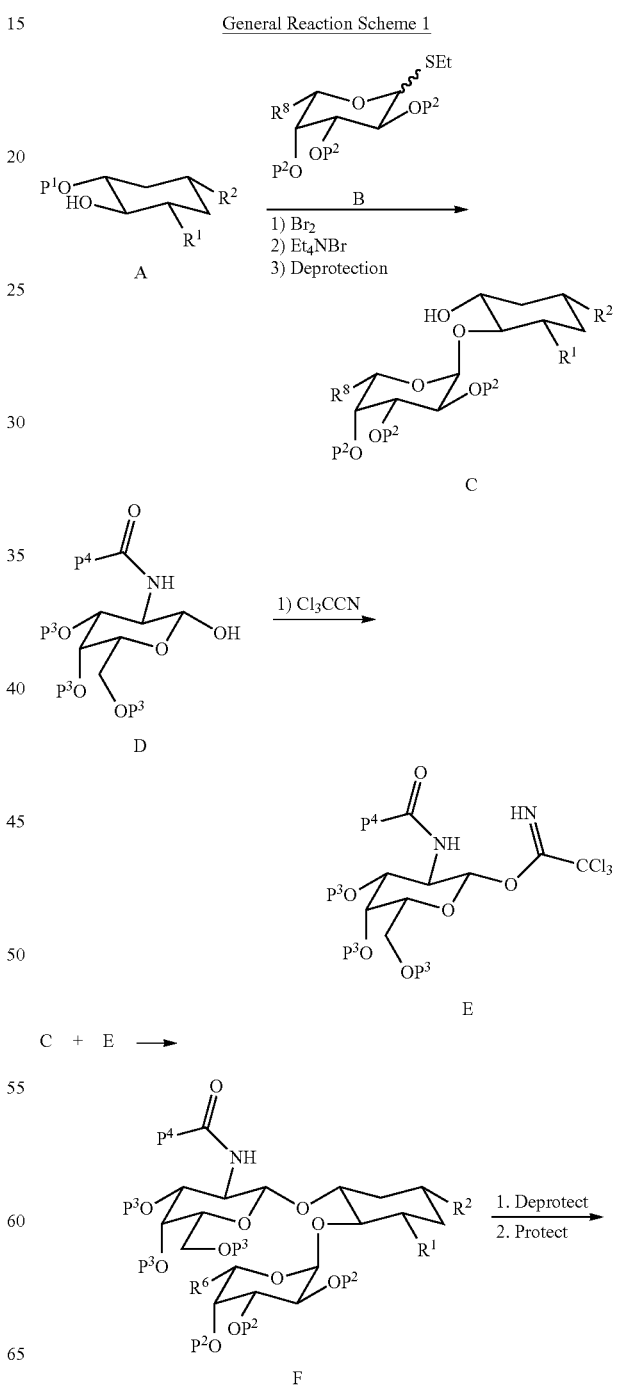

-continued

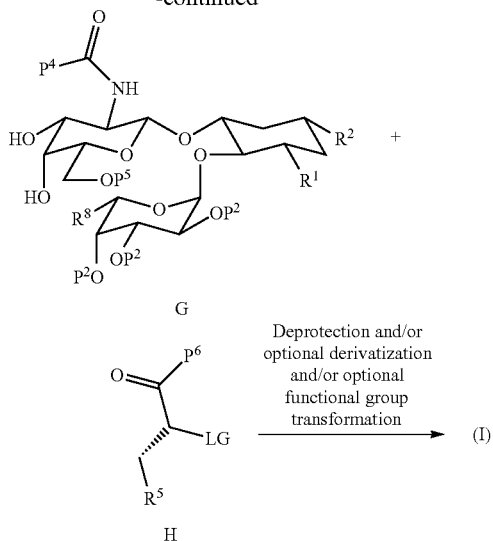

Referring to General Reaction Scheme 1, compounds of structure A, wherein $R^1$ and $R^2$ are as defined for formula (I), or are moieties which can be synthetically converted to $R^1$ or $R^2$, and $P^1$ is a suitable protecting group, can be purchased from commercial sources or prepared according to methods known in the art. Similarly, compounds of structure B, wherein $R^8$ is as defined for formula (I), or is a moiety which can be synthetically converted to $R^8$, and $P^2$ is a suitable protecting group, can be purchased from commercial sources or prepared according to methods known in the art. Reaction of A with B, under appropriate conditions (e.g., bromine followed by tetraethylamonium bromide) and subsequent selective removal of $P^1$ yields compounds of structure C.

In a parallel scheme, compound D, wherein $P^3$ is a suitable protecting group and $P^4$ is suitable protecting group or a moiety which can be synthetically manipulated to obtain $R^3$ (as defined for formula (I)), can be purchased or prepared according to known techniques. Reaction of D with a suitable activating agent (e.g., $Cl_3CCN$) yields activated compound E. Other suitable means for activating compounds of structure D are known to those of ordinary skill in the art. Coupling of C and E under appropriate conditions yields compounds of structure F.

Selective removal of $P^3$, followed by selective protection yields compounds of structure G, wherein $P^5$ is suitable protecting group. Reaction of G with H, wherein $P^6$ is suitable protecting group or a moiety which can be synthetically manipulated to obtain $R^4$ (as defined for formula (I)), $R^5$ is as defined for formula (I) and LG is a suitably activated leaving group (e.g., triflate and the like), and deprotection yields exemplary compounds of formula (I).

It will be appreciated that further synthetic manipulation may be desired to obtain certain compounds of formula (I). For example, in certain embodiments, $P^4$ may be an allyloxy group which can be transformed to obtain an alkyl amide (e.g., methyl). In other examples, $R^1$ in the above scheme may be an alkenyl moiety, and the synthetic scheme includes reduction of the alkene to an alkyl group. Various other modifications to the above General Reaction Scheme I, such as varying the starting(s) material or modifying any of the reaction products to include other non-hydroxyl moieties at $R^6$ and/or $R^7$ are possible. Methods for these and other modifications to the above exemplary scheme are well known in the art and described in more detailed in the Examples.

It will also be appreciated by those skilled in the art that in the processes described herein the functional groups of intermediate compounds may need to be protected by suitable protecting groups, even if not specifically described. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Analogous reactants to those described above may be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

In general, the compounds used in the reactions described herein may be made according to General Reaction Scheme I, Examples 1 and 2, FIGS. 1 and 2 and/or organic synthesis techniques known to those of ordinary skill in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books, articles and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

As noted above, in addition to the compounds described herein, other agents are provided that bind at or near the binding site on E-selectin for the compounds and compete with the compounds for the inhibition of E-selectin interaction with $sLe^a$ or $sLe^x$. The other agents include antibodies, polypeptides, peptides and aptamers. Such agents may be produced by a variety of means that are well known in the art. For example, the E-selectin protein is used to generate a library of antibodies. The library of antibodies is screened for one or more antibodies of interest using a compound disclosed herein, such as compound 22 of FIG. 1A. Alternatively, for example, the portion of E-selectin that binds compound 22 of FIG. 1A is identified and used to generate antibodies of interest (e.g., use of the portion as an immunogen). This portion of E-selectin may also be used to design and produce polypeptides, peptides and aptamers that compete with the compounds described herein.

Antibodies and Antigen-Binding Fragments Thereof

Also provided herein are agents, which may be an antibody, polypeptide, peptide, or aptamer that that are E-selectin antagonists and may be useful for the methods and uses described herein. Such agents bind to E-selectin at or near the binding site on E-selectin to which a compound of formula (I) as provided herein binds. These agents are therefore capable of competing with a compound of formula I to bind to E-selectin and are capable of blocking (i.e., inhibiting) binding of E-selectin to an E-selectin ligand.

An agent includes an antibody, or antigen binding fragment thereof, that specifically binds to E-selectin. As described herein, the epitope to which such an antibody binds comprises amino acids at or near the binding site on E-selectin to which a compound as provided herein binds. The epitope to which such an antibody binds may include one or more amino acids contiguous with the residues to which a compound as provided herein binds and/or may include one or more amino acid residues that are non-contiguous but which interact with the compound.

As used herein, an antibody is said to be "immunospecific," "specific for" or to "specifically bind" to an antigen of interest if it reacts at a detectable level with the antigen. Affinities of antibodies and antigen binding fragments thereof can be readily determined using conventional techniques, for example, those described by Scatchard et al. (*Ann. N. Y. Acad. Sci. USA* 51:660 (1949)) and by surface plasmon resonance (SPR) (see, e.g., Wolff et al., *Cancer Res.* 53:2560-2565 (1993)). Binding properties of an antibody to an antigen may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)).

These specific antibodies may be polyclonal or monoclonal, prepared by immunization of animals and subsequent isolation of the antibody, or cloned from specific B cells according to methods and techniques routinely practiced in the art and described herein. A variable region or one or more complementarity determining regions (CDRs) may be identified and isolated from antigen-binding fragment or peptide libraries. An antibody, or antigen-binding fragment thereof, may be recombinantly engineered and/or recombinantly produced.

An antibody may belong to any immunoglobulin class. It may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. Antibodies may generally be prepared by any of a variety of techniques known to persons having ordinary skill in the art and described herein. See, e.g., Harlow et al., *Antibodies: A Laboratory Manual*, Cold Spring Harbor Laboratory (1988); Peterson, *ILAR J.* 46:314-19 (2005); Kohler and Milstein (*Nature*, 256:495-97 (1976); *Eur. J. Immunol.* 6:511-19 (1975); Coligan et al. (eds.), *Current Protocols in Immunology*, 1:2.5.1-2.6.7 (John Wiley & Sons 1991)).

Human monoclonal anti-E-selectin antibodies may be generated by any number of techniques with which those having ordinary skill in the art will be familiar (see, e.g., U.S. Pat. No. 4,464,456; Lonberg et al., *Nature* 368:856 (1994); U.S. Pat. No. 5,877,397; Bruggemann et al., *Curr. Opin. Biotechnol.* 8:455-58 (1997); Jakobovits et al., *Ann. N. Y. Acad. Sci.* 764: 525-35 (1995)); (WO 92/02551; U.S. Pat. No. 5,627,052; Babcook et al., *Proc. Natl. Acad. Sci. USA* 93:7843-48 (1996); or other procedures as known in the art). Chimeric antibodies, specific for the portion of E-selectin of interest, including humanized chimeric antibodies, may also be generated. See, e.g., Morrison et al., *Proc. Natl. Acad. Sci. USA*, 81:6851-55 (1984); Shin et al., *Methods Enzymol.* 178:459-76 (1989)). Strategies for designing humanized antibodies are routinely practiced in the art (see, e.g., Jones et al., *Nature* 321:522-25 (1986); Riechmann et al., *Nature* 332:323-27

(1988); Padlan et al., *FASEB* 9:133-39 (1995); Chothia et al., *Nature*, 342:377-83 (1989); Bajorath et al., *Ther. Immunol.* 2:95-103 (1995)).

For particular uses, antigen-binding fragments of antibodies may be desired. Antibody fragments, F(ab')$_2$, Fab, Fab', Fv, and Fd, can be obtained, for example, by proteolytic hydrolysis of the antibody (see, e.g., Weir, *Handbook of Experimental Immunology*, Blackwell Scientific, Boston (1986)), or may be synthetically prepared or genetically engineered. Antibody fragments include recombinant single chain polypeptide molecules in which light and heavy variable regions are connected by a peptide linker (scFv proteins), and minimal recognition units (comprises at least one CDR) consisting of the amino acid residues that mimic the hypervariable region. Methods and techniques for preparing and isolating antibody fragments are described in the art (see, e.g., Larrick et al., *Methods: A Companion to Methods in Enzymology* 2:106, (1991); Courtenay-Luck, in *Monoclonal Antibodies: Production, Engineering and Clinical Application*, Ritter et al. (eds.), page 166 (Cambridge University Press 1995); and Ward et al., in *Monoclonal Antibodies: Principles and Applications*, Birch et al., (eds.), page 137 (Wiley-Liss, Inc. 1995); International Patent Application Nos. PCT/US91/08694 and PCT/US91/04666); Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; U.S. Pat. No. 5,922,545; International Application Publication Nos. WO 96/40987 and WO 98/15833).

Antibodies may also be identified and isolated from human, rabbit, mouse or chicken immunoglobulin phage libraries. Antibodies isolated from non-human species or non-human immunoglobulin libraries may be genetically engineered to "humanize" the antibody or fragment thereof. See, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Kang et al., *Proc. Natl. Acad. Sci. USA* 88:4363-66 (1991); Hoogenboom et al., *J. Molec. Biol.* 227:381-388 (1992); U.S. Pat. No. 6,703,015).

An agent that is an E-selectin antagonist also includes a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)), comprises a biologically active peptide or polypeptide capable of altering the sLe$^a$ or sLe$^x$ binding function of E-selectin that is fused in-frame with a portion, at least one constant region domain (e.g., CH1, CH2, CH3, and/or CH4). Antibody related sequences are provided in Kabat et al. (in *Sequences of Proteins of Immunological Interest*, 4th ed. (U.S. Dept. of Health and Human Services, U.S. Government Printing Office, 1991).

Peptides and Peptidomimetics

In certain embodiments, interaction between E-selectin and sLe$^a$ or sLe$^x$ may be inhibited (i.e., inhibited, decreased, disrupted reduced in a biologically or statistically significant manner) by a peptide or peptidomimetic of the portion of E-selectin that binds a compound provided herein. The peptide and the peptide moiety of the peptidomimetic may comprise at least 3, 4, 5, 6, 7, 8, 9, 10, 11, 12, 13, 14, 15, 16-20, 21-25, 26-30, 31-35, 36-40, 41-45, or 46-50 amino acids. Peptides and peptidomimetics typically have molecular masses less than $10^4$ daltons, less than $10^3$ daltons, or less than $10^2$ daltons.

Methods of Use

Methods are provided herein for using any one or more of the E-selectin antagonist agents described above and herein, including glycomimetics of formula (I), antibodies or antigen-binding fragments thereof, polypeptides, peptides and aptamers for preventing (i.e., reducing the likelihood of occurrence or recurrence of) and/or treating a disease or disorder associated with, mediated by, or exacerbated by E-selectin binding to an E-selectin ligand, which in turn causes an undesired biological activity. Thus, the E-selectin antagonists described herein may be used in methods for treating a disease or disorder treatable by inhibiting binding of E-selectin to an E-selectin ligand. These methods and other embodiments are described in greater detail herein.

In certain embodiments, a compound of formula (I) or a pharmaceutical composition comprising the compound may be used in methods for treating and preventing (i.e., decreasing or reducing the likelihood of occurrence of) metastasis of cancer cells (also called tumor cells herein) in an individual (i.e., subject, patient) who is in need thereof by administering the compound or composition to the individual. In other embodiments, a compound of formula (I) or a pharmaceutical composition comprising the compound may be used in methods for inhibiting (reducing, decreasing, or preventing (i.e., decreasing the likelihood of occurrence of)) infiltration of cancer cells into bone marrow in an individual (i.e., subject, patient) who is in need thereof by administering the compound or composition to the individual. In still another embodiment, methods are provided herein for inhibiting (reducing, decreasing, or preventing) adhesion of a cancer cell that expresses a ligand of E-selectin to an endothelial cell expressing E-selectin on the cell surface of the endothelial cell wherein the method comprises contacting the endothelial cell and the compound or composition comprising the compound (i.e., in some manner permitting the compound or composition comprising the compound to interact with the endothelial cell) such that when the compound interacts with E-selectin on the endothelial cell, binding of the cancer cell to the endothelial cell is inhibited. In certain embodiments, the endothelial cell is present in the bone marrow. In other embodiments, an E-selectin antagonist agent selected from an antibody or antigen-binding fragment thereof, polypeptide, peptide and aptamer, which agent is capable of competing with a compound of formula (I), may be used in the aforementioned methods.

In still another embodiment described herein, a method is providing for treating a cancer in an individual (i.e., subject, patient) by administering a compound of formula I or a pharmaceutical composition comprising the compound to the individual. The compound (or pharmaceutical composition comprising the compound) may be administered in conjunction with (i.e., as an adjunct therapy, which is also called adjunctive therapy) with chemotherapy or radiation or both. The chemotherapy or radiation therapy or combination may be referred to as the primary anti-tumor or anti-cancer therapy that is being administered to the individual to treat the particular cancer. In other embodiments, an E-selectin antagonist agent selected from an antibody or antigen-binding fragment thereof, polypeptide, peptide and aptamer, which agent is capable of competing with a compound of formula (I), may be used in the aforementioned methods.

In still another embodiment, a compound of formula I or pharmaceutical compositions comprising the compound may be used in methods for enhancing hematopoietic stem cell survival in a subject. In other embodiments, an E-selectin antagonist agent selected from an antibody or antigen-binding fragment thereof, polypeptide, peptide and aptamer, which agent is capable of competing with a compound of formula (I), may be used in the aforementioned methods.

In another embodiment, a compound of formula I or pharmaceutical compositions comprising the compound may be used in methods for treating or preventing (i.e., decreasing or reducing the likelihood or risk of occurrence of) thrombosis in a subject. In certain embodiments, a compound of formula I or pharmaceutical compositions comprising the compound may be used in methods for treating or preventing (i.e., decreasing or reducing the risk of occurrence of) thrombus formation in an individual who is need of such treatment, comprising administering to the individual a compound having the formula (I) (or the pharmaceutical composition comprising the compound), or any substructure or specific structure described herein. In other embodiments, an E-selectin antagonist agent selected from an antibody or antigen-binding fragment thereof, polypeptide, peptide and aptamer, which agent is capable of competing with a compound of formula (I), may be used in the aforementioned methods.

As understood by a person of ordinary skill in the medical art, the terms, "treat" and "treatment," refer to medical management of a disease, disorder, or condition of a subject (i.e., patient, individual) (see, e.g., Stedman's Medical Dictionary). In general, an appropriate dose and treatment regimen provide at least one glycomimetic compound or other agent described herein in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the disease, condition, or disorder as well as subjects prone to have or at risk of developing the disease, condition, or disorder, and those in which the disease, condition, or disorder is to be prevented (i.e., decreasing the likelihood of occurrence of the disease, disorder, or condition).

Figure 3:
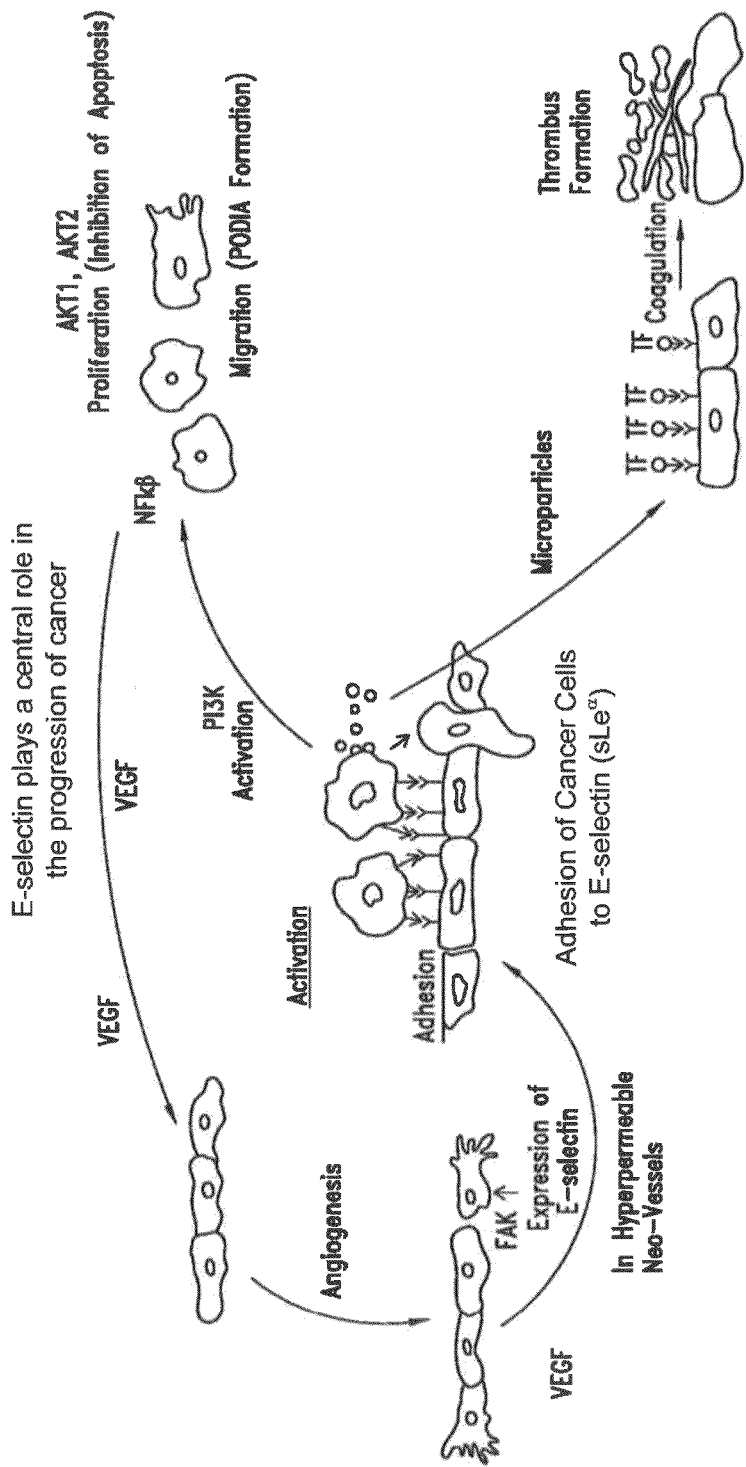
FIG. 3 is a diagram illustrating that E-selectin plays a central role in the progression of cancer.

As discussed in detail herein, the disease or disorder to be treated or prevented (i.e., reduce the likelihood of occurrence or recurrence) is a cancer and related metastasis and includes cancers that comprise solid tumor(s) and cancers that comprise liquid tumor(s). As illustrated in FIG. 3, E-selectin plays a central role in the progression of a cancer. The invasive properties of cancer cells depend, at least in part, on the capability of the cancer cell to breach the endothelial barrier. Cancer cells, for example, colon cancer cells, may express E-selectin ligands that are capable of binding to endothelial cells that express E-selectin on their cell surface. Without wishing to be bound by theory, binding of the cancer cell to the endothelial cell can contribute to extravasation of the cancer cells (see, e.g., Tremblay et al., Oncogene 25: 6563-6573. doi:10.1038/sj.onc.1209664; published online 22 May 2006).

Cancers that may be prevented from metastasizing includes cancers that comprise solid tumors and those that comprise liquid tumors (e.g., hematological malignancies). Examples of solid tumors that may be treated with the agents described herein (e.g., glycomimetic compounds of formula I) include colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors occur in the blood, bone marrow, and lymph nodes and include leukemia (e.g., AML, ALL, CLL, and CML), lymphoma (e.g., non-Hodgkin lymphoma and Hodgkin lymphoma), and myeloma (e.g., multiple myeloma). Reports have described that liquid tumors such as multiple myeloma follow a similar invasion—metastasis cascade as observed with solid tumors and that E-selectin ligands are present on liquid tumor cells, such as myeloma cells (see, e.g., Ghobrial, Blood 120:20-30 (2012) Epub 2012 Apr. 24). Others have observed that ligands of E-selectin (e.g., CD65) may be important for extravascular infiltration of leukemia cells (see, e.g., Noguchi et al., Leukemia Res. 25:847-53 (2001)). Liquid tumor cells may also adhere to bone marrow, which may further lead to sequestration and quiescence of the tumor cells, resulting in "resistance" of the tumor cells to chemotherapy, which phenomenon is referred to as adhesion mediated drug resistance. Studies have also indicated that bone marrow contains anatomic regions that comprise specialized endothelium, which expresses the E-selectin (see, e.g., Sipkins et al., Nature 435: 969-973 (2005)). Accordingly, an E-selectin antagonist, such as those described herein, may be useful for inhibiting metastasis of cancers that comprise either a solid or liquid tumor by inhibiting binding of an E-selectin ligand to E-selectin.

In particular embodiments, the compounds of formula (I), including substructures and specific compounds, and agents described herein may be used for treating or preventing (i.e., decreasing or reducing the likelihood of occurrence of) metastasis of cancer cells in an individual (i.e., subject, patient) who is in need thereof. The compounds and agents described herein may be used for inhibiting or preventing (i.e., decreasing or reducing the likelihood of occurrence of) infiltration of cancer cells into bone marrow in an individual who is in need thereof. The individuals (or subjects) in need of such treatments include subjects who have been diagnosed with a cancer, either a cancer that comprises solid tumor(s) or a cancer that comprises a liquid tumor. Without wishing to be bound by theory, by inhibiting tumor cells from metastasizing to the bone marrow or to other protective niches in the body, the tumor cells are inhibited from sequestration and protection from exposure to chemotherapy or radiotherapy.

Such cancers include, for example, colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors occur in the blood, bone marrow, the soft, sponge-like tissue in the center of most bones, and lymph nodes and include leukemia (e.g., AML, ALL, CLL, and CML), lymphoma, and myeloma (e.g., multiple myeloma). Lymphomas include Hodgkin lymphoma, which is marked by the presence of a type of cell called the Reed-Sternberg cell, and non- Hodgkin lymphomas, which includes a large, diverse group of cancers of immune system cells. Non-Hodgkin lymphomas can be further divided into cancers that have an indolent (slow-growing) course and those that have an aggressive (fast-growing) course, and which subtypes respond to treatment differently.

The compounds of formula I and agents described herein (or the pharmaceutical composition comprising the compound or agent) may be administered as an adjunct therapy to chemotherapy or radiotherapy or both, which is being delivered to the subject as primary therapy for treating the cancer. The chemotherapy and radiotherapy that may be administered depend upon several factors including the type of cancer, location of the tumor(s), stage of the cancer, age and gender and general health status of the subject. A person skilled in the medical art can readily determine the appropriate chemotherapy regimen or radiotherapy regimen for the subject in need. The person skilled in the medical art can also determine, with the aid of preclinical and clinical studies, when the compound of formula (I) or agent should be administered to the subject, that is whether the compound or agent is administered prior to, concurrent with, or subsequent to a cycle of the primary chemotherapy or radiation treatment.

Also provided herein is a method for inhibiting adhesion of a tumor cell that expresses a ligand of E-selectin to an endothelial cell expressing E-selectin on its cell surface, which method comprises contacting the endothelial cell with the compound of formula (I) or agent as described herein, thereby permitting the compound to interact with E-selectin on the endothelial cell surface and inhibiting binding of the tumor cell to the endothelial cell. Without wishing to be bound by theory, inhibiting adhesion of tumor cells to endothelial cells may reduce in a significant manner, the capability of the tumor cells to extravasate into other organs, blood vessels, lymph, or bone marrow and thereby reduce, decrease, or inhibit, or slow the progression of the cancer, including reducing, decreasing, inhibiting, or slowing metastasis.

In particular embodiments of the methods described herein, the subject is a human or non-human animal. A subject in need of the treatments described herein may exhibit symptoms or sequelae of cancer disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of a compound, agent, or pharmaceutical composition described herein in treating or preventing a disease or disorder or condition described herein, and determining and adjusting an appropriate dosing regimen (e.g., adjusting the amount of compound per dose and/or number of doses and frequency of dosing), can readily be determined by a person of ordinary skill in the medical and clinical arts. One or any combination of diagnostic methods, including physical examination, assessment and monitoring of clinical symptoms, and performance of analytical tests and methods described herein, may be used for monitoring the health status of the subject.

As described herein, with respect to treating a subject (i.e., an individual) who has cancer or who is at risk of developing cancer, at least one (i.e., one or more) of the above described agents (e.g., compounds of formula (I)) may be administered in combination with at least one (i.e., one or more) additional anti-cancer agent. Chemotherapy may comprise one or more chemotherapeutic agents. For example, chemotherapy agents, radiotherapeutic agents, inhibitors of phosphoinositide-3 kinase (PI3K), and inhibitors of VEGF may be used in combination with an agent described herein. Examples of inhibitors of PI3K include the compound named by Exelixis as "XL499." Examples of VEGF inhibitors include the compound called "cabo" (previously known as XL184). Many other chemotherapeutics are small organic molecules. As understood by a person skilled in the art, chemotherapy may also refer to a combination of two or more chemotherapeutic molecules that are administered coordinately and which may be referred to as combination chemotherapy. Numerous chemotherapeutic drugs are used in the oncology art and include, for example, alkylating agents; antimetabolites; anthracyclines, plant alkaloids; and topoisomerase inhibitors.

An E-selectin antagonist, such as a glycomimetic compound of formula (I) may function independent of the anti-cancer agent, or may function in coordination with the anti-cancer agent, e.g., by enhancing effectiveness of the anti-cancer agent or vice versa. In one embodiment, methods are provided for treating cancers comprising administering the E-selectin antagonists described herein (including the glycomimetic compounds of formula I). The cancer may be a solid tumor or a liquid tumor. In certain embodiments, the E-selectin antagonist is used in combination with chemotherapy, radiation, or both chemotherapy and radiation. The E-selectin antagonist may be administered with one or more cycles (i.e., one, two, three, four, five, six, or more cycles) of chemotherapy or radiotherapy when multiple cycles of the chemotherapy or radiotherapy are administered to a subject for the treatment of a cancer. The E-selectin antagonist may enhance the efficacy of the chemotherapeutic agent(s) or radiotherapy.

In another embodiment, provided herein are methods for enhancing (i.e., enhancing, promoting, improving the likelihood of, enhancing in a statistically or biologically significant manner) or maintaining survival of hematopoietic stem cells (HSC) in a subject who is treated with or will be treated with a chemotherapeutic drug(s) or radioactive therapy, respectively, comprising administering one or more of the E-selectin antagonist glycomimetic compounds described herein. In certain embodiments, the subject receives or will receive both chemotherapy and radiation therapy. Also, provided herein is a method for reducing (i.e., reducing, inhibiting, diminishing in a statistically or biologically significant manner) chemosensitivity or radiosensitivity of hematopoietic stem cells (HSC) to the chemotherapeutic drug(s) or radioactive therapy, respectively, in a subject. Because repeated cycles of chemotherapy and radiotherapy often diminish the ability of HSCs to recover and replenish bone marrow, the glycomimetic compounds described herein may be useful for subjects who will receive more than one cycle, such as at least two, three, four or more cycles, of chemotherapy or radiotherapy or a combination of both chemotherapy and radiotherapy. The E-selectin antagonist may therefore be administered with any one or more of each of the cycles of chemotherapy or radiotherapy (or combination) administered to the subject. HSCs reside in the bone marrow and generate the cells that are needed to replenish the immune system and the blood. Anatomically, bone marrow comprises a vascular niche that is adjacent to bone endothelial sinuses (see, e.g., Kiel et al., *Cell* 121:1109-21 (2005); Sugiyama et al., *Immunity* 25:977-88 (2006); Mendez-Ferrer et al., *Nature* 466:829-34 (2010); Butler et al., *Cell Stem Cell* 6:251-64 (2010)). A recent study describes that E-selectin promotes HSC proliferation and is an important component of the vascular niche (see, e.g., Winkler et al., *Nature Medicine* published online 21 Oct. 2012; doi:10.1038/nm.2969; see also, e.g., Int'l. Patent Appl. Publ.

No. 2007/028050). Deletion or inhibition of E-selectin enhanced HSC survival in mice that were treated with chemotherapeutic agents or radiotherapy and accelerated blood neutrophil recovery (see, e.g., Winkler et al., supra).

An agent described herein (i.e., an E-selectin antagonist, such as a glycomimetic compound of formula (I)) may function independent of the anti-cancer agent, or may function in coordination with the anti-cancer agent, e.g., by enhancing effectiveness of the anti-cancer agent or vice versa. In addition, the administration of one or more of the E-selectin antagonist agents described herein may be in conjunction with one or more other therapies, e.g., for reducing toxicities of therapy. For example, at least one (i.e., one or more) palliative agent to counteract (at least in part) a side effect of therapy (e.g., anti-cancer therapy) may be administered. Agents (chemical or biological) that promote recovery, or counteract side effects of administration of antibiotics or corticosteroids, are examples of such palliative agents. At least one agent described herein may be administered before, after, or concurrently with administration of at least one additional anti-cancer agent or at least one palliative agent to reduce a side effect of therapy. Where administration is concurrent, the combination may be administered from a single container or two (or more) separate containers.

Cancer cells (also called herein tumor cells) that may be prevented (i.e., inhibited, slowed) from metastasizing, may be killed, may be prevented from adhering to an endothelial cell, or inhibited from infiltrating bone marrow include cells of solid tumors and liquid tumors (including hematological malignancies). Examples of solid tumors are described herein and include colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors occur in the blood, bone marrow, and lymph nodes and include leukemia (e.g., AML, ALL, CLL, and CML), lymphoma (e.g., Hodgkin lymphoma and non-Hodgkin lymphoma), and myeloma (e.g., multiple myeloma). As used herein, the term cancer cells include mature, progenitor and cancer stem cells.

Bones are a common location for cancer to infiltrate once leaving the primary tumor location. Once cancer resides in bone, it is frequently a cause of pain to the individual. In addition, if the particular bone affected is a source for production of blood cells in the bone marrow, the individual may develop a variety of blood cell related disorders. Breast and prostate cancer are examples of solid tumors that migrate to bones. Acute myelogenous leukemia (AML) and multiple myeloma (MM) are examples of liquid tumors that migrate to bones. Cancer cells that migrate to bone will typically migrate to the endosteal region of the bone marrow. Once cancer cells have infiltrated into the marrow, the cells become quiescent and are protected from chemotherapy. The compounds of the present invention block infiltration of disseminated cancer cells into bone marrow. A variety of individuals may benefit from treatment with the compounds. Examples of such individuals include individuals with a cancer type having a propensity to migrate to bone where the tumor is still localized or the tumor is disseminated but not yet infiltrated bone, or where individuals with such a cancer type are in remission.

The cancer patient population most likely to respond to treatment using the agents (e.g., compounds of formula (I)) described herein can be identified based on the mechanism of action of E-selectin. That is, patients may be selected that express a highly active E-selectin as determined by the genetic polymorphism for E-selectin of S128R (Alessandro et al., Int. J. Cancer 121:528-535, 2007). In addition, patients for treatment by the agents described herein may also selected based on elevated expression of the E-selectin binding ligands (sialyl $Le^a$ and sialyl $Le^x$) as determined by antibodies directed against cancer-associated antigens CA-19-9 (Zheng et al., World J. Gastroenterol. 7:431-434, 2001) and CD65. In addition, antibodies HECA-452 and FH-6 which recognize similar carbohydrate ligands of E-selectin may also be used in a diagnostic assay to select the cancer patient population most likely to respond to this treatment.

In other embodiments, methods are provided for treating or preventing (i.e., reducing the likelihood of occurrence) thrombosis in a subject (i.e., individual, patient) in need thereof. The subject may have a thrombus or may be at risk of developing a thrombus. An E-selectin antagonist described herein (including a compound of formula (I)) may inhibit or prevent (i.e., reduce the likelihood of occurrence of) the formation of a thrombus. The E-selectin antagonist may inhibit slow or retard formation of a thrombus or decrease the size or integrity of a formed thrombus. While this method is applicable to individuals in need thereof generally, the methods are especially advantageous for such individuals who are also at risk for bleeding. For example, this method is useful and advantageous in a wide variety of situations in which the risk of bleeding is significant and the use of anti-thrombosis agents with anti-coagulant properties (such as LMW heparin) is contraindicated. Even when the use of an anti-thrombosis agent with anti-coagulant properties is not believed to be contraindicated, this method provides a benefit if bleeding nevertheless occurs. The E-selectin antagonists used in the method are agents that inhibit the interaction of E-selectin with sialyl $Le^a$ ($sLe^a$) or sialyl $Le^x$ ($sLe^x$), but in contrast to agents, such as heparin, do not significantly delay clotting.

Selectin-mediated activation of leukocytes promotes formation of procoagulant microparticles rich in tissue factor (see, e.g., Wakefield et al., Thrombosis Res. 123:S3. 5-40 (2009)). Both E and P-selectins are expressed on the endothelium after injury or activation of the blood vessel wall. Many reports have focused on the role of P-selectin in thrombosis, in part due to the availability of inhibitors for P-selectin (see, e.g., Lopez et al., Hematology Am. Soc. Hematol. Educ. Program 439-56 (2004)); however, several studies conclude E-selectin has a dominant role. Without wishing to be bound by any particular theory, the formation of VTE is driven by the inflammatory response, and the selectins function in early events of thrombosis.

Various drugs are currently used for the treatment of thrombosis. Exemplary drugs include those that suppress platelet aggregation (anti-platelet therapeutics), for example, aspirin, ticlopidine, eicosapentaenoic acid (EPA), dipyridamole, and dilazep hydrochloride. An anti-platelet therapeutic such as aspirin suppresses formation of thrombus at the impaired site of the blood vessel by suppressing development of blood coagulation triggered by platelet aggregation. However, because platelets also prevent hemorrhage from the blood vessel, excessive suppression of the platelet can result in decreased effectiveness of platelets in preventing hemorrhage.

Anticoagulants used for treatment or prevention of thrombosis act by suppressing a blood coagulation factor and include warfarin, heparin, low molecular weight heparin, and argatroban. Anticoagulants are useful in preventing formation of intravascular fibrin clots, whereas fibrinolytics (e.g., plasminogen activators) are useful for dissolution of fibrin clots. Uncontrolled bleeding may occur after long-term administration of large doses of an anticoagulant or fibrinolytic. When heparin is used, complications include heparin resistance, bleeding, heparin-induced thrombocytopenia, and osteoporosis.

E-selectin, in particular, plays a dominant role in thrombus formation, which was determined in animal models and by studying humans who have a genetic polymorphism (Ser128Arg) of E-selectin. In human studies, a single nucleotide polymorphism (SNP) S128R (serine to arginine at position 128) in the E-selectin gene is reported to be overrepresented in patients with atherosclerosis, restenosis, coronary heart disease, myocardial infarction, and colorectal cancer with poor prognosis (Myers et al., *J. Surg. Res.* 108:212-21 (2002)). S128R E-selectin is a genetic variant that is more active than normal (i.e., wild-type) E-selectin. Cells expressing S128R E-selectin show greater adhesion and adhere to a wider variety of cell types (Yoshida et al., *Arterioscler. Thromb. Vasc. Biol.* 23:783-88 (2003)). According to publications and a screen by the Consortium of Functional Glycomics, S128R E-selectin binds to the same carbohydrates (sialyl Le$^a$ and sialyl Le$^x$) as the wild type E-selectin, although its binding activity in other in vitro assays is enhanced and perhaps more promiscuous.

In a study on the effects of S128R E-selectin on venous thromboembolism (VTE), 585 patients were prospectively observed after the first VTE for recurrence after discontinuation of treatment (see, e.g., Jilma et al., *Arch. Intern. Med.* 166:1655-59 (2006)). Patients with S128R E-selectin showed a significant increase in developing another thrombus after stopping anticoagulant therapy when compared to patients with wild type E-selectin.

In an embodiment, the thrombosis is a venous thromboembolism (VTE). VTE causes deep vein thrombosis and pulmonary embolism. Low molecular weight (LMW) heparin is the current mainstay therapy for the prevention and treatment of VTE. There are many circumstances, however, when the use of LMW heparin is contraindicated. Patients undergoing surgery, patients with thrombocytopenia, patients with a history of stroke and many cancer patients are just a few examples where the use of heparin should be avoided due to the risk of bleeding.

As evidenced herein, administration of a compound of formula I significantly inhibited VTE in an in vivo treatment model of thrombus formation under continuous blood flow without an increased bleeding risk. Effects of the compound in this treatment model are comparable to the standard of care using LMW heparin. However, LMW heparin is a known anti-coagulant and delays clotting over four times longer than control bleeding times. Also as described herein, the compound of formula I only slightly delays clotting and is a significant improvement in reducing bleeding time over LMW heparin. Accordingly, the agents described herein may be useful when the risk of bleeding is not significant, but also may be useful in a wide variety of situations when the risk of bleeding is significant, and particularly when use of anti-thrombosis agents with anti-coagulant properties (such as LMW heparin) is contraindicated.

At least one (i.e., one or more) of the above described agents (i.e., an E-selectin antagonist, such as a glycomimetic compound of formula (I)) may be administered in combination with at least one (i.e., one or more) additional anti-thrombosis agent. An agent described herein (i.e., an E-selectin antagonist) may function independent of the anti-thrombosis agent, or may function in coordination with the anti-thrombosis agent. In addition, the administration of one or more of the agents described herein may be in conjunction with one or more other therapies, e.g., for reducing toxicities of therapy. For example, at least one palliative agent to counteract (at least in part) a side effect of therapy may be administered. Agents (chemical or biological) that promote recovery, or counteract side effects of administration of antibiotics or corticosteroids, are examples of such palliative agents. At least one agent described herein may be administered before, after or concurrently with administration of at least one additional anti-thrombosis agent or at least one palliative agent to reduce a side effect of therapy. Where administration is concurrent, the combination may be administered from a single container or two (or more) separate containers.

A wide variety of individuals are candidates for treatment as described herein. Thrombus formation may occur in infants, children, teenagers and adults. An individual may have a hereditary predisposition to thrombosis. Thrombosis may be initiated, for example, due to a medical condition (such as cancer or pregnancy), a medical procedure (such as surgery) or an environmental condition (such as prolonged immobility). Other individuals at risk for thrombus formation include those who have previously presented with a thrombus.

In particular embodiments of the methods described herein, the subject is a human or non-human animal. A subject in need of the treatments described herein may exhibit symptoms or sequelae of thrombosis disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of a compound, agent, or pharmaceutical composition described herein in treating or preventing a disease or disorder or condition described herein, and determining and adjusting an appropriate dosing regimen (e.g., adjusting the amount of compound per dose and/or number of doses and frequency of dosing), can readily be determined by a person of ordinary skill in the medical and clinical arts. One or any combination of diagnostic methods, including physical examination, assessment and monitoring of clinical symptoms, and performance of analytical tests and methods described herein, may be used for monitoring the health status of the subject.

Methods for Characterizing Therapeutic Agents

Characterizing at least one biological activity of a therapeutic agent described herein may be determined by performing one or more in vitro and in vivo studies routinely practiced in the art and described herein or in the art. In vitro assays include without limitation binding assays, immunoassays, competitive binding assays and cell based activity assays. Animal model studies may also be performed, which are typically rodent animal studies described in the art or routinely developed or adapted by a person skilled in the art to characterize an agent, including determining efficacy, in vivo. Non-human primate animal models may be used in pre-clinical studies that precede clinical studies; however, these animal models are not typically employed in the same routine manner as rodent animal studies designed for assessing the effectiveness or other characteristics of a therapeutic. Persons skilled in the art of design and execution of animal model studies can also readily determine the appropriate control groups to include with the studies as well as determine the appropriate statistical analysis or analyses for evaluating the data.

An inhibition assay may be used to screen for antagonists of E-selectin. For example, an assay may be performed to characterize the capability of a compound or other agent described herein to inhibit (i.e., reduce, block, decrease, or prevent in a statistically or biologically significant manner) interaction of E-selectin with $sLe^a$ or $sLe^x$. The inhibition assay may be a competitive binding assay, which allows the determination of $IC_{50}$ values. By way of example, the method comprises immobilizing E-selectin/Ig chimera onto a matrix (e.g., a multi-well plate, which are typically made from a polymer, such as polystyrene; a test tube, and the like); adding a composition to reduce nonspecific binding (e.g., a composition comprising non-fat dried milk or bovine serum albumin or other blocking buffer routinely used by a person skilled in the art); contacting the immobilized E-selectin with the candidate agent in the presence of $sLe^a$ comprising a reporter group under conditions and for a time sufficient to permit $sLe^a$ to bind to the immobilized E-selectin; washing the immobilized E-selectin; and detecting the amount of $sLe^a$ bound to immobilized E-selectin. Variations of such steps can be readily and routinely accomplished by a person of ordinary skill in the art.

A person skilled in the art is also familiar with assays and animal models to assess whether an E-selectin antagonist is free of significant anti-coagulation properties. For example, an assay that determines the time required to form a clot may be used to screen for or characterize the capability of an E-selectin antagonist to significantly delay clotting, wherein an agent that exhibits reduced, absent, or lack of capability to delay clotting is desired. By way of example, bleeding times may be evaluated in rodents that are injected with a test E-selectin antagonist or a control, and bleeding times recorded after a tail vein is nicked and the tail immersed in isotonic saline.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of an agent that is characterized by one or more assays and techniques described herein and in the art may be a biological sample that is obtained from a subject who has been treated with the agent. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In certain embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like.

Exemplary animal models are described herein and in the art for determining the effectiveness of an E-selectin antagonist. Numerous cancer animal models are routinely practiced in the art. By way of non-limiting examples, models of ALL, multiple myeloma, AML and solid tumor cancer models are available for determining the effectiveness of an E-selectin antagonist. Typically, animals are engrafted with a tumor cell line (such as without limitation, a pancreatic, breast, colon, ovarian, ALL, AML, multiple myeloma tumor cell line) and an agent of interest is administered prior to engraftment, during tumor growth, and/or after a tumor has been established. Numerous statistical analyses are available and understood by a person skilled in the art and may be applied to compare the effect of an agent to one or more appropriate controls.

Pharmaceutical Compositions and Methods of Using Pharmaceutical Compositions

Also provided herein are pharmaceutical compositions that comprise any one or more of the E-selectin antagonist agents described herein, such as one or more of the glycomimetic compounds of formula I (and substructures and specific structures thereof) described herein. The compounds, isolated antibodies and other E-selectin antagonists described herein may also be prepared for pharmaceutical use in a subject, including a human subject. The compounds described herein may be formulated in a pharmaceutical composition for use in treatment or preventive (or prophylactic) treatment (e.g., reducing the likelihood of occurrence or of exacerbation of a disease, or of one or more symptoms of the disease). The methods and excipients described herein are exemplary and are in no way limiting.

In pharmaceutical dosage forms, any one or more of the glycomimetic compounds of formula I, substructures and specific structures described herein may be administered in the form of a pharmaceutically acceptable derivative, such as a salt, or they may also be used alone or in appropriate association, as well as in combination, with other pharmaceutically active compounds. By way of example, as described herein with respect to methods of use, an E-selectin antagonist may be administered to a subject who is also receiving chemotherapy, radiotherapy, a combination or chemotherapy and radiotherapy.

An effective amount or therapeutically effective amount refers to an amount of a glycomimetic compound or a composition comprising one or more compounds; or one or more isolated antibodies (or other E-selectin antagonist agent) that when administered to a subject, either as a single dose or as part of a series of doses, is effective to produce a desired therapeutic effect. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, or blood volume of the subject. In general, the amount of a compound described herein, that is present in a dose, ranges from about 0.01 µg to about 1000 µg per kg weight of the host. In general, the amount of a polypeptide or peptide, or an antibody or antigen-binding fragment thereof, as described herein, present in a dose, also ranges from about 0.01 µg to about 1000 µg per kg of subject. The use of the minimum dose that is sufficient to provide effective therapy is usually preferred. Subjects may generally be monitored for therapeutic effectiveness using assays suitable for the disease or condition being treated or prevented, which assays will be familiar to those having ordinary skill in the art and are described herein. The level of a compound or polypeptide that is administered to a subject may be monitored by determining the level of the compound, peptide, antibody or antigen-binding fragment thereof, or polypeptide (or a metabolite of any of the aforementioned molecules) in a biological fluid, for example, in the blood, blood fraction (e.g., serum), and/or in the urine, and/or other biological sample from the subject. Any method practiced in the art to detect the molecule may be used to measure the level of the molecule during the course of a therapeutic regimen.

The dose of a compound, peptide, antibody or antigen-binding fragment thereof, or polypeptide described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in a manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively deliver an effective amount of the compound. Such administrative routes include, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. Compositions administered by these routes of administration and others are described in greater detail herein.

A pharmaceutical composition may be a sterile aqueous or sterile non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds and polypeptides or peptides described herein may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, $21^{st}$ Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, at least one of the E-selectin antagonist agents described herein can be used alone or in combination with appropriate additives to make tablets, powders, granules or capsules, for example, with any one or more conventional additives, disintegrators, lubricants, and if desired, diluents, buffering agents, moistening agents, preservatives, coloring agents, and flavoring agents. The compositions may be formulated to include a buffering agent to provide for protection of the active ingredient from low pH of the gastric environment and/or an enteric coating. A composition may be formulated for oral delivery with a flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The compositions may be formulated into pressurized acceptable propellants such as dichlorodifluoromethane, propane, nitrogen and the like.

Any one or more of the E-selectin antagonist agents described herein may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneräs et al., *J. Pharm. Pharmacol.* 54:499-508 (2002); Karande et al., *Pharm. Res.* 19:655-60 (2002); Vaddi et al., *Int. J. Pharm.* 91:1639-51 (2002); Ventura et al., *J Drug Target* 9:379-93 (2001); Shokri et al., *Int. J. Pharm.* 228(1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192:147-58 (1999).

Kits with unit doses of one or more of the compounds, polypeptides, peptides, aptamers, antibodies and antigen binding fragments thereof described herein, usually in oral or injectable doses, are provided. Such kits may include a container containing the unit dose, an informational package insert describing the use and attendant benefits of the therapeutic in treating the pathological condition of interest, and optionally an appliance or device for delivery of the composition.

EXAMPLES

Example 1

Synthesis of E-Selectin Inhibitor

Exemplary glycomimetic compounds of formula I were synthesized as described in this Example and as shown in the exemplary synthesis schemes set forth in FIGS. 1-2.

Synthesis of Compound 2

Compound 1 (60 g) was suspended in $H_2O$ (800 ml) and cooled to 0° C. Solid $NaHCO_3$ (120 g) was added in portion with stirring and then a solution of KI (474.3 g) and $I_2$ (127 g) in $H_2O$ (800 ml) was added with stirring. Reaction mixture was stirred at room temperature overnight in the dark. Reaction mixture was then extracted with $CH_2Cl_2$ (3×500 ml). The organic layer was washed with $Na_2S_2O_3$ solution (2×500 ml) and then the combined aqueous layers were extracted with $CH_2Cl_2$ (2×300 ml). Organic layers (2100 ml) were combined and washed with cold $H_2O$ (1×500 ml) and cold brine (1×500 ml). The organic layer was dried over $Na_2SO_4$, filtered, and concentrated to dryness to give compound 2 as light yellow crystals (119 g). Purity: >95% by TLC.

Synthesis of Compound 3

To a solution of compound 2 (119 g) in THF (1600 ml) was added DBU (119 ml) with stirring at room temperature and the reaction mixture was gently refluxed overnight with stirring. Some precipitate forms and TLC showed no starting material left. The reaction mixture was concentrated to dryness and dissolved in EtOAc (300 ml), washed with 0.5 M HCl (200 ml) until pH 2-3 of the aqueous wash, and then the organic layer was further washed with $H_2O$ (200 ml). Aqueous layers were combined and extracted with EtOAc (3×200 ml) to produce a second organic layer. Combined organic layers (900 ml) were washed with brine, dried ($Na_2SO_4$), filtered and concentrated to dryness to give compound 3 (58 g). Purity: >95% by TLC.

Synthesis of Compound 4

To a solution of compound 3 (58 g) in MeOH (800 ml) was added $NaHCO_3$ (47 g) with stirring. The reaction mixture was stirred under gentle reflux for 3 h, cooled to room temperature, filtered and concentrated to dryness. The residue was dissolved in EtOAc (300 ml) and washed with $H_2O$. Aqueous layer was extracted with EtOAc (3×100 ml). Combined organic layers (600 ml) were washed with 0.5M HCl (200 ml), $H_2O$ (100 ml), and brine (100 ml), dried ($Na_2SO_4$), filtered, and concentrated to dryness. The residue was purified by column chromatography ($SiO_2$, Hexanes-EtOAc 3:1→3:2) to give compound 4 (54 g). Purity: >95% by TLC.

Synthesis of Compound 5

Compound 4 (31 g) was dissolved in tBuOMe (620 ml) and vinylacetate (166 ml) added with vigorous stirring. Novozyme 435 (1.4 g) was added and vigorous stirring continued for 5.5 h. The reaction mixture was filtered and stored at −20° C. After 12-18 hours, another batch of Novozyme 435 resin (1.4 g) was added and stirred vigorously for 8 h. Resin was filtered and concentrated to dryness. Oily residue was purified by CombiFlash® system (silica) using 0→50% EtOAc/Hexanes to give compound 5 (13.0 g).

Synthesis of Compound 6

Compound 5 (13.5 g) was dissolved in $CH_2Cl_2$ (300 ml) under argon and TBDMS-Cl (26.4 g) added with stirring at room temperature under argon. DBU (32.4 ml) was added and stirring continued for overnight at room temperature under argon. MeOH (30 ml) was added and washed with cold saturated solution of $NaHCO_3$ (200 ml), brine (150 ml). The organic layer was dried (Na2SO4), filtered and concentrated to dryness. The residue was purified by CombiFlash® system ($SiO_2$) using solvent EtOAc-Hexanes (0-15%) to give compound 6 (18 g). Purity >95% by TLC.

Synthesis of Compound 7

Compound 6 (12 g) was dissolved in $CH_2Cl_2$ (400 ml) and cooled to 0° C. m-chloroperbenzoic acid (77%, 19 g) was added and the solution stirred for few hours during which the temperature of the reaction mixture reached to room temperature. The stirring was continued overnight at room temperature. CH$_2$Cl$_2$ (300 ml) was added and washed with cold saturated solution of NaHCO$_3$ (3×400 ml), brine (cold), dried (Na$_2$SO4), filtered, and concentrated to dryness. The residue was purified by CombiFlash® system (SiO$_2$) using EtOAc-Hexanes (0→30%) to give 7 (9 g). Purity: >95% by TLC.

Synthesis of Compound 8

All operation of this step was done in argon atmosphere. CuCN (9.42 g) was dried at 160° C. under vacuum for 40 min, cooled down to room temperature and suspended in THF (80 ml). The mixture was cooled down to −78° C. During this time, tetravinyltin (12 ml) and n-BuLi in hexane (2.5 M, 100 ml) were reacted for 30 min at 0° C. in THF (30 ml). This solution was added to the mixture of CuCN in THF, and the resulting mixture was stirred for 30 min. at −20° C. The mixture was then cooled to −78° C. and to which was added a solution of freshly distilled BF$_3$.Et2O (6 ml) in THF (20 ml). The mixture was stirred for 20 min. at −78° C. Compound 7 (5 g) in THF (40 ml) was added and the reaction mixture was stirred at −78° C. for 5 h. MeOH (7 ml) and Et$_3$N (3 ml) was added and the mixture was concentrated to dryness. The residue was dissolved in EtOAc (200 ml) and washed with saturated solution of NaHCO$_3$ (2×100 ml), brine (100 ml), dried (Na$_2$SO$_4$), filtered, and concentrated to dryness. The residue was purified by CombiFlash® system (SiO2) using solvent EtOAc-Hexanes (0→5%) to give compound 8 (2.5 g).

Synthesis of Compound 10

Compound 8 (2.25 g, 7 mmol) was dissolved in toluene (7 ml) and solvent evaporated off. The process was repeated twice and finally dried under vacuum for 15 min. The residue was dissolved in anhydrous CH$_2$Cl$_2$ (45 ml) and DMF (45 ml) was added. The solution was stirred under argon at room temperature and molecular sieves (3 g, 4 Å, powdered and flamed dried) added. Et$_4$NBr (3.3 g, 15.7 mmol, 2.2 equivalents, dried at 200° C. for 2 h) was added and the stirring continued for 1 h at room temperature under argon.

Compound 9 (5.13 g, 10 mmol, 1.42 equivalents) was co-evaporated with toluene (3×20 ml), dried under vacuum, and dissolved in CH$_2$Cl$_2$ (45 ml). The reaction mixture was placed in an ice-bath and stirred for 10 min. To this solution was added Br$_2$ (0.8 ml, 15 mmol, 1.5 equivalents) drop-wise with stirring in the ice-bath. Stirring was continued for 40 min at the same temperature. The ice-bath was removed and cyclohexene (2.1 ml) added slowly with stirring after 10 min. The reaction mixture was stirred for 10 min. and added slowly to the reaction mixture above with stirring at room temperature under argon. Stirring continued for 17 h and then pyridine (4 ml) was added, filtered and the filtrate concentrated to dryness. The residue was dissolved in CH$_2$Cl$_2$ (100 ml) and transferred to a separatory funnel. The organic layer was washed with cold brine (2×75 ml), dried (Na$_2$SO$_4$), filtered and concentrated to dryness, co-evaporated with toluene (3×50 ml), and dried under vacuum. The residue was dissolved in THF (8 ml) and a solution of TBAF (1 M in THF, 10 ml, 10 mmol, 1.42 equivalents) added with stirring at room temperature. Stirring was continued for 15 h and solvent evaporated off. The residue was dissolved in CH$_2$Cl$_2$ (100 ml) and transferred to a separatory funnel, washed with cold brine (2×75 ml), dried (Na$_2$SO$_4$), filtered, and concentrated to dryness. The residue was purified by column chromatography (Hexanes-Ethyl acetate from 100% hexanes to 70% hexanes in EtOAc) to give compound 10 (1.6 g, 2.59 mmol, 37% overall in two steps). TLC: 5% EtOAc in hexanes and 33% EtOAc in hexanes.

Synthesis of Compound 12

Commercially available compound 11 (10 g) was dried overnight under vacuum overnight and added to a solution of NaOMe (5M, 10 ml) in MeOH (200 ml) with stirring at room temperature under argon. Stirring was continued for overnight at room temperature argon, and Et$_3$N (7 ml) was added followed by allylchloroformate (3.5 ml) dropwise. Stirring was continued for 6 h at room temperature under argon. The reaction mixture was concentrated to dryness and dissolved in pyridine (100 ml). Ac$_2$O (50 ml) was added at room temperature under argon and stirred at room temperature for overnight. The reaction mixture was concentrated to dryness and purified by column chromatography on CombiFlash® system using EtOAc-Hexanes (0-100%). The desired fractions were collected and concentrated to dryness to give Compound 12 (10.2 g).

Synthesis of Compound 13

Compound 12 (7.5 g) was dissolved in DMF (140 ml) to which was added NH$_4$OAC (4.05 g) with stirring. Stirring was continued for overnight at room temperature under argon. The next day the reaction mixture was stirred at 50° C. under argon for 8 h. The reaction mixture was concentrated to dryness and the residue dissolved in EtOAc (150 ml), washed with brine (100 ml), dried (Na$_2$SO4), filtered, and concentrated to dryness. The residue was purified by column chromatography (SiO$_2$, Hexanes-EtOAc 2:1→1:2) to give Compound 13 (6 g).

Synthesis of Compound 14

Compound 13 (6 g) was dissolved in CH$_2$Cl$_2$ (50 ml) to which was added CCl$_3$CN (6 ml) and DBU (0.5 ml). The reaction mixture was stirred at room temperature for 0.5 h, solvent was evaporated off and the residue was purified by column chromatography (silica gel) to give Compound 14 (4.5 g).

Synthesis of Compound 15

Compound 10 (2 g) and compound 14 (2.1 g) was dissolved in CH$_2$Cl$_2$ (40 ml). To this solution were added molecular sieves (4 Å, 0.8 g) and stirred at room temperature for 30 min. The solution was then cooled to 0° C. and BF$_3$Et$_2$O (0.25 ml dissolved in 5 ml) is added with stirring at 0° C. The reaction mixture was stirred at 0° C. for 2 h. Et$_3$N (0.5 ml) was added and the solvent was evaporated off. The residue was purified by column chromatography (silica gel) to give Compound 15 (1.8 g).

Synthesis of Compound 16

Compound 15 (1.7 g) was treated with 0.01N NaOMe in MeOH (10 ml) for 2 h and neutralized with IR-120 (H$^+$) resin, filtered, and concentrated to dryness to give Compound 16 (1.25 g).

Synthesis of Compound 17

To a solution of compound 16 (1.2 g) in CH$_3$CN (30 ml) was added Et3N (0.28 ml) and cooled to 0° C. To this solution was added BzCN (0.35 mg in 10 ml CH₃CN) dropwise during 20 min at 0° C. The reaction mixture was stirred for 1 h at 0° C. and concentrated to dryness. The residue was purified by column chromatography (silica gel) to give compound 17 (0.95 g).

Synthesis of Compound 19

Compound 17 (0.9 g) was dissolved in MeOH (12 ml). To this solution was added Bu₂SnO (0.4 g) and the mixture was refluxed for 2 h. Solvent was evaporated off and the residual solvent was co-evaporated off with toluene 3 times. The residue was dissolved in dimethoxy ethane (15 ml). To this solution was added CsF (0.8 g) and compound 18 (2.1 g, synthesized as described previously, J. Med Chem. 42:4909, 1999). The reaction mixture was stirred overnight at room temperature, and the solvent was evaporated off. The residue was purified by column chromatography to give compound 19 (0.8 g).

Synthesis of Compound 20

Compound 19 (0.7 g) was dissolved in CH₂Cl₂ (20 ml). To this solution was added Pd(Ph)₄ (0.14 g), Bu₃SnH (0.15 ml), and Ac₂O (0.3 ml) and the reaction mixture is stirred at room temperature for 1 h. Solvent was evaporated off and the residue was purified by column chromatography (silica gel) to give compound 20 (0.5 g).

Synthesis of Compound 21

To a solution of compound 20 (0.45 g) in dioxane-H₂O—AcOH (10:2:1, 2.6 ml) was added 10% Pd—C (0.15 g), and the reaction mixture was shaken at room temperature under positive pressure (20 psi) of hydrogen for 5 h. The solid was filtered off, and the filtrate was concentrated to dryness. The residue was purified by column chromatography (silica gel) to give Compound 21 (0.3 g).

Synthesis of Compound 22

Compound 21 (0.28 g) was treated with 0.025 N NaOMe in MeOH (5 ml) for 4 h, neutralized with IR-120 (H+) resin, filtered, and the filtrate was concentrated to dryness to give compound 22 (0.21 g).

Synthesis of Compound 23

Compound 22 (0.18 g) was dissolved in ethylenediamine (2 ml) and stirred at 80° C. for 8 h. Solvent was evaporated off and the residue purified using Sep-pak C18 cartridges to give compound 23 (0.15 g).

Synthesis of Compound 25

Compound 23 (200 mg) was dissolved into 1 mL DMF. To this solution was added commercially available compound 24 (400 mg). Triethyl amine (100 µL) was added dropwise to the react reaction mixture to adjust the pH to 10. The reaction mixture was stirred at room temperature for 1 h. After evaporation to dryness, the residue was purified by HPLC to afford compound 25 (200 mg). See FIG. 1D.

Synthesis of Compound 45

Compound 25 (300 mg) was dissolved into 3 mL DMF. Diisopropylethylamine (60 µL) and HATU (131 mg) were added at room temperature. After stirring for 5 minutes, dimethylamine (2.3 mL, 2M solution in THF) was added dropwise. The reaction was stirred at room temperature for 1 hour. The reaction mixture was concentrated to dryness in vacuo. The residue was dissolved in water and loaded onto a 10 g C-18 cartridge. Elution with water followed by 1/1 water/MeOH afforded compound 45 (100 mg). m/z calculated for $C_{62}H_{114}N_4O_{26}$=1330.8. Found=1353.6 (M+Na). ¹H NMR 400 MHz (D₂O, set at 4.80 ppm) δ0.87 (t, J=7.6 Hz, 3H), 0.94-0.99 (m, 2H), 1.20-1.25 (m, 4H), 1.25 (d, J=6.4 Hz, 3H), 1.26-1.45 (m, 4H), 1.52-1.73 (m, 6H), 1.79-1.88 (m, 3H), 2.00 (s, 3H), 2.11-2.19 (br d, 1H), 2.33 (tt, J=12.4 Hz, J=3.2 Hz, 1H), 2.53 (t, J=6.4 Hz, 2H), 2.95 (s, 3H), 3.06 (s, 3H), 3.28 (t, J=12.5 Hz, 1H), 3.31-3.38 (m, 8H), 3.51-3.54 (m, 2H), 3.61 (dd, J=8.0 Hz, J=0.8 Hz, 1H), 3.63 (dd, J=8.0 Hz, J=2.0 Hz, 11H), 3.70 (s, 44H), 3.73-3.76 (m, 1H), 3.78 (t, J=6.0 Hz, 1H), 3.81-3.82 (m, 1H), 3.88 (dd, J=8.0 Hz, J=3.6 Hz, 1H), 3.99 (bs, 1H), 4.54 (dd, J=8.8 Hz, J=2.0 Hz, 2H), 4.91 (q, J=6.8 Hz, 1H), 5.04 (d, J=3.6 Hz, 1H).

Synthesis of Compound 26

Compound 26 was synthesized as described for compound 25 (see FIG. 1D) except that the PEG reactant had an n of 8 (i.e., 8 repeating PEG units) rather than 12 as for the synthesis of compound 25.

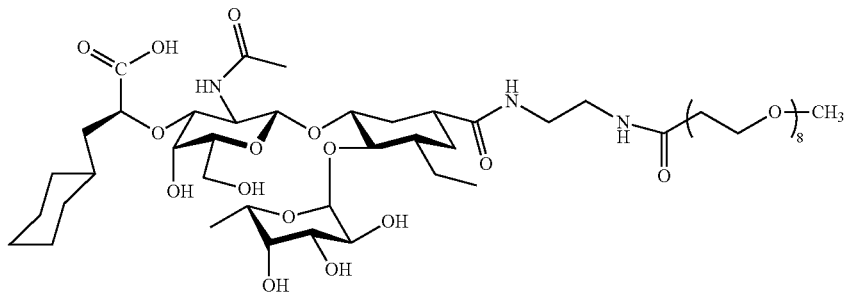

Compound 26 m/z calculated for $C_{52}H_{93}N_3O_{23}$=1127.6. Found=1151.6 (M+Na). $^1$H NMR 600 MHz ($D_2O$, set at 4.67 ppm) d 0.71 (t, J=7.2 Hz, 3H), 0.76 (br quin, J=12.0 Hz, 2H), 0.99-1.06 (m, 4H), 1.08 (d, J=6.6 Hz, 3H), 1.15-1.19 (br quin, J=6.6 Hz, 1H), 1.21-1.25 (m, 2H), 1.39-1.48 (m, 5H), 1.50-1.60 (m, 3H), 1.70 (br d, J=10.2 Hz, 2H), 1.91 (s, 3H), 1.99 (m, 1H), 2.16 (br t, J=12.6 Hz, 1H), 2.36 (t, J=6 Hz, 2H), 3.11-3.15 (m, 2H), 3.18 (t, J=9.6 Hz, 3H), 3.22 (s, 3H), 3.38 (dd, J=7.8 Hz, J=4.2 Hz, 2H), 3.46 (dd, J=4.2 Hz, 1H), 3.47 (s, 1H), 3.52-3.55 (m 27H), 3.56-3.59 (m, 3H), 3.61-3.64 (m, 3H), 3.65 (d, J=3.6 Hz, 1H), 3.72 (dd, J=10.2 Hz, J=3.0 Hz, 1H), 3.80 (d, J=2.4 Hz, 1H), 3.85 (br s, 1H), 3.94 (dd, J=9.6 Hz, J=3.6 Hz, 1H), 4.36 (br s, 1H), 4.77 (q, J=6.6 Hz, 1H), 4.88 (d, J=4.2 Hz, 1H).

Synthesis of Compound 27

Compound 27 was synthesized as described in FIG. 2.

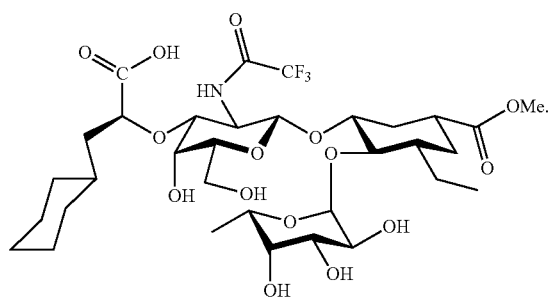

Compound 27

Synthesis of Compound 27A

Compound 19 (0.05 g) was dissolved in $CH_2Cl_2$ (10 ml). To this solution was added $Pd[(Ph_3)P]_4$ (5 mg), Bu3SnH (0.0011 ml), and $(CF3CO)_2O$ (0.0015 ml) with stirring at room temperature. Stirring was continued for 30 min at room temperature. The reaction mixture was evaporated to dryness under reduced pressure and the residue was purified by column chromatography (silica gel) to give compound 27A (0.030 g).

Compound 27A (0.025 g) was subjected to hydrogenation with 10% Pd—C exactly in same way as described for compound 21 and the solvent was evaporated off after filtering of the catalyst. The residue was treated with NaOMe in MeOH as described for compound 22, neutralized with IR-120 (H+) resin, filtered, and the solvent was evaporated off. The residue was purified by reverse phase (C18) HPLC to give compound 27 (7 mg). m/z calculated for $C_{33}H_{52}F_3NO_{15}$=759.3. Found=782.3 (M+Na).

Synthesis of Compound 28

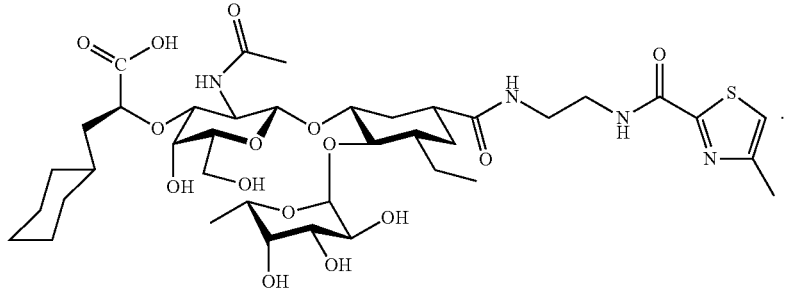

Compound 28

Synthesis Scheme for Compound 28:

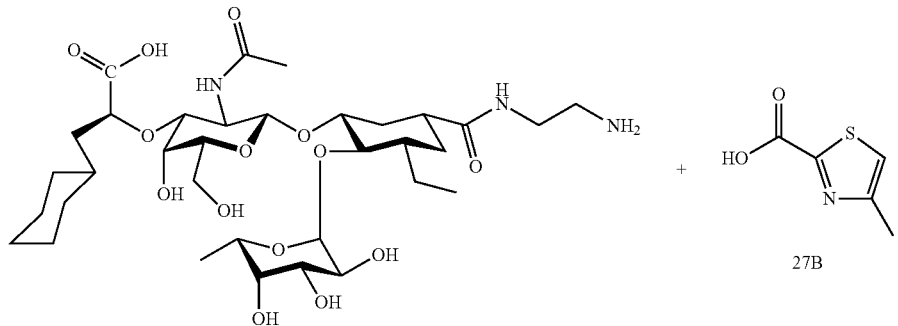

23 + 27B

↓ HATU, DIPEA, DMF

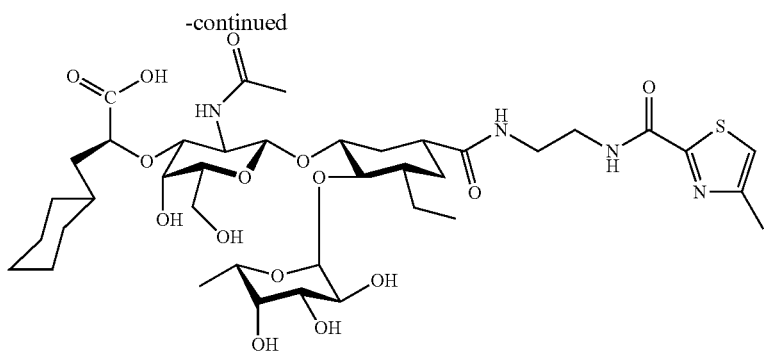

28

Synthesis of Compound 28

Commercially available compound 27B (0.014 g) was dissolved in DMF (1 ml). To this solution was added DIPEA (0.00175 ml) and HATU (0.038 g) and the reaction mixture was stirred for 2 min at room temperature. Compound 23 (0.035 g) was added and the reaction mixture was stirred for 1 h at room temperature. Solvent was evaporated off and the residue was purified by HPLC (C18) to give compound 28 (17 mg).

Synthesis of Compound 29

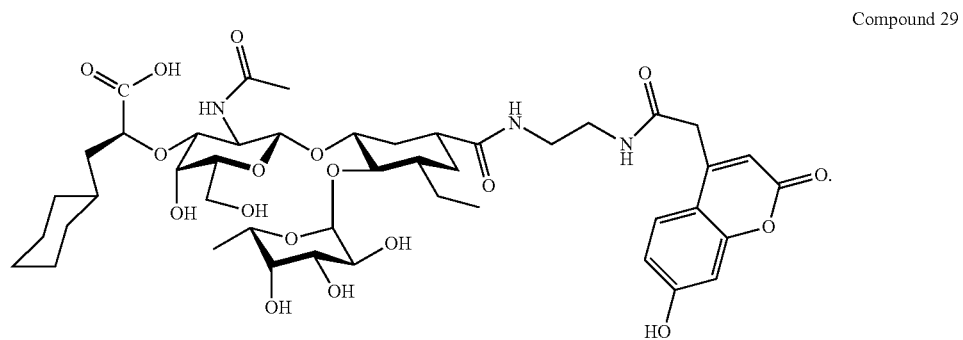

Compound 29

Synthesis Scheme for Compound 29:

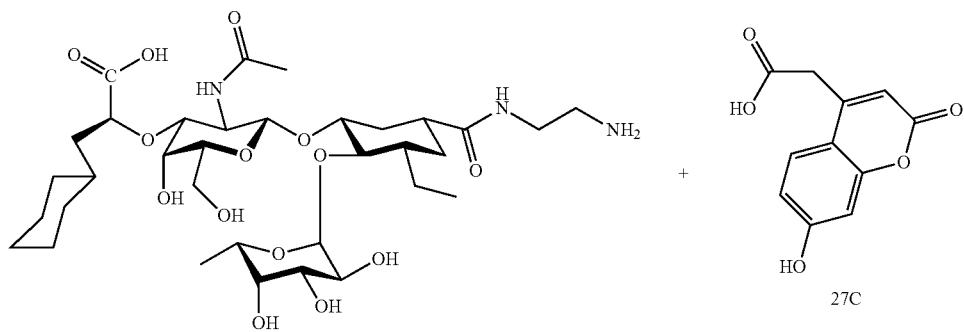

23 + 27C

↓ HATU, DIPEA, DMF

-continued

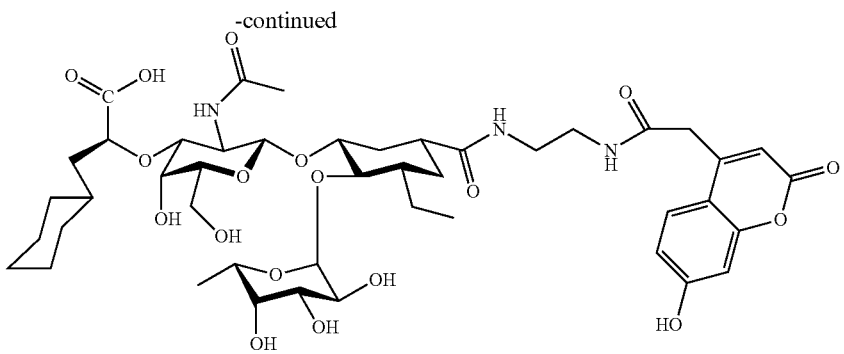

29

Commercially available compound 27C (0.021 g) was reacted with compound 23 (0.035 g) exactly in the same way as described for compound 28 and purified by HPLC (C18) to give compound 29 (0.020 g).

Example 2

E-Selectin Activity

Binding Assay

The inhibition assay to screen for and characterize glycomimetic antagonists of E-selectin is a competitive binding assay, which allows the determination of $IC_{50}$ values. E-selectin/Ig chimera was immobilized in 96 well microtiter plates by incubation at 37° C. for 2 hours. To reduce nonspecific binding, bovine serum albumin was added to each well and incubated at room temperature for 2 hours. The plate was washed and serial dilutions of the test compounds were added to the wells in the presence of conjugates of biotinylated, $sLe^a$ polyacrylamide with streptavidin/horseradish peroxidase and incubated for 2 hours at room temperature.

To determine the amount of $sLe^a$ bound to immobilized E-selectin after washing, the peroxidase substrate, 3,3',5,5' tetramethylbenzidine (TMB) was added. After 3 minutes, the enzyme reaction was stopped by the addition of $H_3PO_4$, and the absorbance of light at a wavelength of 450 nm was determined. The concentration of test compound required to inhibit binding by 50% was determined and reported as the $IC_{50}$ value for each glycomimetic E-selectin antagonist as shown in the table below. $IC_{50}$ values for exemplary compounds disclosed herein are provided in the following table.

E-Selectin Antagonist Activity of Glycomimetic Compounds

| Compound | $IC_{50}$ (μM) |
|---|---|
| 22 | <4.0 |
| 27 | <4.0 |
| 29 | <4.0 |
| 25 | <4.0 |
| 28 | <4.0 |
| 45 | <4.0 |

In addition to reporting the absolute $IC_{50}$ value as measured above, relative $IC_{50}$ values ($rIC_{50}$) are determined by a ratio of the $IC_{50}$ measured for the test compound to that of an internal control (reference) stated for each assay.

Substitution of the methyl group at the $R^3$ position of compound 22 with a trimethylfluoro (—$CF_3$) group did not significantly alter the E-selectin antagonist activity of compound 22; however, the substitution did increase the hydrophobicity of the molecule, thereby improving the bioavailability of the glycomimetic compound.

Example 3

Effects of Treatment with an E-Selectin Specific Antagonist (Compound 25) in a Leukemia Animal Model The E-selectin ligand HCELL (hematopoietic cell E-/L-selectin ligand) is expressed by normal hematopoietic stem cells (Merzaban et al., Blood 118(7):1774-83 (2011)) as a functional glycoform of CD44. High level CD44 expression (99%±1.4%) has also been observed by blasts from 55 patients with acute myeloid leukemia (AML) (i.e., AML blasts) and by putative $CD34^+CD38^-CD123^+$ leukemia stem cells (LSCs) (99.8%±0.6%). The mean fluorescence intensity (MFI) for CD44 expression by AML blasts was one to two logs higher than the MFI for 16 other adhesion receptors. The majority of blasts from patients with AML also express an E-selectin ligand by flow cytometry: >75%% of 22 primary gated blast samples exhibit ≥10% binding of E selectin-IgG chimeric protein with a mean of 22.7%±0.17% SD, range 1.8 to 66.2%. The ligand was identified as HCELL by immunoprecipitation of CD44 from AML cell membranes, followed by staining with HECA 452 antibody that recognizes a functional trisaccharide domain shared by sialyl $Le^a$ and sialyl $Le^x$ and is known to bind to E-selectin. HECA 452 detected the functional glycoform of CD44 known as HCELL, a major ligand for E-selectin, and also identified the human lymphocyte homing receptor CLA (cutaneous lymphocyte antigen).

HECA 452 labeled 5 of 6 patient leukemia blast populations, with mean expression 59.0%±24.8%. HECA 452 antibody labeled $CD34^+CD38^-CD123^+$ LSCs in addition to leukemic blasts with a higher percent expression in most cases for the LSCs than the corresponding unfractionated blast population. HECA 452 also labeled 94% of human AML cells that had been serially engrafted in NODscid $IL2Rgc^{-/-}$ animals, fulfilling the functional definition of LSCs (scid repopulating cells), suggesting that HCELL may be enriched on LSCs. A change in morphology of AML blasts was observed when the cells bound to E-selectin coated plastic.

The AML blasts elongated and became more cuboidal and less reflective in contrast to the non-adherent cells, which remained round and refractile. AML blasts appear to bind to the elongated ends of spindle shaped endothelial cells. Compound 25 (concentration 20 µM) inhibited adhesion of primary human AML cells to E-selectin by an average of 45.0%±9.1% SD for samples from all patients. For one patient for example, the percent inhibition with Compound 25 compared to media control was 33.4%±15.3% SD, p=0.000018.

Adhesion to E-selectin did not confer adhesion-mediated chemotherapy resistance to daunorubicin or cytarabine observed with adhesion to recombinant fibronectin peptide or immobilized VCAM-1 (see Becker et al., *Blood* 113(4):866-74 (2009)). We demonstrated that a glycomimetic compound dual inhibitor of E-selectin and CXCR4 (see U.S. Patent Application Publication No. 2010/0279965) mobilized human AML engrafted in NODscid IL2Rgc$^{-/-}$ mice (see Chien et al., Abstract 579, at American Society for Hematology, 53$^{rd}$ ASH Annual Meeting and Exposition, San Diego, Calif.; Dec. 10-13, 2011; *Blood*, Volume 118, Issue 21) to a greater degree than we observed with CXCR4 inhibitor plerixafor (see Chien et al Abstract 1432, at American Society for Hematology, 53$^{rd}$ ASH Annual Meeting and Exposition, San Diego, Calif.; Dec. 10-13, 2011) alone (3-4 fold vs. approximately 2 fold). The E-selectin antagonist Compound 25 (40 mg/kg) mobilized both human and murine cells in immunodeficient xenograft mice engrafted with human AML. A 2-fold increase in WBC (p=0.00067) and 2-fold increase in human AML cells (p=0.14) was observed at 3 hrs.

In another experiment, mice were engrafted with human AML blasts and treated with Compound 25 in combination with daunorubicin and cytarabine (araC) or with daunorubicin and cytarabine only. When the AML cells comprised about 10% of cells in the blood, the mice were treated. At Days 1, 2, and 3, groups of animals (four per group) Compound 25 was administered at 40 mg/kg twice daily. On Day 1, three hours after the first treatment of the animals with Compound 25, daunorubicin (3 mg/kg) and araC (300 mg/kg) were administered. On Days 2 and 3, three hours after the first dose of Compound 25, only araC (300 mg/kg) was administered. Compound 25 and the chemotherapeutic drugs were administered intraperitoneally. A second group of mice received daunorubicin and araC only. Tumor burden was measured in the bone marrow, blood, and spleen.

The combination of Compound 25 with the two chemotherapeutics resulted in greater depletion of human AML from the bone marrow (22% as many AML cells) and spleen (31% as many AML cells) than observed with daunorubicin and cytarabine in the absence of Compound 25. Without being bound by any particular theory, residence of human AML in the bone marrow vascular niche may involve E-selectin, and migration of AML blasts may involve interactions with the vascular endothelium through E-selectin. See also Chien et al., Poster 4092 at American Society for Hematology, 54$^{th}$ ASH Annual Meeting and Exposition, Atlanta, Ga. Dec. 8-11, 2012; *Blood*, Volume 120, Issue 21.

Example 4

Effects of Treatment with an E-Selectin

Specific Antagonist in a Acute Lymphoblastic Leukemia (ALL) Animal Model

The effectiveness of an E-selectin antagonist in an ALL animal model is determined. The experiments are designed according to methods routinely practiced in the art with respect to choice of an ALL cell line, number of animals per group, dosing and administration schedule of the test groups and controls, and statistical analytical methods. For example, ALL Nalm-6 cells are tagged with green fluorescent protein (GFP) or DiD (a carbocyanine fluorescent dye) and then engrafted into mice ($1\times10^6$ cells per mouse). Approximately one week after administration of the tagged cells to the animals, groups of mice (6 per group) are treated as follows. Group 1 (Control) receives vehicle (PBS) only. Each animal in Group 2 receives an E-selectin antagonist (e.g., Compound 25 (40 mg/kg)) daily on days 1, 2, and 3. The animals in Group 3 receive a chemotherapeutic drug (e.g., doxorubicin (DOX) (2 mg/kg)) daily on days 1, 2, and 3 (called Dose 1). The mice in Group 4 each receive Compound 25 (40 mg/kg) three hours prior to DOX administration (2 mg/kg) once a day on days 1, 2, and 3. Group 5 receives DOX at a dose of 3 mg/kg daily on days 1, 2, and 3 (called Dose 2). In Group 6, each animal receives Compound 25 (40 mg/kg) three hours prior to DOX administration (3 mg/kg) once a day on days 1, 2, and 3. The mice are observed for up to two months. Survival, circulating leukemic cells, and leukemic burden in the bone marrow are determined during the observation period. The number of circulating leukemic cells is determined by in vivo flow cytometry. Intravital microscopy is performed to determine leukemic burden in the bone marrow.

Example 5

Effects of Treatment with an E-Selectin

Specific Antagonist in a Pancreatic Cancer Animal Model

The effectiveness of an E-selectin antagonist in a pancreatic cancer animal model is determined. The pancreas of male athymic nu/nu mice (4-6 weeks old) are injected orthotopically with S2.013 pancreatic cancer cells. Six groups of animals (e.g. 15 mice per group) receive the following treatments beginning approximately 7 days after injection of the pancreatic cancer cells. Alternatively, the animals receive treatments when small tumors are perceptible. Group 1 (Control) receives vehicle (PBS) only. Group 2 receives gemcitabine twice weekly (2/week) for four weeks. Group 3 receives an E-selectin antagonist (e.g. Compound 25 (40 mg/kg)) twice daily (BID) for four weeks. Group 4 receives Compound 25 (40 mg/kg) once daily (qD) for four weeks. Group 5 receives gemcitabine in combination with Compound 25 BID. Group 6 receives gemcitabine (dosed twice daily for four weeks) in combination with Compound 25, which is administered once daily. Tumor burden is determined by ultrasound or 2-deoxyglucose (2DG) imaging. The animals are sacrificed approximately 4 weeks after treatment.

Example 6

Effects of Treatment with an E-Selectin

Specific Antagonist (Compound 25) in an Animal Model of Venous Thromboembolism (VTE)

Animal Model

Most animal models of venous thromboembolism do not test compounds under continuous blood flow, but rather induce thrombosis through ligation or balloon catheterization. A more clinically relevant model was developed in which injury is transiently induced in the presence of continuous blood flow and exposure to normal blood levels of circulating test compound (see, e.g., Diaz et al., *Thromb. Haemot.* 104: 366-375 (2010)). A microelectrode is implanted in the inferior vena cava and a current of 250 uAmps is applied for 15 minutes. Typical endothelial dysfunction found in venous disease was demonstrated by electron microscopy, immunohistochemistry, inflammatory cell counts, and biomarkers of thrombosis. Ultrasound imaging further detected the formation of thrombus in real time under blood flow (see, e.g., Diaz et al., supra).

Male C57BL/6J mice underwent an electrolytic inferior vena cava (IVC) model to produce a non-occlusive thrombosis via electrical stimulation (250 µAmp). Animals were divided into prophylactic or treatment groups. Both groups included the following: non-thrombosed animals (TC, no surgery or drug), 2 Day sham (needle inside the IVC and no current or drug), 2 Day CTR (No Treatment: current and no drug), 2 Day Compound 25 (10 mg/kg IP BID), and low molecular weight heparin (LMWH) (LOVENOX®, 6 mg/kg subcutaneously once a day). Animals were divided into prophylactic or treatment groups. Mice in the prophylactic group were dosed one day pre-thrombus induction through day 1. Animals in the treatment groups received the first dose of the drug following thrombus induction on day 1. Mice were euthanized 2 days post-thrombosis for tissue harvest and blood collection for the following evaluations: thrombus weight; vein wall inflammatory cell counts per high power field; vein wall-thrombus histology; and intra-thrombus polymorphonuclear cell (PMN) counts. A separate group of mice received IV administration of compounds for tail bleeding time evaluation (seconds).

Figure 4:
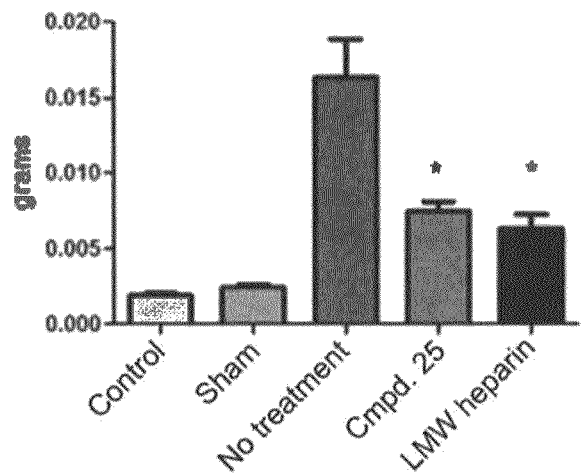
FIG. 4 is a graph depicting the results of a comparison of the effects of compound 25 ("Cmpd. 25") of FIG. 1 versus low molecular weight heparin ("LMW heparin") on the weight of thrombus formed 2 days after EIM (electrolytic inferior vena cava model) injury. "No treatment" represents the weight of the thrombus 2 days after EIM injury. "Control" (saline) represents venous explant with no injury. "Sham" represents a venous explant 2 days after implantation of the electrode with no current. Compound 25 vs. No treatment, P=0.0271; LMW heparin vs. No treatment, P=0.0203.

Thrombus was induced in the inferior vena cava of mice as described above in the electrolytic inferior vena cava model (EIM). After injury, the E-selectin specific antagonist, Compound 25 (Example 1), was administered as a treatment twice a day at 10 mg/kg. Another cohort of mice received low molecular weight heparin (LMW heparin) (Lovenox, once a day, 6 mg/ml). As noted above, on the second day after thrombus induction, the inferior vena cava was removed and weighed. No electrodes were implanted in Control mice. Electrodes were implanted but no amperage was delivered in the inferior vena cava of mice in the Sham cohort. As shown in FIG. 4, treatment with Compound 25 at 10 mg/kg after injury significantly decreased venous thrombus formation (Compound 25 vs. No treatment, P=0.0271) as did LMW heparin (LMW heparin vs. No treatment, P=0.0203). All mice pre-treated prophylactically with Compound 25 or LMWH followed the same pattern of decreasing thrombus weight 2 days post injury (P<0.05).

Example 7

Effect of Compound 25 on Time Required to Form a Clot

To compare anti-coagulant properties of LMW heparin (LMWH) and Compound 25 (see Example 1), bleeding times in mice were evaluated. Test compounds were injected via the penile vein in mice and after 5 minutes the tail vein was nicked with a scalpel. The tail was then placed in a tube of isotonic saline and the time necessary to clot the wound as recorded.

Figure 5:
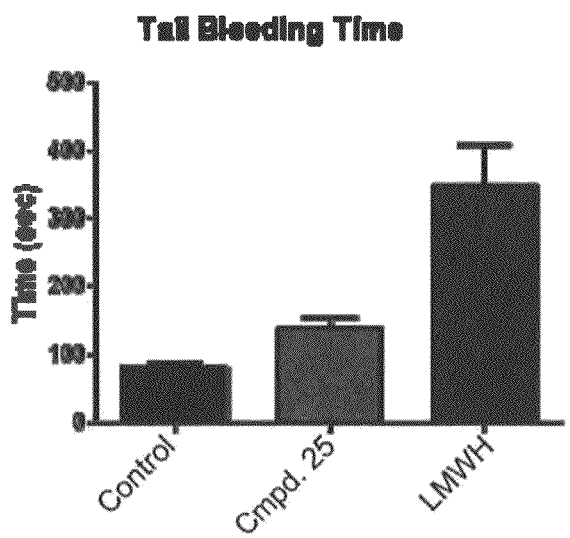
FIG. 5 is a graph depicting the results of a comparison of the effects of compound 25 ("Cmpd. 25") versus low molecular weight heparin ("LMWH") on the time required to form a clot.

LMW heparin is a known anti-coagulant. As shown in FIG. 5, LMW heparin delayed clotting over 4 times longer than control bleeding times, whereas Compound 25 slightly delayed clotting. LMWH at 6 mg/kg dose significantly elevated tail bleeding times in mice versus controls (341±27, 491±60 vs. 82±6 seconds, P<0.01). Compound 25 (10 mg/kg, IV) had significantly lower tail bleeding times compared to an IV dose of LMWH (6 mg/kg, P<0.01). Compound 25 is a significant improvement in reducing bleeding time over LMW heparin.

Vein Wall Morphometrics and Histology:

Mice that were treated with Compound 25 after injury had significantly decreased vein wall monocyte extravasation compared to controls (P<0.05). When animals were treated with Compound 25 or LMWH prophylactically (i.e., prior to injury), significantly decreased vein wall PMN extravasation was observed 2 days post thrombosis (P=0.027 and P=0.007 respectively). The same pattern held true for prophylaxis with Compound 25 and LMWH on vein wall monocyte extravasation at the same time point (P<0.01).

Intra-Thrombus PMN Counts:

Compound 25 administered as a prophylactic therapy significantly decreased intra-thrombus cell counts versus control animal (14.5±3.7 vs. 37.4±4.7 PMNs/HPF, P=0.009), and these animals had decreased venous thrombus burden. Only mice that received Compound 25 therapy visually had more intra-thrombus vascular channels compared to control animals and mice receiving LMWH therapy.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A compound having the formula (I):

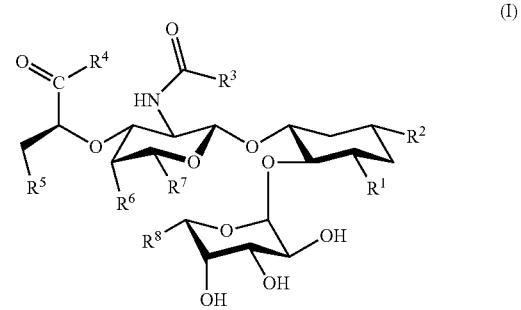

or a pharmaceutically acceptable salt, isomer, tautomer, hydrate or solvate thereof, wherein:

$R^1$ is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

$R^2$ is a linker-non-glycomimetic moiety, wherein the non-glycomimetic moiety comprises polyethylene glycol;

R[3] is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl or cyclopropyl;

R[4] is —OH or —NZ[1]Z[2] where Z[1] and Z[2] are each independently H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl or wherein Z[1] and Z[2] join to form a ring;

R[5] is $C_3$-$C_8$ cycloalkyl;

R[6] is —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl;

R[7] is —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl; and R[8] is $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl or $C_2$-$C_8$ haloalkynyl.

2. The compound of claim 1 having the formula:

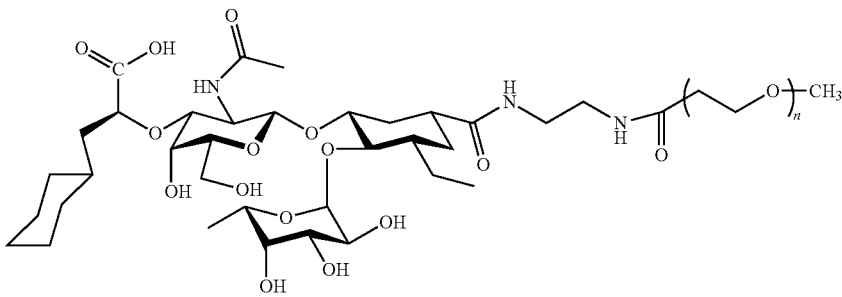

or

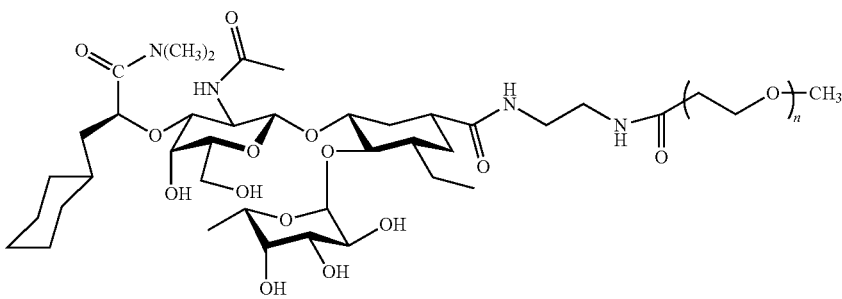

wherein n is 1 to 100.

3. The compound of claim 2, wherein n is 4, 8, 12, 16, 20, 24, or 28.

4. The compound of claim 3 having one of the formulae:

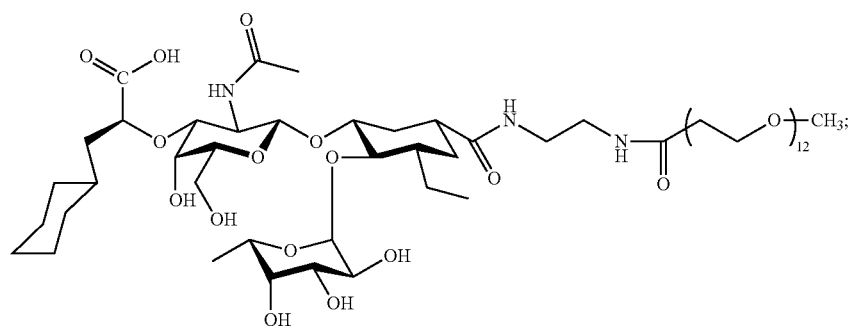

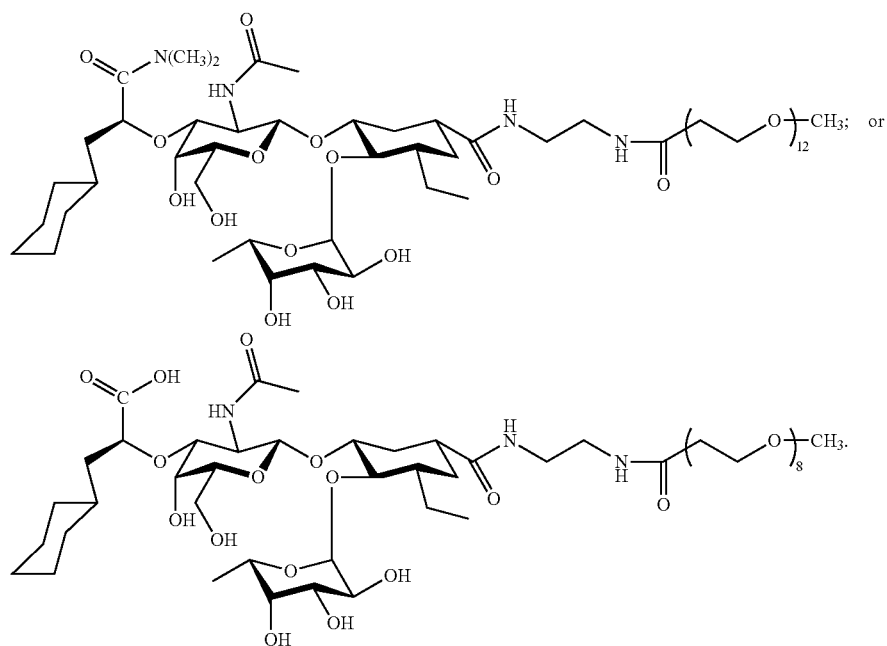

5. The compound of claim 4, wherein the compound is:

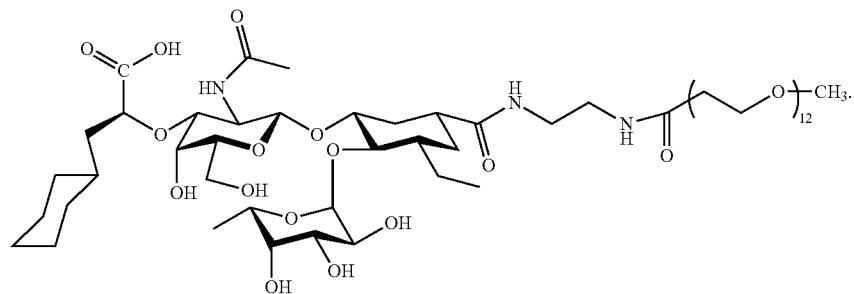

6. A pharmaceutical composition comprising a compound of claim 1 and optionally at least one pharmaceutically acceptable excipient.

7. A method for treating, decreasing, inhibiting, or reducing the likelihood of metastasis of cancer cells in a subject, comprising administering to the subject a pharmaceutical composition of claim 6.

8. A method for inhibiting infiltration of cancer cells into bone marrow in a subject, said method comprising administering to the subject a pharmaceutical composition of claim 6.

9. A method for inhibiting adhesion of a tumor cell that expresses a ligand of E-selectin to an endothelial cell expressing E-selectin, said method comprising contacting the endothelial cell with a compound of claim 1 and permitting the compound to interact with E-selectin present on the endothelial cell, thereby inhibiting binding of the tumor cell to the endothelial cell.

10. A method for inhibiting adhesion of a tumor cell that expresses a ligand of E-selectin to an endothelial cell expressing E-selectin, said method comprising administering a pharmaceutical composition comprising a compound of claim 1 and optionally at least one pharmaceutically acceptable excipient and permitting the compound to interact with E-selectin present on the endothelial cell, thereby inhibiting binding of the tumor cell to the endothelial cell.

11. The method of claim 9 or 10, wherein the endothelial cell is present in the bone marrow.

12. A method for treating a cancer in a subject comprising administering to the subject (a) a pharmaceutical composition of claim 6 and (b) at least one of (i) chemotherapy and (ii) radiotherapy.

13. A method for treating, decreasing, inhibiting, or reducing the likelihood of thrombosis in a subject, comprising administering to the subject a pharmaceutical composition of claim 6.

14. A method for enhancing hematopoietic stem cell survival in a subject, comprising administering to the subject a pharmaceutical composition of claim 6.

15. The method of claim 14, wherein the subject has received or will receive chemotherapy or radiotherapy or both chemotherapy and radiotherapy.

\* \* \* \* \*

UNITED STATES PATENT AND TRADEMARK OFFICE
CERTIFICATE OF CORRECTION

| | |
|---|---|
| PATENT NO. | : 9,109,002 B2 |
| APPLICATION NO. | : 14/367561 |
| DATED | : August 18, 2015 |
| INVENTOR(S) | : John L. Magnani et al. |

It is certified that error appears in the above-identified patent and that said Letters Patent is hereby corrected as shown below:

IN THE DRAWINGS

Fig. 1A, "Trichloroacetamidate" should read --Trichloroacetimidate--.

IN THE SPECIFICATION

Column 6, line 52, "content" should read --context--.

Column 10, line 5, "Dithiadiazoleoxide" should read --Thiadiazoleoxide--.

Column 11, line 31, "CH2F" should read --$CH_2F$--.

Column 26, line 65, "treatise" should read --treatises--.

Column 27, line 10, "treatise" should read --treatises--.

Column 27, line 58, "that that" should read --that--.

Column 44, line 67, "m-chloroperbenzoic acid" should read --m-Chloroperbenzoic acid--.

Column 45, line 21, "Et2O" should read --$Et_2O$--.

Column 45, line 29, "SiO2" should read --$SiO_2$--.

Column 46, line 8, "overnight under" should read --under--.

Column 46, line 27, "NH4OAC" should read --$NH_4OAc$--.

Column 46, line 32, "Na2SO4" should read --$Na_2SO_4$--.

Signed and Sealed this
Seventeenth Day of May, 2016

Michelle K. Lee
*Director of the United States Patent and Trademark Office*

CERTIFICATE OF CORRECTION (continued)
U.S. Pat. No. 9,109,002 B2

IN THE SPECIFICATION

Column 47, line 1, "0.35 mg" should read --0.35 mL--.

Column 50, line 4, "Bu3SnH" should read --$Bu_3SnH$--.

Column 50, line 5, "($CF3CO)_2O$" should read --$(CF_3CO)_2O$--.